US008268972B2

(12) United States Patent
Whitfeld et al.

(10) Patent No.: US 8,268,972 B2
(45) Date of Patent: Sep. 18, 2012

(54) HUMANIZED ANTI-C5AR ANTIBODIES

(75) Inventors: Peter Whitfeld, Surry Hills (AU); David Zahra, West Pennant Hills (AU); Charles Mackay, Vaucluse (AU)

(73) Assignee: G2 Inflammation Pty Ltd, Darlinghurst (AU)

( * ) Notice: Subject to any disclaimer, the term of this patent is extended or adjusted under 35 U.S.C. 154(b) by 204 days.

(21) Appl. No.: 12/866,009

(22) PCT Filed: Feb. 19, 2009

(86) PCT No.: PCT/AU2009/000184
§ 371 (c)(1),
(2), (4) Date: Sep. 1, 2010

(87) PCT Pub. No.: WO2009/103113
PCT Pub. Date: Aug. 27, 2009

(65) Prior Publication Data
US 2011/0190477 A1      Aug. 4, 2011

Related U.S. Application Data

(60) Provisional application No. 61/066,539, filed on Feb. 20, 2008.

(51) Int. Cl.
*C07K 16/28* (2006.01)
(52) U.S. Cl. ............ 530/388.22; 530/387.1; 530/387.3; 530/388.1; 530/388.2
(58) Field of Classification Search .................. None
See application file for complete search history.

(56) References Cited

U.S. PATENT DOCUMENTS

| 3,850,752 | A | 11/1974 | Schuurs et al. |
| 3,901,654 | A | 8/1975 | Gross |
| 4,098,876 | A | 7/1978 | Piasio et al. |
| 4,676,980 | A | 6/1987 | Segal et al. |
| 4,704,362 | A | 11/1987 | Itakura et al. |
| 5,194,594 | A | 3/1993 | Khawli et al. |
| 5,284,746 | A | 2/1994 | Sledziewski et al. |
| 5,304,489 | A | 4/1994 | Rosen |
| 5,354,678 | A | 10/1994 | Lebowski et al. |
| 5,480,974 | A | 1/1996 | Morgan et al. |
| 5,741,957 | A | 4/1998 | Deboer et al. |
| 5,849,992 | A | 12/1998 | Meade et al. |
| 5,861,272 | A | 1/1999 | Li et al. |
| 8,071,096 | B2 | 12/2011 | Mackay |

FOREIGN PATENT DOCUMENTS

| EP | 0377489 | 7/1990 |
| EP | 0586505 | 3/1994 |
| JP | 8109200 | 4/1996 |
| WO | WO 9100360 | 1/1991 |
| WO | WO 9220373 | 11/1992 |
| WO | WO 9407921 | 4/1994 |
| WO | WO 9411026 | 5/1994 |
| WO | WO 9420142 | 9/1994 |
| WO | WO 9500164 | 1/1995 |
| WO | WO 9639511 | 12/1996 |
| WO | WO 9833908 | 8/1998 |
| WO | WO 9844001 | 10/1998 |
| WO | WO 0238767 | 5/2002 |
| WO | WO 03062278 | 7/2003 |
| WO | WO 2005060739 | 7/2005 |
| WO | WO 2008022390 | 2/2008 |
| WO | WO 2008022391 | 2/2008 |

OTHER PUBLICATIONS

Barry, et al. (1994) "Sequencing and Modeling of Anti-DNA Immunoglobulin Fv Domains. Comparison with Crystal Structures" *J. Biol. Chem.* 269(5):3623-3632.
Berman, et al. (1988) "Lymphocyte Motility and Lymphocyte Chemoattractant Factors" *Immunol. Invest.* 17(8-9):625-677.
Caldas, et al. (2000) "Design and Synthesis of Germline-Based Hemi-Humanized Single-Chain Fv against the CD18 Surface Antigen" *Protein Eng.* 13(5):353-360.
Caldas, et al. (2003) "Humanization of the Anti-CD18 Antibody 6.7: An Unexpected Effect of a Framework Residue in Binding to Antigen" *Mol. Immunol.* 39(15):941-952.
Caron, et al. (1992) "Engineered Humanized Dimeric Forms of IgG Are More Effective Antibodies" *J. Exp. Med.* 176(4):1191-1195.
Chothia & Lesk (1987) "Canonical Structures for the Hypervariable Regions of Immunoglobulins" *J. Mol. Biol.* 196(4):901-917.
Chothia, et al. (1989) "Conformations of Immunoglobulin Hypervariable Regions" *Nature* 342(6252):877-883.
Co, et al. (1992) "Chimeric and Humanized Antibodies with Specificity for the CD33 Antigen" *J. Immunol.* 148(4):1149-1154.
Curiel, et al. (1992) "High-Efficiency Gene Transfer Mediated by Adenovirus Coupled to DNA-Polylysine Complexes" *Hum. Gene Ther.* 3(2):147-154.
Dahinden, et al. (1994) "Monocyte Chemotactic Protein 3 Is a Most Effective Basophil- and Eosinophil-Activating Chemokine" *J. Exp. Med.* 179(2):751-756.
Dai, et al. (1992) "Gene Therapy via Primary Myoblasts: Long-Term Expression of Factor IX Protein Following Transplantation in Vivo" *Proc. Natl. Acad. Sci. USA* 89(22):10892-10895.
Eigenbrot, et al. (1993) "X-ray Structures of the Antigen-Binding Domains from Three Variants of Humanized Anti-p185HER2 Antibody 4D5 and Comparison with molecular Modeling" *J. Mol. Biol.* 229(4):969-995.
Gerard & Gerard (1991) "The Chemotactic Receptor for Human C5a Anaphylatoxin" *Nature* 349(6310):614-617.
Gerard & Gerard (1994) "C5A Anaphylatoxin and Its Seven Transmembrane-Segment Receptor" *Annu. Rev. Immunol.* 12:775-808.
Hansen & Balthasar (2002) "Intravenous Immunoglobulin Mediates an Increase in Anti-Platelet Antibody Clearance via the FcRn Receptor" *Thromb. Haemost.* 88(6):898-899.
Hendrickson, et al. (1995) "High Sensitivity Multianalyte Immunoassay Using Covalent DNA-Labeled Antibodies and Polymerase Chain Reaction" *Nucleic Acids Res.* 23(3):522-529.

(Continued)

*Primary Examiner* — Phillip Gambel
(74) *Attorney, Agent, or Firm* — Carol L. Francis; Bozicevic, Field & Francis LLP

(57) ABSTRACT

The present invention is directed to humanized antibodies which bind the human C5a receptor and their use as therapeutic and diagnostic agents. The present invention is further directed toward nucleic acid sequences which encode said humanized antibodies, and their expression in recombinant host cells. In particular, the present invention is directed towards humanized antibodies derived from murine antibody 7F3 which specifically binds to the human C5a receptor.

7 Claims, 37 Drawing Sheets

OTHER PUBLICATIONS

Figure 2B:
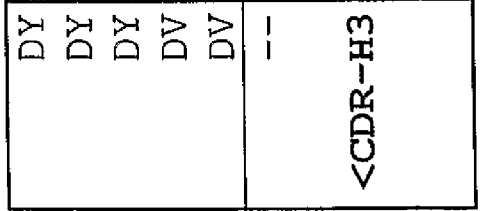

Ji, et al. (2002) "Arthritis Critically Dependent on Innate Immune System Players" *Immunity* 16(2):157-168.

Jones, et al. (1986) "Replacing the Complementarity-Determining Regions in a Human Antibody with Those from a Mouse" *Nature* 321(6069):522-525.

Jose, et al. (1994) "Eotaxin: A Potent Eosinophil Chemoattractant Cytokine Detected in a Guinea Pig Model of Allergic Airways Inflammation" *J. Exp. Med.* 179(3):881-887.

Kaneko, et al. (1995) "Antagonistic Peptides against Human Anaphylatoxin C5a" *Immunology* 86(1):149-154.

Kavanaugh, et al. (1991) "Role of CD11/CD18 in Adhesion and Transendothelial Migration of T Cells. Analysis Utilizing CD18-Deficient T Cell Clones" *J. Immunol.* 146(12):4149-4156.

Konteatis, et al. (1994) "Development of C5a Receptor Antagonists. Differential Loss of Functional Responses" *J. Immunol.* 153(9):4200-4205.

Kouskoff, et al. (1996) "Organ-Specific Disease Provoked by Systemic Autoimmunity" *Cell* 87(5):811-822.

Kozlov, et al. (2004) "Efficient Strategies for the Conjugation of Oligonucleotides to Antibodies Enabling Highly Sensitive Protein Detection" *Biopolymers* 73(5):621-630.

Kyburz & Corr (2003) "The KRN Mouse Model of Inflammatory Arthritis" *Springer Semin. Immunopathol.* 25(1):79-90.

Lebkowski, et al. (1988) "Adeno-Associated Virus: A Vector System for Efficient Introduction and Integration of DNA into a Variety of Mammalian Cell Types" *Mol. Cell. Biol.* 8(10):3988-3996.

Lee, et al. (2002) "Mast Cells: A Cellular Link between Autoantibodies and Inflammatory Arthritis" *Science* 297(5587):1689-1692.

Lee, et al. (2006) "Human C5aR Knock-In Mice Facilitate the Production and Assessment of Anti-Inflammatory Monoclonal Antibodies" *Nat. Biotechnol.* 24(10):1279-1284.

Lowenstein, et al. (2006) "Different Mechanisms of Campath-1H-Mediated Depletion for CD4 and CD8 T Cells in Peripheral Blood" *Transplant International* 19(11):927-936.

Martin, et al. (1989) "Modeling Antibody Hypervariable Loops: A Combined Algorithm" *Proc. Natl. Acad. Sci. USA* 86(23):9268-9272.

Mayo & Curnutte (1990) "Kinetic Microplate Assay for Superoxide Production by Neutrophils and Other Phagocytic Cells" *Methods Enzymol.* 186:567-575.

Morgan, et al. (1993) "Anti-C5a Receptor Antibodies. Characterization of Neutralizing Antibodies Specific for a Peptide, C5aR-(9-29), Derived from the Predicted Amino-Terminal Sequence of the Human C5a Receptor" *J. Immunol.* 151(1):377-388.

Murdoch & Finn (2000) "Chemokine Receptors and Their Role in Inflammation and Infectious Diseases" *Blood* 95(10):3032-3043.

Needleman & Wunsch (1970) "A General Method Applicable to the Search for Similarities in the Amino Acid Sequence of Two Proteins" *J. Mol. Biol.* 48(3):444-453.

Neote, et al. (1993) "Molecular Cloning, Functional Expression, and Signaling Characteristics of a C-C Chemokine Receptor" *Cell* 72(3):415-425.

Niemeyer, et al. (2003) "Combination of DNA-Directed Immobilization and Immuno-PCR: Very Sensitive Antigen Detection by Means of Self-Assembled DNA-Protein Conjugates" *Nucl. Acids Res.* 31(16):e90.

Nisihara, et al. (2001) "Humanization and Epitope Mapping of Neutralizing Anti-Human Fas Ligand Monoclonal Antibodies: Structural Insights into Fas/Fas Ligand Interaction" *J. Immunol.* 167(6):3266-3275.

Pellas, et al. (1998) "Novel C5 Receptor Antagonists Regulate Neutrophil Functions In Vitro and In Vivo" *J. Immunol.* 160(11):5616-5621.

Preithner, et al. (2006) "High Concentrations of Therapeutic IgG1 Antibodies Are Needed to Compensate for Inhibition of Antibody-Dependent Cellular Cytotoxicity by Excess Endogenous Immunoglobulin G" *Mol. Immunol.* 43(8):1183-1189.

Pulito, et al. (1996) "Humanization and Molecular Modeling of the Anti-CD4 Monoclonal Antibody, OKT4A" *J. Immunol.* 156(8):2840-2850.

Queen, et al. (1986) "Cell-Type Specific Regulation of a Kappa Immunoglobulin Gene by Promoter and Enhancer Elements" *Immunol. Rev.* 89:49-68.

Rudikoff, et al. (1982) "Single Amino Acid Substitution Altering Antigen-Binding Spec" *Proc. Natl. Acad. Sci. USA* 79(6):1979-1983.

Shopes (1992) "A Genetically Engineered Human IgG Mutant with Enhanced Cytolytic Activity" *J. Immunol.* 148(9):2918-2922.

Solomon, et al. (2005) "A Crucial Role for Macrophages in the Pathology of K/B x N Serum-Induced Arthritis" *Eur. J. Immunol.* 35(10):3064-3073.

Stevenson, et al. (1989) "A Chimeric Antibody with Dual Fc Regions (bisFabFc) Prepared by Manipulations at the IgG Hinge" *Anticancer Drug Design* 3(4):219-230.

Ulmer, et al. (1993) "Heterologous Protection against Influenza by Injection of DNA Encoding a Viral Protein" *Science* 259(5102):1745-1749.

Van Damme, et al. (1992) "Structural and Functional Identification of Two Human, Tumor-Derived Monocyte Chemotactic Proteins (MCP-2 and MCP-3) Belonging to the Chemokine Family" *J. Exp. Med.* 176(1):59-65.

Van Meerten, et al. (2006) "Complement-Induced Cell Death by Rituximab Depends on CD20 Expression Level and Acts Complementary to Antibody-Dependent Cellular Cytotoxicity" *Clin. Cancer Res.* 12(13):4027-4035.

Van Riper, et al. (1993) "Characterization and Species Distribution of High Affinity GTP-Coupled Receptors for Human Rantes and Monocyte Chemoattractant Protein 1" *J. Exp. Med.* 177(3):851-856.

Verhoeyen, et al. (1988) "Reshaping Human Antibodies: Grafting an Antilysozyme Activity" *Science* 239(4847):1534-1536.

Vitetta (1993) "Immunotoxins: Magic Bullets or Misguided Missiles?" *Immunol. Today* 14(6):252-259.

Vitetta, et al. (1987) "Redesigning Nature's Poisons to Create Anti-Tumor Reagents" *Science* 238(4830):1098-1104.

Watanabe, et al. (1995) "Analysis of C5a Receptor by Monoclonal Antibody" *J. Immunol. Methods* 185(1):19-29.

Williams, et al. (1991) "Introduction of Foreign Genes into Tissues of Living Mice by DNA-Coated Microprojectiles" *Proc. Natl. Acad. Sci. USA* 88(7):2726-2730.

Wipke & Allen (2001) "Essential Role of Neutrophils in the Initiation and Progression of a Murine Model of Rheumatoid Arthritis" *J. Immunol.* 167(3):1601-1608.

Wolff, et al. (1993) "Monoclonal Antibody Homodimers: Enhanced Antitumor Activity in Nude Mice" *Cancer Res.* 53(11):2560-2565.

Wu & Wu (1987) "Receptor-Mediated In Vitro Gene Transformation by a Soluble DNA Carrier System" *J. Biol. Chem.* 262(10):4429-4432.

Zachariae, et al. (1990) "Properties of Monocyte Chemotactic and Activating Factor (MCAF) purified from a Human Fibrosarcoma Cell Line" *J. Exp. Med.* 171(6):2177-2182.

U.S. Appl. No. 13/280,250, filed Oct. 24, 2011, Mackay.

Monk, et al. (2007) "Function, Structure and Therapeutic Potential of Complement C5a Receptors" *Br. J. Pharmacol.* 152(4):429-448.

Proctor, et al. (2006) "Recent Developments in C5/C5a Inhibitors" *Expert Opinion on Therapeutic Patents* 16(4):445-458.

Whitfeld, et al. (2007) "Novel mAbs to C5aR $2^{nd}$ Loop Reverse Disease in Models of Inflammatory Arthritis" *Inflamm. Res.* 56(Suppl. 3):S401.

Wu (2003) "Simultaneous Humanization and Affinity Optimization of Monoclonal Antibodies" *Methods Mol. Biol.* 207:197-212.

Cain, et al. (2001) "Mapping the Ligand-Binding Site on the C5a Receptor: Arginine74 of C5a Contacts Aspartate282 of the C5a Receptor" *Biochemistry* 40(46):14047-14052.

Cain, et al. (2001) "Modulation of Ligand Selectivity by Mutation of the First Extracellular Loop of the Human C5a Receptor" *Biochem. Pharmacol.* 61(12):1571-1579.

Casset, et al. (2003) "A Peptide Mimetic of an Anti-CD4 Monoclonal Antibody by Rational Design" *Biochem. Biophys. Res. Commun.* 307(1):198-205.

Charlton et al. (1999) "The Expression of C5A Receptor (C5AR) (CD88) Is Associated with the Progression of Inflammation in Human Disease" *J. Pathol.* 187(Suppl.):36A.

Chen, et al. (1995) "Enhancement and Destruction of Antibody Function by Somatic Mutation: Unequal Occurrence Is Controlled by V Gene Combinatorial Associations" *EMBO J.* 14(12):2784-2794.

Colman (1994) "Effects of Amino Acid Sequence Changes on Antibody-Antigen Interactions" *Res. Immunol.* 145(1):33-36.

Crass, et al. (1999) "Chimeric Receptors of the Human C3a Receptor and C5a Receptor (CD88)" *J. Biol. Chem.* 274(13):8367-8370.

Crass, et al. (1999) "Receptor Activation by Human C5a des Arg74 but Not Intact C5a Is Dependent on an Interaction between Glu199 of the Receptor and Lys68 of the Ligand" *Biochemistry* 38(30):9712-9717.

Demartino, et al. (1995) "Arginine 206 of the C5a Receptor Is Critical for Ligand Recognition and Receptor Activation by C-Terminal Hexapeptide Analogs" *J. Biol. Chem.* 270(27):15966-15969.

Elsner, et al. (1994) "C3a Activates the Respiratory Burst in Human Polymorphonuclear Neutrophilic Leukocytes via Pertussis Toxin-Sensitive G-Proteins" *Blood* 83(11):33224-3331.

Extended European Search Report for European Application No. 10009060.4, dated Jul. 29, 2011.

Farkas, et al. (1999) "C5a Receptor Expression by TGW Neuroblastoma Cells" *Neuroreport* 10(14):3021-3025.

Fayyazi et al. (2000) "The C5a Receptor Is Expressed in Normal Renal Proximal Tubular but Not in Normal Pulmonary or Hepatic Epithelial Cells" *Immunology* 99(1):38-45.

Fitzgerald (1987) "Construction of Immunotoxins Using *Pseudomonas* Exotoxin A" *Methods Enzymol.* 151:139-145.

Gerber, et al. (2001) "An Activation Switch in the Ligand Binding Pocket of the C5a Receptor" *J. Biol. Chem.* 276(5):3394-3400.

Jagels, et al. (1996) "Proteolytic Inactivation of the Leukocyte C5a Receptor by Proteinases Derived from *Porphyromonas gingivalis*" *Infect. Immun.* 64(6):1984-1991.

Kussie, et al. (1994) "A Single Engineered Amino Acid Substitution Changes Antibody Fine Specificity" *J. Immunol.* 152(1):146-152.

MacCallum, et al. (1996) "Antibody-Antigen Interactions: Contact Analysis and Binding Site Topography" *J. Mol. Biol.* 262(5):732-745.

Monk, et al. (1995) "Mutation of Glutamate 199 of the Human C5a Receptor Defines a Binding Site for Ligand Distinct from the Receptor N Terminus" *J. Biol. Chem.* 270(28):16625-16629.

Oppermann, et al. (1993) "Probing the Human Receptor for C5a Anaphylatoxin with Site-Directed Antibodies. Identification of a Potential Ligand Binding Site on the NH2-Terminal Domain" *J. Immunol.* 151(7):3785-3794.

Pease, et al. (1994) "Generation of Chimeric C5a/Formyl Peptide Receptors: Towards the Identification of the Human C5a Receptor Binding Site" *Eur. J. Immunol.* 24(1):211-215.

Raffetseder, et al. (1996) "Site-Directed Mutagenesis of Conserved Charged Residues in the Helical Region of the Human C5a Receptor. Arg2O6 Determines High-Affinity Binding Sites of C5a Receptor" Eur. J. Biochem. 235 (1-2):82-90.

Rothermel, et al. (2000) "Analysis of the Tissue Distribution of the Rat C5a Receptor and Inhibition of C5a-Mediated Effects through the Use of Two MoAbs" Scand. J. Immunol. 52(4):401-410.

Sayah, et al. (1999) "Expression of Cytokines by Human Astrocytomas Following Stimulation by C3a Anaphylatoxins: Specific Increase in Interleukin-6 mRNA Expression" *J. Neurochem.* 72(6):2426-2436.

Schlaf, et al. (1999) "Differential Expression of the C5a Receptor on the Main Cell Types of Rat Liver as Demonstrated with a Novel Monoclonal Antibody and by C5a Anaphylatoxin-Induced Ca2+ Release" *Lab. Invest.* 79(10):1287-1297.

Wu, et al. (1999) "Humanization of a Murine Monoclonal Antibody by Simultaneous Optimization of Framework and CDR Residues" *J. Mol. Biol.* 294(1):151-162.

|  | 10 | 20 | 30 | 40 | 50 | 60 |  |
|---|---|---|---|---|---|---|---|
| KV2F_human | DVVMTQSPLSLPVTLGQPASISC | RSSQSLVYS-DGNTYLN | WFQQRPGQSPRRLIY | KVSNRDS |
| KV2E_human | DIVMTQSPLSLPVTPGEPASISC | RSSQSLLHS-NGYNYLD | WYLQKPQQSPQLLIY | LGSNRAS |
| KV2D_human | DIVMTQSPLSLPVTPGEPASISC | RSSQSLLHS-DGFDYLN | WYLQKPGQSPZLLIY | ALSNRAS |
| KV2B_human | DVVMTQSPLFLPVTLGEPASIQC | RSSQSLVYR-BGBTYLB | WYLQKPGQSPELLIY | LSSYRDS |
| KV2A_human | DIVMTQTPLSLPVTPGEPASIGS | RSSQSLILDSGDGNTYLN | WYLQKAGQSPQLLIY | TLSYRAS |
| X12691 | DIVMTQSPLSLPVTPGEPASISC | RSSQSLLHS-NGYNYLD | WYLQKPGQSPQLLIY | LGSNRAS |
| U41644 | DIVMTQTPLSLSVTPGQPASISC | KSSQSLLHS-DGKTYLY | WYLQKPGQSPQLLIY | EVSNRFS |
| U41645 | DIVMTQTPLSLSVTPGQPASISC | KSSQSLLHS-DGKTYLY | WYLQKPGQSPQLLIY | EVSSRFS |
| M31952 | DIVMTQTPLSLSVTPGQPASISC | KSSQSLLHS-DGKTYLY | WYLQKPGQPPQLLIY | EVSNRFS |
| hVkFW Cons | DIVMTQSPLSLPVTPGEPASISC |  | WYLQKPGQSPQLLIY |  |
|  |  | CDR-L1 |  | CDR-L2 |

|  | 70 | 80 | 90 | 100 | 112 |  |
|---|---|---|---|---|---|---|
| KV2F_human | GVPDRFSGSGSGTDFTLKISRVEAEDVGVYYC | MQGTHWSWT | FGQGTKVEIK |
| KV2E_human | GVPDRFSGSGSGTDFTLKISRVEAEDVGVYYC | MQGLQTPQT | FGQGTKVEIK |
| KV2D_human | GVPDRFSGSGSGTDFTLKISRVEAEDVGVYYC | MZALQAPIT | FGQGTRLEIK |
| KV2B_human | GVPDRFSDSGSGTDFTLKITRVQAEDVGVYYC | MQATZSPYT | FGQGTKLZIK |
| KV2A_human | GVPDRFSGSGSGTDFTLKISRVQAEDVGVYYC | MQRLEIPYT | FGQGTKLEIR |
| X12691 | GVPDRFSGSGSGTDFTLKISRVEAEDVGVYYC | MQALQTP |  |
| U41644 | GVPDRFSGSGSGTDFTLKISRVEAEDVGVYYC | MQSIQLP |  |
| U41645 | GVPDRFSGSGSGTDFTLKISRVEAEDVGVYYC | MQGIHLP |  |
| M31952 | GVPDRFSGSGSGTDFTLKISRVEAEDVGVYYC | MQSIQLP |  |
| hVkFW Cons | GVPDRFSGSGSGTDFTLKISRVEAEDVGVYYC |  | FGQGTKLEIK |
|  |  |  | CDR-L3 |  |

Figure 1

```
                       10        20         30          40      49
                                            |CDR-H1|
HV1Av_HUMAN    QVQLVQSGAEVKKPGSSVKVSCKAS GGTFSRSAII WVRQAPGQGLEWMG
HV1Bv_HUMAN    QVQLVQSGAEVKKPGASVKVSCKAS GYTFNSYYMH WVRQAPGQGLEWMG
HV1Cv_HUMAN    QTQLVQSGAEVRKPGASVRVSCKAS GYTFIDSYIH WIRQAPGHGLEWVG
HV1Gv_HUMAN    QVQLVQSGAEVKKPGASVKVSCKAS GYTFTGYYMH WVRQAPGQGLEWMG
M99641         QVQLVQSGAEVKKPGASVKVSCKAS GYTFTSYGIS WVRQAPGQGLEWMG
M99642         QVQLVQSGAEVKKPGASVKVSCKVS GYTLTELSMH WVRQAPGKGLEWMG
X62109         QVQLVQSGAEVKKPGASVKVSCKAS GYTFTSYAMH WVRQAPGQRLEWMG
X92343         QVQLVQSGAEVKKPGASVKVSCKAS GYTFTSYYMH WVRQAPGQGLEWMG
Z12305         EVQLVQSGAEVKKPGATVKISCKVS GYTFTDYYMH WVQQAPGKGLEWMG
hVhvFW Cons    QVQLVQSGAEVKKPGASVKVSCKAS ---------- WVRQAPGQGLEWMG 60          70             80           90     98
                    |CDR-H2|                                        |CDR-H3>
HV1Av_HUMAN    GIVPMFGPPNYAQKFQG RVTITADESTNTAYMELSSLRSEDTAFYFC AG
HV1Bv_HUMAN    IINPSGGSTSYAQKFQG RVTMTRDTSTSTVYMELSSLRSEDTAVYYC AR
HV1Cv_HUMAN    WINPNSGGTNYAPREQG RVTMTRDASESTAYMDLRSLRSDDSAVFYC AK
HV1Gv_HUMAN    RINPNSGGTNYAQKFQG RVTSTRDTSISTAYMELSRLRSDDTVVYYC AR
M99641         WISAYNGNTNYAQKLQG RVTMTTDTSTSTAYMELRSLRSDDTAVYYC AR
M99642         GFDPEDGETIYAQKFQG RVTMTEDTSTDTAYMELSSLRSEDTAVYYC AT
X62109         WINAGNTKYSQKFQG   RVTITRDTSASTAYMELSSLRSEDTAVYYC AR
X92343         IINPSGGSTSYAQKFQG RVTMTRDTSTSTVYMELSSLRSEDTAVYYC AR
Z12305         LVDPEDGETIYAEKFQG RVTITADTSTDTAYMELSSLRSEDTAVYYC AT
hVhvFW Cons    ----------------- RVTMTRDTSTSTAYMELSSLRSEDTAVYYC --
```

Figure 2a

```
                    10                  20                  30                  40                  50                  60
                    |                   |                   |                   |                   |                   |
hVkFW Cons  DIVMTQSPLSLPVTPGEPASISC --------------- WYLQKPGQSPQLLIY ------- 
m7F3  Vk    DVVMTQSPLSLPVSLGNQASISC RSSQSLVHSNGNTYLH WYLQKPGQSPKLLIY KVSNRFS
h7Vk        DVVMTQSPLSLPVTLGEPASISC RSSQSLVHSNGNTYLH WYLQKPGQSPQLLIY KVSNRFS
                    *                    CDR-L1                              CDR-L2

70                  80                  90                 100                 112
                    |                   |                   |                   |                   |
hVkFW Cons  GVPDRFSGSGSGTDFTLKISRVEAEDVGVYYC --------- FGQGTKLEIK
m7F3  Vk    GVPDRFSGSGSGTDESLKISRVEAEDLGVYFC SQSTLVPLT FGAGTKLELK
h7Vk        GVPDRFSGSGSGTDFTLKISRVEAEDVGVYFC SQSTLVPLT FGQGTKLEIK
                                       *        CDR-L3
```

Figure 3

```
                    10               20              30            40                50            60
RNOK203VL  DVVMTQTPLSLPVTLGQPASISC KSTKSLLNSDGFTYLG WCLQKPGQSPQLLIY LVSNRFS
m7E3  Vk   DVVMTQSPLSLPVSLGNQASISC RSSQSLVHSNGNTYLH WYLQKPGQSPKLLIY KVSNRFS
h7aVk      DVVMTQTPLSLPVTLGQPASISC RSSQSLVHSNGNTYLH WCLQKPGQSPQLLIY KVSNRFS
                                        CDR-L1                          CDR-L2

70              80              90             100           112
RNOK203VL  GVPDRFSGSGSGTDFTLKISRVEAEDVGVYYC FQSNYLPLT FGQGTKLEIK
m7E3  Vk   GVPDRFSGSGSGTDFSLKISRVEAEDLGVYFC SQSTLVPLT FGAGTKLELK
h7aVk      GVPDRFSGSGSGTDFTLKISRVEAEDVGVYYC SQSTLVPLT FGQGTKLEIK
                                             CDR-L3
```

Figure 4

```
              10         20         30            40         50         60
VLCD18-Q  DVVMTQSPLSLPVTLGQPASISC RSSQRLVHTNGNTYEH WFQQRPGQSPRLLIY KVSNRFF
m7F3 Vk   DVVMTQSPLSLPVSLGNQASISC RSSQSLVHSNGNTYLH WYLQKPGQSPKLLIY KVSNRFS
h7bVk     DVVMTQSPLSLPVTLGQPASISC RSSQSLVHSNGNTYLH WFQQRPGQSPRLLIY KVSNRFS
                                        CDR-L1                           CDR-L2

70         80         90           100        112
VLCD18-Q  GVPDRFSGSGSGTDFTLKISRVEAEDVGVYYC SQSTHVPRT FGGGTKLEIK
m7F3 Vk   GVPDRFSGSGSGTDFSLKISRVEAEDLGVYFC SQSTLVPLT FGAGTKLELK
h7bVk     GVPDRFSGSGSGTDFTLKISRVEAEDVGVYYC SQSTLVPLT FGGGTKLEIK
                                             CDR-L3
```

Figure 5

```
             10          20         30            40         50           60
m7F3  Vk   DVVMTQSPLSLPVSLGNQASISC RSSQSLVHSNGNTYLH WYLQKPGQSPKLLIY KVSNRFS
h7Vk       DVVMTQSPLSLPVTLGEPASISC RSSQSLVHSNGNTYLH WYLQKPGQSPQLLIY KVSNRFS
h7aVk      DVVMTQTPLSLPVTLGQPASISC RSSQSLVHSNGNTYLH WCLQKPGQSPQLLIY KVSNRFS
h7bVk      DVVMTQSPLSLPVTLGQPASISC RSSQSLVHSNGNTYLH WFQRPGQSPRLLIY  KVSNRFS
h7F3VkCons DVVMTQsPLSLPVTLGqPASISC RSSQSLVHSNGNTYLH WxLQkPGQSPqLLIY KVSNRFS
                                      CDR-L1            CDR-L2

70           80          90          100         112
m7F3  Vk   GVPDRFSGSGSGTDFSLKISRVEAEDLGVYYC SQSTLVPLT FGAGTKLELK
h7Vk       GVPDRFSGSGSGTDFTLKISRVEAEDVGVYEC SQSTLVPLT FGQGTKLEIK
h7aVk      GVPDRFSGSGSGTDFTLKISRVEAEDVGVYYC SQSTLVPLT FGQGTKLEIK
h7bVk      GVPDRFSGSGSGTDFTLKISRVEAEDVGVYYC SQSTLVPLT FGCGTKLEIK
h7F3VkCons GVPDRFSGSGSGTDFTLKISRVEAEDVGVYyC SQSTLVPLT FGqGTKLEIK
                                              CDR-L3
```

Figure 6

```
          1          20         30         40          50         61
hVhFW Cons QVQLVQSGAEVKKPGASVKVSCKAS ---------- WVRQAPGQGLEWMG ----------
m7F3  Vh   QVQLQQSGPELVKPGASVKISCKAS GYAFSNSWMN WVKQRPGKGLEWIG RIYPGDGDTKYN
h7Vh       QVQLVQSGAEVKKPGASVKISCKAS GYAFSNSWMN WVRQAPGKGLEWMG RIYPGDGDTKYN
                              *              CDR-H1         *          CDR-H2>

70              80              90        100        110        121
hVhFW Cons ----- RVTMTRDTSTSTAYMELSSLRSEDTAVYYC ---------- WGQGTTVTVSS
m7F3  Vh   GKFKG KATLTADKSSSTAYMQLSSLTSEDSAVYFC ARFLLISTVTAVDY WGQGTTLTVSS
h7Vh       GKFKG RVTITADESTSTAYMELSSLRSEDSAVYFC ARFLLISTVTAVDY WGQGTTVTVSS
           # * #           *                *        CDR-H3
```

Figure 7

```
                10                  20                  30                          40                   50          61
SGI-VH  VQLVQSGAEVKKPGASVKVSCKAS GYTFSSHWMH WVRQAPGQGLEWVG EENPSNGRTNYN
m7F3 Vh QVQLQQSGPELVKPGASVKISCKAS GYAFSNSWMN WVKQRPGKGLEWIG RIYPGDGDTKYN
h7aVh   QVQLVQSGAEVKKPGASVKVSCKAS GYAFSNSWMN WVKQAPGQGLEWIG RIYPGDGDTKYN
                                        *                   *                *
                                   CDR-H1                              CDR-H2>

70                  80                  90              100               110              121
SGI-VH  EKEKS RVTMTLDTSTNTAYMELSSLRSEDTAVYYC ASRDYDYDGRYFDY WGQGTLVTVSS
m7F3 Vh GKFKG KATLTADKSSSTAYMQLSSLTSEDSAVYFC ARFLLISTVTAVDY WGQGTTLTVSS
h7aVh   GKFKG KATMTADTSTSTAYMELSSLRSEDTAVYYC ARFLLISTVTAVDY WGQGTLVTVSS
              **      *        *
                                                                   CDR-H3
```

Figure 8

```
            10              20             30              40             50          61
HG3    QVQLVQSGAEVKKPGASVKVSCKAS GYTFNSYYMH WVRQAPGQGLEWMG IINPSGGSTSYA
m7F3 Vh QVQLQQSGPELVKPGASVKISCKAS GYAFSNSWMN WVKQRPGKGLEWIG RIYPGDGDTKYN
h7bVh  QVQLVQSGAEVKKPGASVKVSCKAS GYAFSNSWMN WVRQAPGQGLEWMG RIYPGDGDTKYN
                                   CDR-H1                     CDR-H2>

70              80              90          100         110           121
HG3    QKFQG RVTMTRDTSTSTVYMELSSLRSEDTAVYYC ARY------FDY WGQGTLVTVSS
m7F3 Vh GKEKG KATLTADKSSTAYMQLSSLTSEDSAVYFC AREFLLISTVTAVDY WGQGTTLTVSS
h7bVh  GKEKG RVTMTADTSTSTVYMELSSLRSEDTAVYYC AREFLLISTVTAVDY WGQGTLVTVSS
                              *                CDR-H3
```

Figure 9

```
                  10                  20                    30              40                    50              61
m7F3 Vh    QVQLQQSGPELVKPGASVKISCKAS GYAFSNSWMN WVKQRPGKGLEWIG RIYPGDGDTKYN
h7Vh       QVQLVQSGAEVKKPGASVKISCKAS GYAFSNSWMN WVRQAPGKGLEWMG RIYPGDGDTKYN
h7aVh      QVQLVQSGAEVKKPGASVKVSCKAS GYAFSNSWMN WVKQAPGQGLEWIG RIYPGDGDTKYN
h7bVh      QVQLVQSGAEVKKPGASVKVSCKAS GYAFSNSWMN WVRQAPGQGLEWMG RIYPGDGDTKYN
h7F3VhCons QVQLVQSGAEVKKPGASVKvSCKAS GYAFSNSWMN WVrQAPGqGLEWmG RIYPGDGDTKYN
                                      CDR-H1                                  CDR-H2>

70              80                90                 100            110            121
m7F3 Vh    GKFKG KATLTADKSSSTAYMQLSSLTSEDSAVYFC ARFLLISTVTAVDY WGQGTTLTVSS
h7Vh       GKFKG RVTITADESTSTAYMELSSLRSEDSAVYFC ARFLLISTVTAVDY WGQGTTVTVSS
h7aVh      GKFKG RVTKATMTADTSTSTAYMELSSLRSEDTAVYYC ARFLLISTVTAVDY WGQGTLVTVSS
h7bVh      GKFKG RVTMTADTSTSTVYMELSSLRSEDTAVYYC ARFLLISTVTAVDY WGQGTLVTVSS
h7F3VhCons       rvTmTAdtStSTaYMELSSLRSEDtAVYyC ARFLLISTVTAVDY WGQGTlVTVSS
                                                                CDR-H3
```

Figure 10

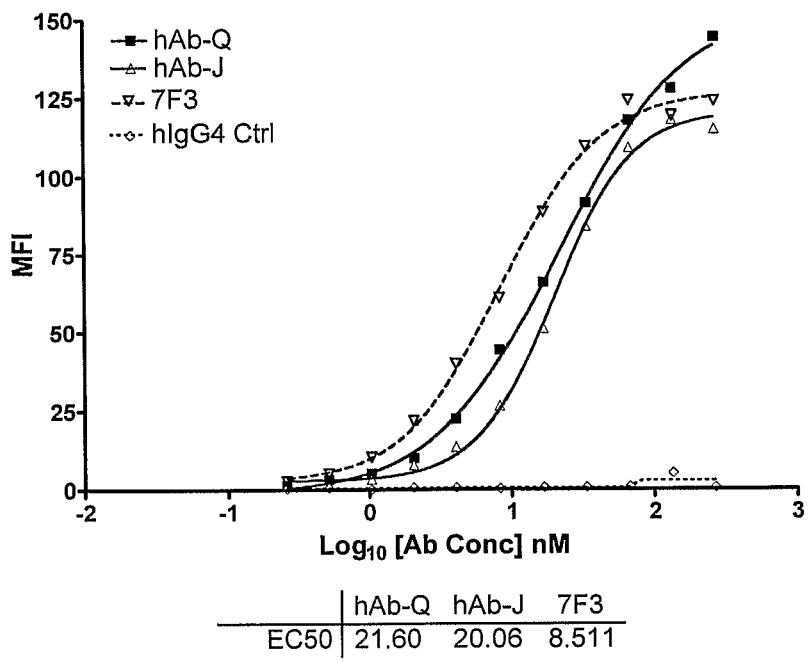
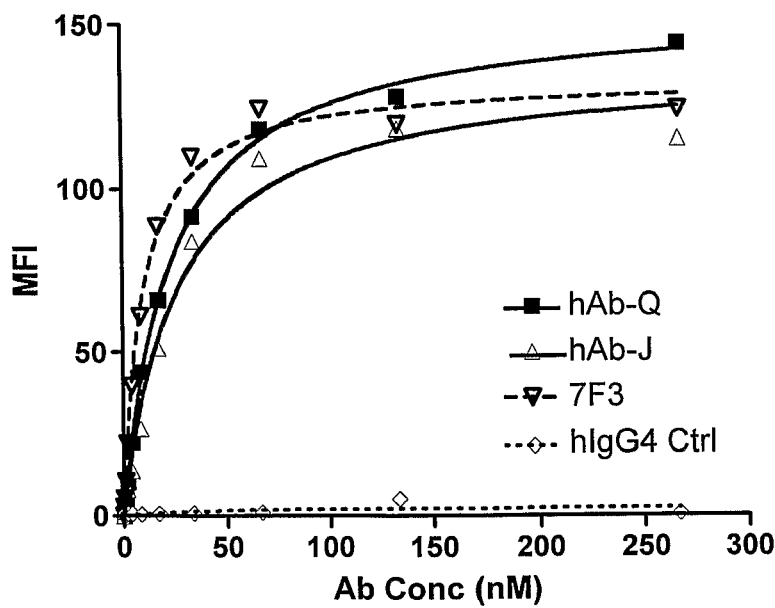
Figure 13

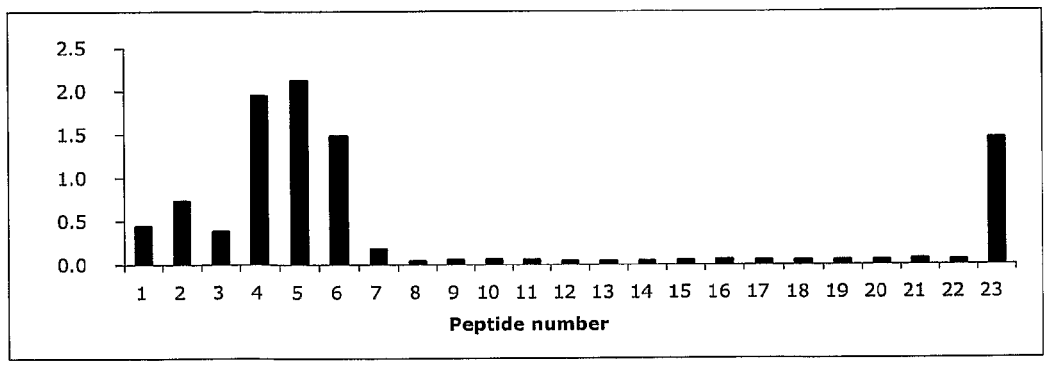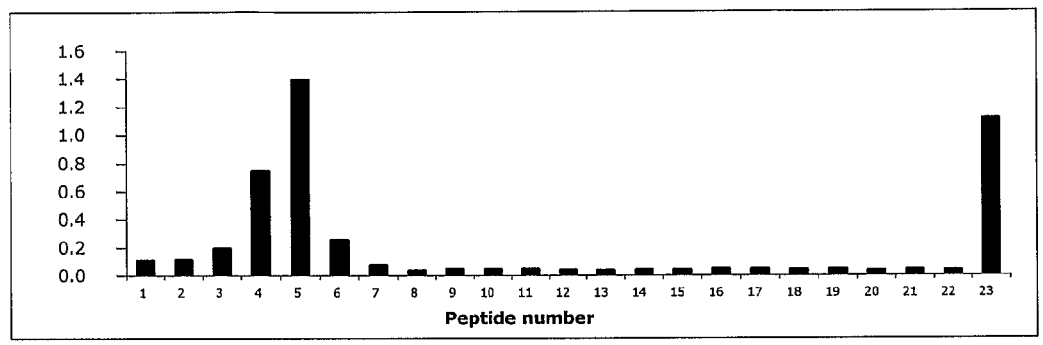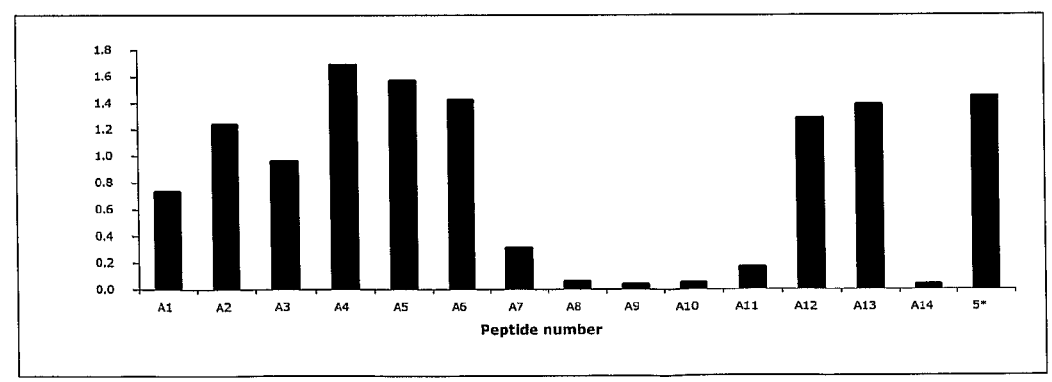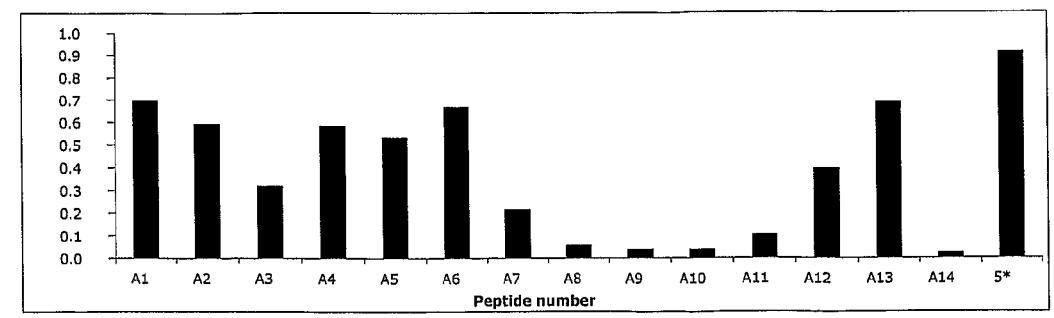
Figure 14

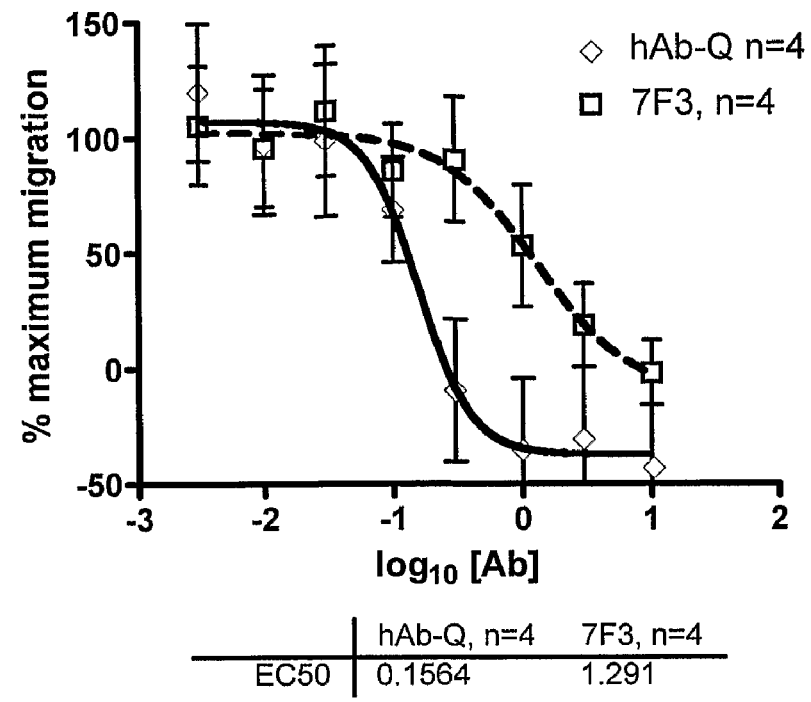
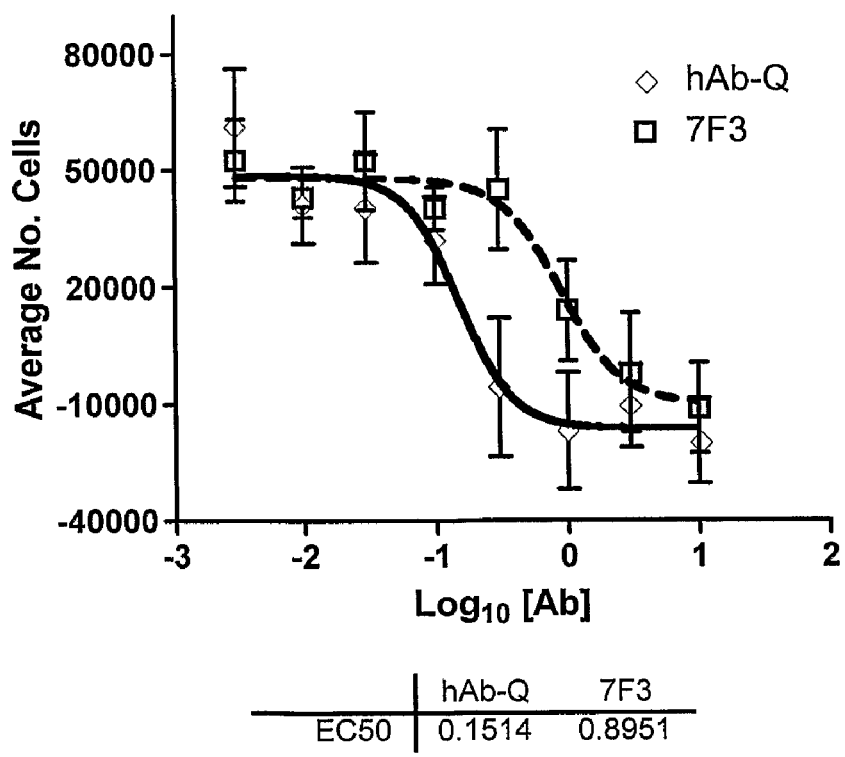
Figure 17

- ■ % Bound A (pre-migration), n=4
- △ % Bound BL (lower,chamber post-migration), n=4
- ○ % Free C (pre-migration) n=1
- ▽ % Free D (lower chamber, post-migration) n=1

- ■ % Bound Receptor A (pre-migration), n=4
- △ % Bound Receptor BL(post-migration), n=4
- ○ % Inhibition of Migration, n=4

A
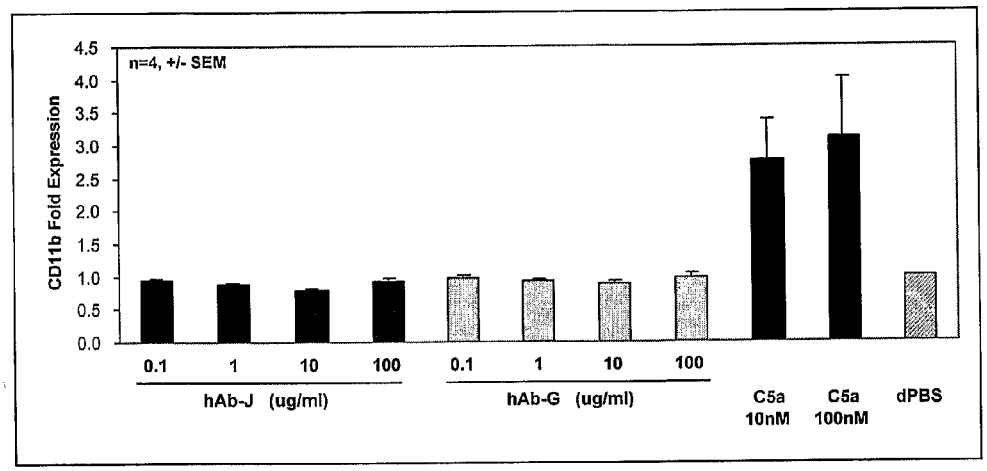
B
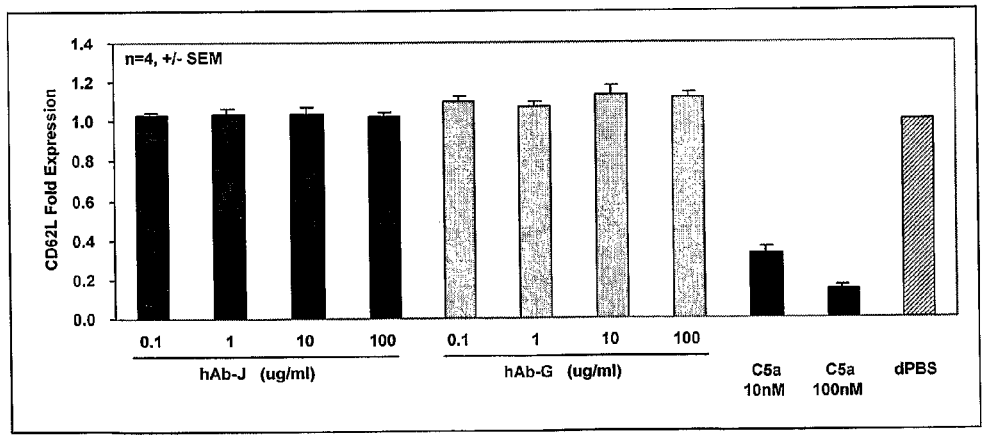
Figure 25

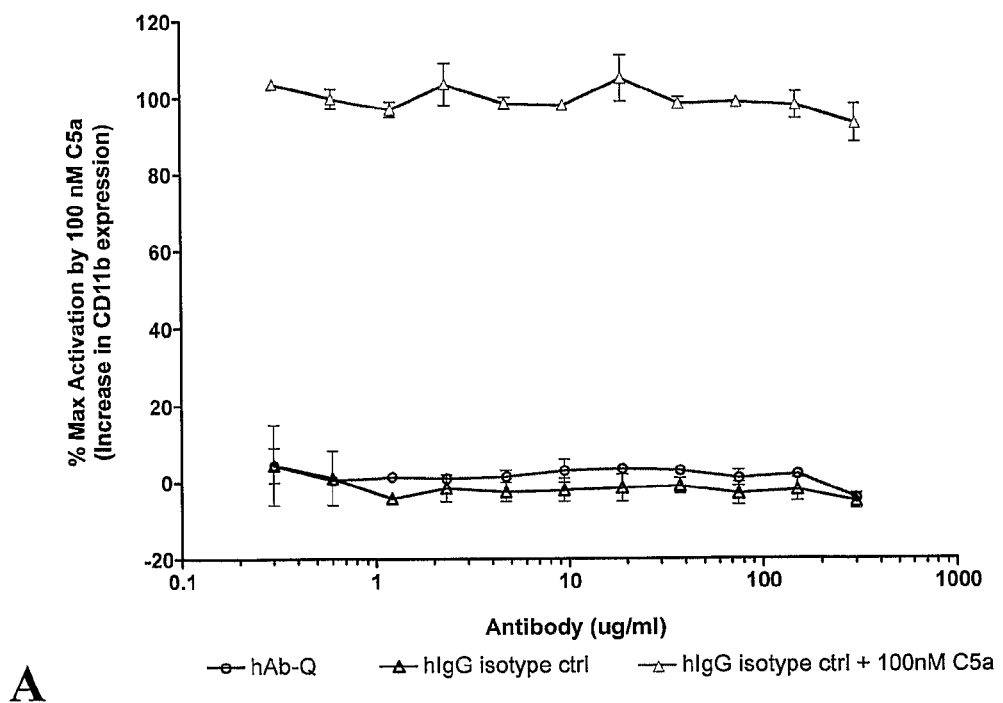
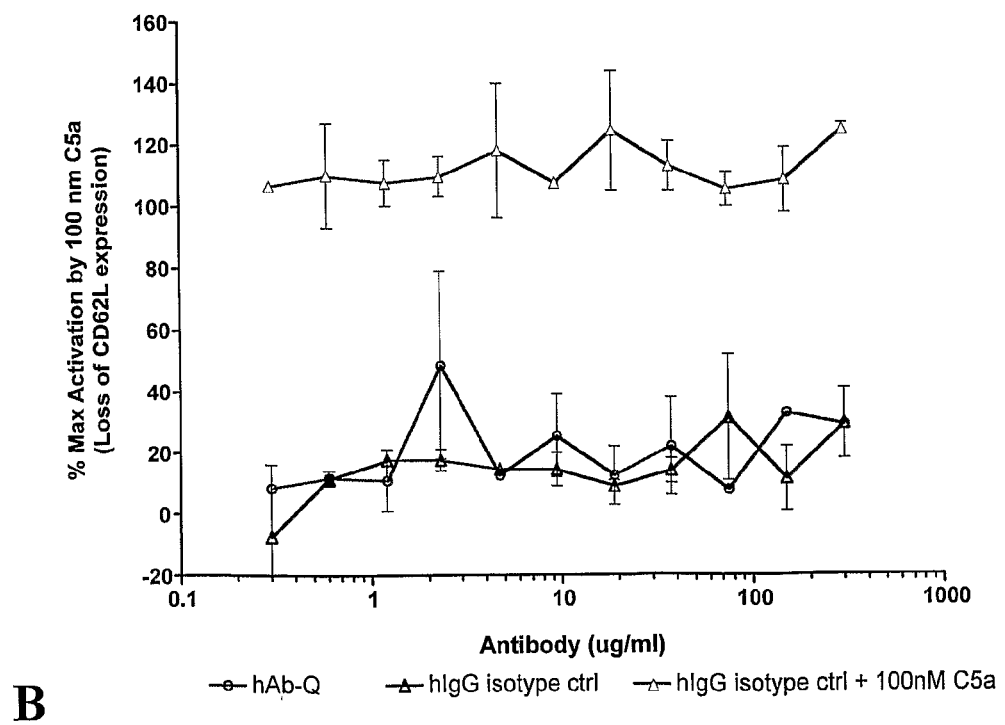
Figure 26

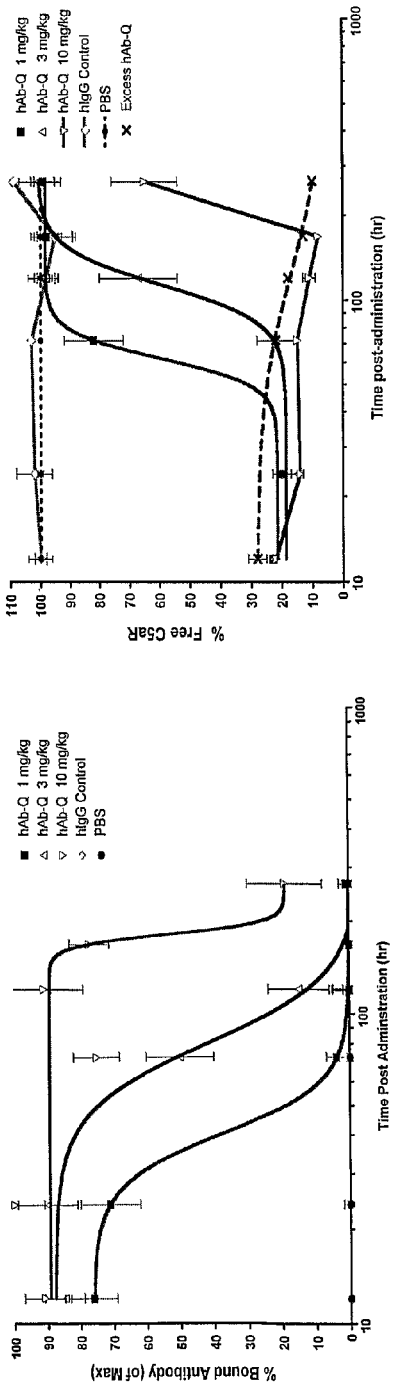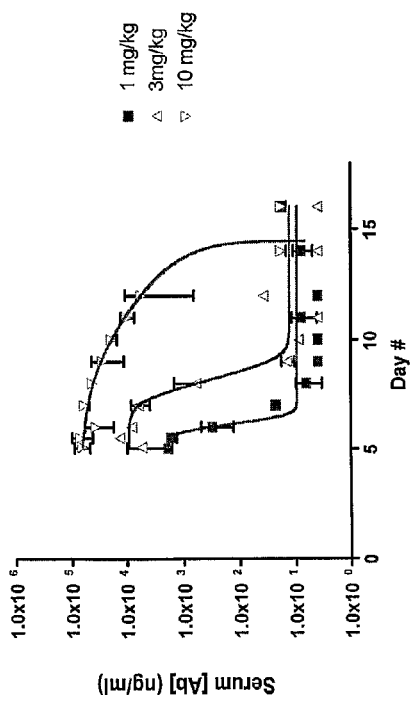
Figure 38
Figure 37
Figure 39

SEQUENCE LISTING

```
<160> NUMBER OF SEQ ID NOS: 59

<210> SEQ ID NO 1
<211> LENGTH: 112
<212> TYPE: PRT
<213> ORGANISM: Mus musculus

<400> SEQUENCE: 1

Asp Val Val Met Thr Gln Ser Pro Leu Ser Leu Pro Val Ser Leu Gly
 1               5                  10                  15

Asn Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Ser Leu Lys Ile
 65                  70                  75                  80

Ser Arg Val Glu Ala Glu Asp Leu Gly Val Tyr Phe Cys Ser Gln Ser
                 85                  90                  95

Thr Leu Val Pro Leu Thr Phe Gly Ala Gly Thr Lys Leu Glu Leu Lys
            100                 105                 110

<210> SEQ ID NO 2
<211> LENGTH: 121
<212> TYPE: PRT
<213> ORGANISM: Mus musculus

<400> SEQUENCE: 2

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Ser Asn Ser
             20                  25                  30

Trp Met Asn Trp Val Lys Gln Arg Pro Gly Lys Gly Leu Glu Trp Ile
         35                  40                  45

Gly Arg Ile Tyr Pro Gly Asp Gly Asp Thr Lys Tyr Asn Gly Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Phe Leu Leu Ile Ser Thr Val Thr Ala Val Asp Tyr Trp Gly
            100                 105                 110
```

Gln Gly Thr Thr Leu Thr Val Ser Ser
        115                 120

<210> SEQ ID NO 3
<211> LENGTH: 336
<212> TYPE: DNA
<213> ORGANISM: Mus musculus

<400> SEQUENCE: 3
gatgttgtga tgacccaatc tccactctcc ctgcctgtca gtcttggaaa tcaagcctcc     60
atctcttgca gatctagtca gagccttgta cacagtaatg aaacaccta tttacattgg    120 tacctgcaga agccaggcca gtctccaaag ctcctgatct acaaagtttc caaccgattt    180
tctggggtcc cagacaggtt cagtggcagt ggatcaggga cagatttctc actcaagatc    240
agcagagtgg aggctgagga tctgggagtt tatttctgct ctcaaagtac acttgttccg    300
ctcacgttcg gtgctgggac caagctggaa ctgaaa                              336

<210> SEQ ID NO 4
<211> LENGTH: 363
<212> TYPE: DNA
<213> ORGANISM: Mus musculus

<400> SEQUENCE: 4
caggttcagc tgcagcagtc tggacctgag ctggtgaagc ctggggcctc agtgaagatt     60
tcctgcaagg cttctggcta cgcattcagt aactcctgga tgaactgggt gaagcagagg    120
cctggaaagg gtcttgagtg gattggacgg atttatcctg agatggaga tactaagtac    180 aatgggaagt tcaagggcaa ggccacactg actgcagaca atcctccag cacagcctac    240 atgcaactca gcagcctgac atctgaggac tctgcggtct atttctgtgc aagattccta    300
cttattagta cggtaacagc cgttgactac tggggccaag gcaccactct cacagtctcc    360
tca                                                                  363

<210> SEQ ID NO 5
<211> LENGTH: 112
<212> TYPE: PRT
<213> ORGANISM: Homo sapiens

<400> SEQUENCE: 5

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Ser Trp Thr Phe Gly Gln Gly Thr Lys Val Glu Ile Lys
            100                 105                 110

<210> SEQ ID NO 6
<211> LENGTH: 112
<212> TYPE: PRT
<213> ORGANISM: Homo sapiens -continued

<400> SEQUENCE: 6

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gln Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Gln Thr Phe Gly Gln Gly Thr Lys Val Glu Ile Lys
            100                 105                 110

<210> SEQ ID NO 7
<211> LENGTH: 112
<212> TYPE: PRT
<213> ORGANISM: Homo sapiens

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Phe Asp Tyr Leu Asn Trp Tyr Leu Gln Lys Pro Gly Gln Ser
        35                  40                  45

Pro Glx Leu Leu Ile Tyr Ala Leu Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glx Ala
                85                  90                  95

Leu Gln Ala Pro Ile Thr Phe Gly Gln Gly Thr Arg Leu Glu Ile Lys
            100                 105                 110

<210> SEQ ID NO 8
<211> LENGTH: 112
<212> TYPE: PRT
<213> ORGANISM: Homo sapiens

<400> SEQUENCE: 8

Asp Val Val Met Thr Gln Ser Pro Leu Phe Leu Pro Val Thr Leu Gly
1               5                   10                  15

Glu Pro Ala Ser Ile Gln Cys Arg Ser Ser Gln Ser Leu Val Tyr Arg
            20                  25                  30

Asx Gly Asx Thr Tyr Leu Asx Trp Tyr Leu Gln Lys Pro Gly Gln Ser
        35                  40                  45

Pro Glu Leu Leu Ile Tyr Leu Ser Ser Tyr Arg Asp Ser Gly Val Pro
    50                  55                  60

Asp Arg Phe Ser Asp Ser Gly Ser Gly Thr Asp Phe Thr Leu Lys Ile
65                  70                  75                  80

Thr Arg Val Gln Ala Glu Asp Val Gly Val Tyr Tyr Cys Met Gln Ala
                85                  90                  95

Thr Glx Ser Pro Tyr Thr Phe Gly Gln Gly Thr Lys Leu Glx Ile Lys
            100                 105                 110

<210> SEQ ID NO 9
<211> LENGTH: 113
<212> TYPE: PRT
<213> ORGANISM: Homo sapiens

<400> SEQUENCE: 9

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Gly Asp Gly Asn Thr Tyr Leu Asn Trp Tyr Leu Gln Lys Ala Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Gln Ala Glu Asp Val Gly Val Tyr Tyr Cys Met Gln
                85                  90                  95

Arg Leu Glu Ile Pro Tyr Thr Phe Gly Gln Gly Thr Lys Leu Glu Ile
            100                 105                 110

Arg

<210> SEQ ID NO 10
<211> LENGTH: 100
<212> TYPE: PRT
<213> ORGANISM: Homo sapiens

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 11
<211> LENGTH: 100
<212> TYPE: PRT
<213> ORGANISM: Homo sapiens

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

-continued

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 12
<211> LENGTH: 100
<212> TYPE: PRT
<213> ORGANISM: Homo sapiens

<400> SEQUENCE: 12

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Ser
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 13
<211> LENGTH: 100
<212> TYPE: PRT
<213> ORGANISM: Homo sapiens

<400> SEQUENCE: 13

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 14
<211> LENGTH: 113
<212> TYPE: PRT
<213> ORGANISM: Artificial Sequence
<220> FEATURE:
<223> OTHER INFORMATION: Consensus of human light chain variable
      sequences
<220> FEATURE:
<221> NAME/KEY: VARIANT
<222> LOCATION: (24)...(40)
<223> OTHER INFORMATION: Xaa = different amino acids corresponding to CDR-L1. CDR-L1 could be missing 1 Xaa residue.
<220> FEATURE:
<221> NAME/KEY: VARIANT
<222> LOCATION: (56)...(62)
<223> OTHER INFORMATION: Xaa = different amino acids corresponding to
      CDR-L2
<220> FEATURE:
<221> NAME/KEY: VARIANT
<222> LOCATION: (95)...(103)
<223> OTHER INFORMATION: Xaa = different amino acids corresponding to
      CDR-L3. CDR-L3 could be missing 2 Xaa residues.

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Xaa Xaa Xaa Xaa Xaa Xaa Xaa Xaa
            20                  25                  30

Xaa Xaa Xaa Xaa Xaa Xaa Xaa Trp Tyr Leu Gln Lys Pro Gly Gln
        35                  40                  45

Ser Pro Gln Leu Leu Ile Tyr Xaa Xaa Xaa Xaa Xaa Xaa Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Xaa Xaa
                85                  90                  95

Xaa Xaa Xaa Xaa Xaa Xaa Xaa Phe Gly Gln Gly Thr Lys Leu Glu Ile
            100                 105                 110

Lys

<210> SEQ ID NO 15
<211> LENGTH: 98
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly

<210> SEQ ID NO 16
<211> LENGTH: 98
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met

```
                    35                  40                  45
Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 17
<211> LENGTH: 98
<212> TYPE: PRT
<213> ORGANISM: Homo sapiens

<400> SEQUENCE: 17

Gln Thr Gln Leu Val Gln Ser Gly Ala Glu Val Arg Lys Pro Gly Ala
 1               5                  10                  15

Ser Val Arg Val Ser Cys Lys Ala Ser Gly Tyr Thr Phe Ile Asp Ser
                 20                  25                  30

Tyr Ile His Trp Ile Arg Gln Ala Pro Gly His Gly Leu Glu Trp Val
             35                  40                  45

Gly Trp Ile Asn Pro Asn Ser Gly Gly Thr Asn Tyr Ala Pro Arg Phe
 50                  55                  60

Gln Gly Arg Val Thr Met Thr Arg Asp Ala Ser Phe Ser Thr Ala Tyr
 65                  70                  75                  80

Met Asp Leu Arg Ser Leu Arg Ser Asp Asp Ser Ala Val Phe Tyr Cys
                 85                  90                  95

Ala Lys

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
                 85                  90                  95

Ala Arg

<210> SEQ ID NO 19
<211> LENGTH: 98
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
 1               5                  10                  15
```

```
Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg

<210> SEQ ID NO 20
<211> LENGTH: 98
<212> TYPE: PRT
<213> ORGANISM: Homo sapiens

<400> SEQUENCE: 20

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr

<210> SEQ ID NO 21
<211> LENGTH: 98
<212> TYPE: PRT
<213> ORGANISM: Homo sapiens

<400> SEQUENCE: 21

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 22
<211> LENGTH: 98
<212> TYPE: PRT
<213> ORGANISM: Homo sapiens

<400> SEQUENCE: 22
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 23
<211> LENGTH: 98
<212> TYPE: PRT
<213> ORGANISM: Homo sapiens

<400> SEQUENCE: 23

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 24
<211> LENGTH: 98
<212> TYPE: PRT
<213> ORGANISM: Artificial Sequence
<220> FEATURE:
<223> OTHER INFORMATION: Consensus of human heavy chain variable
      sequences
<220> FEATURE:
<221> NAME/KEY: VARIANT
<222> LOCATION: (26)...(35)
<223> OTHER INFORMATION: Xaa = different amino acids corresponding to
      CDR-H1
<220> FEATURE:
<221> NAME/KEY: VARIANT
<222> LOCATION: (50)...(66)
<223> OTHER INFORMATION: Xaa = different amino acids corresponding to
      CDR-H2
<220> FEATURE:
<221> NAME/KEY: VARIANT
<222> LOCATION: 97, 98
<223> OTHER INFORMATION: Xaa = different amino acids corresponding to
      CDR-H3

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Xaa Xaa Xaa Xaa Xaa Xaa Xaa
            20                  25                  30
```

```
Xaa Xaa Xaa Trp Val Arg Gln Ala Pro Gly Gln Gly Leu Glu Trp Met
        35                  40                  45

Gly Xaa Xaa Xaa Xaa Xaa Xaa Xaa Xaa Xaa Xaa Xaa Xaa
 50                  55                  60

Xaa Xaa Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Xaa Xaa

<210> SEQ ID NO 25
<211> LENGTH: 13
<212> TYPE: PRT
<213> ORGANISM: Homo sapiens

<400> SEQUENCE: 25

Asp Val Trp Gly Gln Gly Thr Thr Val Thr Val Ser Ser
 1               5                  10

<210> SEQ ID NO 26
<211> LENGTH: 13
<212> TYPE: PRT
<213> ORGANISM: Homo sapiens

<400> SEQUENCE: 26

Asp Val Trp Gly Gln Gly Thr Thr Val Thr Val Ser Ser
 1               5                  10

<210> SEQ ID NO 27
<211> LENGTH: 13
<212> TYPE: PRT
<213> ORGANISM: Homo sapiens

<400> SEQUENCE: 27

Asp Tyr Trp Gly Glx Gly Thr Leu Val Thr Ile Ser Ser
 1               5                  10

<210> SEQ ID NO 28
<211> LENGTH: 13
<212> TYPE: PRT
<213> ORGANISM: Homo sapiens

<400> SEQUENCE: 28

Asp Tyr Trp Gly Gln Gly Thr Pro Val Thr Val Ser Ser
 1               5                  10

<210> SEQ ID NO 29
<211> LENGTH: 13
<212> TYPE: PRT
<213> ORGANISM: Homo sapiens

<400> SEQUENCE: 29

Asp Tyr Trp Gly Gln Gly Thr Leu Val Thr Val Ser Thr
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Consensus of human heavy chain joining
      sequences
<220> FEATURE:
<221> NAME/KEY: VARIANT
```

```
<222> LOCATION: 1, 2
<223> OTHER INFORMATION: Xaa = different amino acids corresponding to
      CDR-H3

<400> SEQUENCE: 30

Xaa Xaa Trp Gly Gln Gly Thr Thr Val Thr Val Ser Ser
1               5                   10

<210> SEQ ID NO 31
<211> LENGTH: 112
<212> TYPE: PRT
<213> ORGANISM: Artificial Sequence
<220> FEATURE:
<223> OTHER INFORMATION: Humanized antibody segment

<400> SEQUENCE: 31

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr Leu Val Pro Leu Thr Phe Gly Gln Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Humanized antibody segment

<400> SEQUENCE: 32

Asp Val Val Met Thr Gln Thr Pro Leu Ser Leu Pro Val Thr Leu Gly
1               5                   10                  15

Gln Pro Ala Ser Ile Ser Cys Arg Ser Gln Ser Leu Val His Ser
            20                  25                  30

Asn Gly Asn Thr Tyr Leu His Trp Cys Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Leu Thr Phe Gly Gln Gly Thr Lys Leu Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Humanized antibody segment

<400> SEQUENCE: 33
```

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95

Thr Leu Val Pro Leu Thr Phe Gly Gly Gly Thr Lys Leu Glu Ile Lys
            100                 105                 110
```

<210> SEQ ID NO 34
<211> LENGTH: 121
<212> TYPE: PRT
<213> ORGANISM: Artificial Sequence
<220> FEATURE:
<223> OTHER INFORMATION: Humanized antibody segment

<400> SEQUENCE: 34

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Ser Asn Ser
            20                  25                  30

Trp Met Asn Trp Val Arg Gln Ala Pro Gly Lys Gly Leu Glu Trp Met
        35                  40                  45

Gly Arg Ile Tyr Pro Gly Asp Gly Asp Thr Lys Tyr Asn Gly Lys Phe
    50                  55                  60

Lys Gly Arg Val Thr Ile Thr Ala Asp Glu Ser Thr Ser Thr Ala Tyr
65              70                  75                  80

Met Glu Leu Ser Ser Leu Arg Ser Glu Asp Ser Ala Val Tyr Phe Cys
                85                  90                  95

Ala Arg Phe Leu Leu Ile Ser Thr Val Thr Ala Val Asp Tyr Trp Gly
            100                 105                 110

Gln Gly Thr Thr Val Thr Val Ser Ser
        115                 120
```

<210> SEQ ID NO 35
<211> LENGTH: 121
<212> TYPE: PRT
<213> ORGANISM: Artificial Sequence
<220> FEATURE:
<223> OTHER INFORMATION: Humanized antibody segment

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Ser
            20                  25                  30

Trp Met Asn Trp Val Lys Gln Ala Pro Gly Gln Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Met Thr Ala Asp Thr Ser Thr Ser Thr Ala Tyr
65              70                  75                  80
```

```
Met Glu Leu Ser Ser Leu Arg Ser Glu Asp Thr Ala Val Tyr Tyr Cys
                85                  90                  95

Ala Arg Phe Leu Leu Ile Ser Thr Val Thr Ala Val Asp Tyr Trp Gly
            100                 105                 110

Gln Gly Thr Leu Val Thr Val Ser Ser
        115                 120

<210> SEQ ID NO 36
<211> LENGTH: 121
<212> TYPE: PRT
<213> ORGANISM: Artificial Sequence
<220> FEATURE:
<223> OTHER INFORMATION: Humanized antibody segment

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Lys Tyr Asn Gly Lys Phe
    50                  55                  60

Lys Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Phe Leu Leu Ile Ser Thr Val Thr Ala Val Asp Tyr Trp Gly
            100                 105                 110

Gln Gly Thr Leu Val Thr Val Ser Ser
        115                 120

<210> SEQ ID NO 37
<211> LENGTH: 350
<212> TYPE: PRT
<213> ORGANISM: Homo sapiens

<400> SEQUENCE: 37

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
            35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
            115                 120                 125

Thr Ile Ser Ala Asp Arg Phe Leu Leu Val Phe Lys Pro Ile Trp Cys
        130                 135                 140

Gln Asn Phe Arg Gly Ala Gly Leu Ala Trp Ile Ala Cys Ala Val Ala
```

```
                145                 150                 155                 160
Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
                180                 185                 190

Ser His Asp Lys Arg Glu Arg Ala Val Ala Ile Val Arg Leu Val
                195                 200                 205

Leu Gly Phe Leu Trp Pro Leu Leu Thr Leu Thr Ile Cys Tyr Thr Phe
                210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
                260                 265                 270

Pro Thr Phe Leu Leu Leu Asn Lys Leu Asp Ser Leu Cys Val Ser Phe
                275                 280                 285

Ala Tyr Ile Asn Cys Cys Ile Asn Pro Ile Ile Tyr Val Val Ala Gly
                290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Gly Ser Lys Ser Phe Thr
                325                 330                 335

Arg Ser Thr Val Asp Thr Met Ala Gln Lys Thr Gln Ala Val
                340                 345                 350

<210> SEQ ID NO 38
<211> LENGTH: 6
<212> TYPE: PRT
<213> ORGANISM: Artificial Sequence
<220> FEATURE:
<223> OTHER INFORMATION: C5aR epitope bound by antibodies of the
      invention

<400> SEQUENCE: 38

Glu Glu Tyr Phe Pro Pro
1               5

<210> SEQ ID NO 39
<211> LENGTH: 121
<212> TYPE: PRT
<213> ORGANISM: Artificial Sequence
<220> FEATURE:
<223> OTHER INFORMATION: Consensus sequence of human heavy chain
      variable regions of the invention.

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Lys Tyr Asn Gly Lys Phe
        50                  55                  60

Lys Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Phe Leu Leu Ile Ser Thr Val Thr Ala Val Asp Tyr Trp Gly
            100                 105                 110

Gln Gly Thr Leu Val Thr Val Ser Ser
            115                 120

<210> SEQ ID NO 40
<211> LENGTH: 106
<212> TYPE: PRT
<213> ORGANISM: Homo sapiens

<400> SEQUENCE: 40

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 41
<211> LENGTH: 107
<212> TYPE: PRT
<213> ORGANISM: Homo sapiens

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                    35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 43
<211> LENGTH: 327
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
 65                  70                  75                  80
Tyr Thr Cys Asn Val Asp His Lys Pro Ser Asn Thr Lys Val Asp Lys
```

```
                    85                  90                  95
Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 44
<211> LENGTH: 330
<212> TYPE: PRT
<213> ORGANISM: Homo sapiens

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 327
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
                       180                 185                 190
Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 112
<212> TYPE: PRT
<213> ORGANISM: Artificial Sequence
<220> FEATURE:
<223> OTHER INFORMATION: Humanized RNOK203VL sequence

<400> SEQUENCE: 46

Asp Val Val Met Thr Gln Thr Pro Leu Ser Leu Pro Val Thr Leu Gly
1               5                   10                  15

Gln Pro Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: KV2F-HUMAN derived VLCD18-Q sequence

<400> SEQUENCE: 47

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Arg Leu Val His Thr
            20                  25                  30

Asn Gly Asn Thr Tyr Phe His Trp Phe Gln Gln Arg Pro Gly Gln Ser
        35                  40                  45

Pro Arg Leu Leu Ile Tyr Lys Val Ser Asn Arg Phe Phe Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Val Pro Arg Thr Phe Gly Gly Gly Thr Lys Leu Glu Ile Lys
                100                 105                 110

<210> SEQ ID NO 48
<211> LENGTH: 112
<212> TYPE: PRT
<213> ORGANISM: Artificial Sequence
<220> FEATURE:
<223> OTHER INFORMATION: Consensus sequence h7F3VkCons
<220> FEATURE:
<221> NAME/KEY: VARIANT
<222> LOCATION: (41)..(41)
<223> OTHER INFORMATION: Xaa = Tyr, Cys or Phe

<400> SEQUENCE: 48

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
                20                  25                  30

Asn Gly Asn Thr Tyr Leu His Trp Xaa Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr Leu Val Pro Leu Thr Phe Gly Gln Gly Thr Lys Leu Glu Ile Lys
                100                 105                 110

<210> SEQ ID NO 49
<211> LENGTH: 121
<212> TYPE: PRT
<213> ORGANISM: Artificial Sequence
<220> FEATURE:
<223> OTHER INFORMATION: Consensus of human heavy chain variable
      sequences
<220> FEATURE:
<221> NAME/KEY: VARIANT
<222> LOCATION: (26)...(35)
<223> OTHER INFORMATION: Xaa = different amino acids corresponding to
      CDR-H1
<220> FEATURE:
<221> NAME/KEY: VARIANT
<222> LOCATION: (50)...(66)
<223> OTHER INFORMATION: Xaa = different amino acids corresponding to
      CDR-H2
<220> FEATURE:
<221> NAME/KEY: VARIANT
<222> LOCATION: (97)...(110)
<223> OTHER INFORMATION: Xaa = different amino acids corresponding to
      CDR-H3

<400> SEQUENCE: 49

Gln Val Gln Leu Val Gln Ser Gly Ala Glu Val Lys Lys Pro Gly Ala
 1               5                  10                  15

Ser Val Lys Val Ser Cys Lys Ala Ser Xaa Xaa Xaa Xaa Xaa Xaa Xaa
                20                  25                  30

Xaa Xaa Xaa Trp Val Arg Gln Ala Pro Gly Gln Gly Leu Glu Trp Met
            35                  40                  45
```

```
Gly Xaa Xaa Xaa Xaa Xaa Xaa Xaa Xaa Xaa Xaa Xaa
    50                  55                  60

Xaa Xaa Arg Val Thr Met Thr Arg Asp Thr Ser Thr Ser Thr Ala Tyr
65              70                  75                  80

Met Glu Leu Ser Ser Leu Arg Ser Glu Asp Thr Ala Val Tyr Tyr Cys
                85                  90                  95

Xaa Xaa Xaa Xaa Xaa Xaa Xaa Xaa Xaa Xaa Xaa Xaa Trp Gly
            100                 105                 110

Gln Gly Thr Thr Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: Human SGI-VH sequence

<400> SEQUENCE: 50

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Ser Ser His Trp
            20                  25                  30

Met His Trp Val Arg Gln Ala Pro Gly Gln Gly Leu Glu Trp Val Gly
        35                  40                  45

Glu Phe Asn Pro Ser Asn Gly Arg Thr Asn Tyr Asn Glu Lys Phe Lys
    50                  55                  60

Ser Arg Val Thr Met Thr Leu Asp Thr Ser Asn Thr Ala Tyr Met
65              70                  75                  80

Glu Leu Ser Ser Leu Arg Ser Glu Asp Thr Ala Val Tyr Tyr Cys Ala
                85                  90                  95

Ser Arg Asp Tyr Asp Tyr Asp Gly Arg Tyr Phe Asp Tyr Trp Gly Gln
            100                 105                 110

Gly Thr Leu Val Thr Val Ser Ser
        115                 120

<210> SEQ ID NO 51
<211> LENGTH: 113
<212> TYPE: PRT
<213> ORGANISM: Artificial Sequence
<220> FEATURE:
<223> OTHER INFORMATION: Human germline HG3 sequence

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110
```

Ser

<210> SEQ ID NO 52
<211> LENGTH: 336
<212> TYPE: DNA
<213> ORGANISM: Artificial Sequence
<220> FEATURE:
<223> OTHER INFORMATION: Nucleic acid encoding humanized antibody
      segment

<400> SEQUENCE: 52
gatgttgtga tgacccaatc tccactctcc ctgcctgtca ctcttggaga gccagcctcc      60
atctcttgca gatctagtca gagccttgtc cacagtaatg gaaacaccta tttgcattgg    120
tacctgcaga agccaggcca gtctccacag ctcctgatct acaaagtttc caaccgcttt    180
tctggggtcc cagacaggtt cagtggcagt ggatcaggga cagatttcac actcaagatc    240
agcagagtgg aggctgagga tgtgggagtt tatttctgct ctcaaagtac acttgttcct    300
ctcaccttcg gtcaggggac caagctggaa atcaaa                              336

<210> SEQ ID NO 53
<211> LENGTH: 336
<212> TYPE: DNA
<213> ORGANISM: Artificial Sequence
<220> FEATURE:
<223> OTHER INFORMATION: Nucleic acid encoding humanized antibody
      segment

<400> SEQUENCE: 53
gatgttgtga tgacccaaac tccactctcc ctgcctgtca ctcttggaca gccagcctcc      60
atctcttgca gatctagtca gagccttgtc cacagtaatg gaaacaccta tttgcattgg    120
tgcctgcaga agccaggcca gtctccacag ctcctgatct acaaagtttc caaccgcttt    180
tctggggtcc cagacaggtt cagtggcagt ggatcaggga cagatttcac actcaagatc    240
agcagagtgg aggctgagga tgtgggagtt tattactgct ctcaaagtac acttgttcct    300
ctcaccttcg gtcaggggac caagctggaa atcaaa                              336

<210> SEQ ID NO 54
<211> LENGTH: 336
<212> TYPE: DNA
<213> ORGANISM: Artificial Sequence
<220> FEATURE:
<223> OTHER INFORMATION: Nucleic acid encoding humanized antibody
      segment

<400> SEQUENCE: 54
gatgttgtga tgacccaatc tccactctcc ctgcctgtca ctcttggaca gccagcctcc      60
atctcttgca gatctagtca gagccttgtc cacagtaatg gaaacaccta tttgcattgg    120
ttccagcagc ggccaggcca gtctccacgg ctcctgatct acaaagtttc caaccgcttt    180
tctggggtcc cagacaggtt cagtggcagt ggatcaggga cagatttcac actcaagatc    240
agcagagtgg aggctgagga tgtgggagtt tattactgct ctcaaagtac acttgttcct    300
ctcaccttcg gtggagggac caagctggaa atcaaa                              336

<210> SEQ ID NO 55
<211> LENGTH: 363
<212> TYPE: DNA
<213> ORGANISM: Artificial Sequence
<220> FEATURE:
<223> OTHER INFORMATION: Nucleic acid encoding humanized antibody
      segment

<400> SEQUENCE: 55

```
caggttcagc tggtgcagtc tggagctgag gtgaagaagc ctggggcctc agtgaagatt      60
tcctgcaagg cttctggcta cgcattcagt aactcctgga tgaactgggt gaggcaggct     120
cctggaaagg gtctagagtg gatgggacgg atttatcctg agatggaga tactaagtac      180
aatggaagt tcaagggcag ggtcacaatc actgcagacg aatccaccag cacagcctac      240
atggaactca gcagcctgag atctgaggac tctgccgtct atttctgtgc aagattcctg     300
cttattagta ctgtgacagc cgtcgactac tggggccaag gcaccactgt cacagtctcc     360
tca                                                                   363
```

<210> SEQ ID NO 56
<211> LENGTH: 363
<212> TYPE: DNA
<213> ORGANISM: Artificial Sequence
<220> FEATURE:
<223> OTHER INFORMATION: Nucleic acid encoding humanized antibody
      segment

<400> SEQUENCE: 56

```
caggttcagc tggtgcagtc tggagctgag gtgaagaagc ctggggcctc agtgaaggtt      60
tcctgcaagg cttctggcta cgcattcagt aactcctgga tgaactgggt gaagcaggct     120
cctggacagg gtctagagtg gataggacgg atttatcctg agatggaga tactaagtac      180
aatggaagt tcaagggcaa ggccacaatg actgcagaca catccaccag cacagcctac      240
atggaactca gcagcctgag atctgaggac actgccgtct attactgtgc aagattcctg     300
cttattagta ctgtgacagc cgtcgactac tggggccaag gcacccttgt cacagtctcc     360
tca                                                                   363
```

<210> SEQ ID NO 57
<211> LENGTH: 363
<212> TYPE: DNA
<213> ORGANISM: Artificial Sequence
<220> FEATURE:
<223> OTHER INFORMATION: Nucleic acid encoding humanized antibody
      segment

<400> SEQUENCE: 57

```
caggttcagc tggtgcagtc tggagctgag gtgaagaagc ctggggcctc agtgaaggtt      60
tcctgcaagg cttctggcta cgcattcagt aactcctgga tgaactgggt gaggcaggct     120
cctggacagg gtctagagtg gatgggacgg atttatcctg agatggaga tactaagtac      180
aatggaagt tcaagggcag ggtcacaatc actgcagaca catccaccag cacagtctac      240
atggaactca gcagcctgag atctgaggac actgccgtct attactgtgc aagattcctg     300
cttattagta ctgtgacagc cgtcgactac tggggccaag gcacccttgt cacagtctcc     360
tca                                                                   363
```

<210> SEQ ID NO 58
<211> LENGTH: 12
<212> TYPE: PRT
<213> ORGANISM: Artificial Sequence
<220> FEATURE:
<223> OTHER INFORMATION: Second extracellular loop of C5aR

<400> SEQUENCE: 58

Val Arg Glu Glu Tyr Phe Pro Pro Lys Val Leu Cys
1               5                   10

```
<210> SEQ ID NO 59
<211> LENGTH: 21
<212> TYPE: PRT
<213> ORGANISM: Artificial Sequence
<220> FEATURE:
<223> OTHER INFORMATION: N-terminal portion of human C5aR

<400> SEQUENCE: 59

Pro Asp Tyr Gly His Tyr Asp Asp Lys Asp Thr Leu Asp Leu Asn Thr
1               5                   10                  15

Pro Val Asp Lys Thr
            20
```

HUMANIZED ANTI-C5AR ANTIBODIES

CROSS-REFERENCE TO RELATED APPLICATIONS

This application is a national phase filing under 35 U.S.C. §371 of International Patent Application No.PCT/AU09/00184, filed Feb. 19, 2009, which claims the benefit of U.S. Provisional Patent Application No. 61/066,539, filed Feb. 20, 2008.

FIELD OF THE INVENTION

The present invention is directed to humanized antibodies which bind the human C5a receptor and their use as therapeutic and diagnostic agents. The present invention is further directed toward nucleic acid sequences which encode said humanized antibodies, and their expression in recombinant host cells. In particular, the present invention is directed towards humanized antibodies derived from murine antibody 7F3 which specifically binds to the human C5a receptor.

BACKGROUND OF THE INVENTION

Proteolysis of each of the complement proteins C3-C5 gives rise to amino-terminal cationic fragments with signalling molecules called anaphylatoxins. The most potent of these, C5a, elicits the broadest responses. Considering the components of the inflammatory response as margination and infiltration of leukocytes, release of granule-bound proteolytic enzymes, production of activated oxygen and nitrogen-derived radicals, changes in blood flow and capillary leakage, along with the ability to contract smooth muscle, the C5a molecule is the "complete" pro-inflammatory mediator. At sub-nanomolar to nanomolar levels, the C5a molecule elicits chemotaxis of all myeloid lineages (neutrophils, eosinophils and basophils, macrophages and monocytes), and causes vascular permeability which is markedly potentiated by prostaglandins and circulating leukocytes. Higher nanomolar concentrations elicit degranulation and activation of NADPH oxidase. This breadth of bioactivity contrasts with other inflammatory mediators. C5a is involved in the pathogenesis of various disorders including rheumatoid arthritis, psoriasis, sepsis, reperfusion injury, and adult respiratory distress syndrome (Gerard and Gerard, 1994; Murdoch and Finn, 2000).

The activities of C5a are mediated by the binding of the C5a to its receptor (C5aR). C5aR belongs to the family of seven transmembrane G-protein-coupled receptors. C5aR is a high affinity receptor for C5a, with a Kd of ~1 nM, and is located on a number of different cell types including leukocytes. The number of receptors per cell is extremely high, up to 200,000 sites per leukocyte. Biological activation of the receptor occurs over the range that saturates binding.

The C5aR structure conforms to the seven transmembrane receptor family, with the extracellular N-terminus being followed by seven transmembrane helices connected by interhelical domains alternating as intracellular and extracellular loops, and ending with an intracellular C-terminal domain. C5aR contains an extended N-terminal extracellular domain. This large N-terminal domain is typical of G-protein coupled receptors which bind peptides including the IL-8 and fMet-Leu-Phe (FMLP) receptor families.

Inhibition of the C5a responses with C5aR antagonists reduces the acute inflammatory response mediated via C5a without affecting other complement components. To this end, C5aR peptide antagonists and anti-C5a receptor antibodies have been previously described (Watanabe et al., 1995; Pellas et al., 1998; Konteatis et al., 1994; Kaneko et al., 1995; Morgan et al., 1993). For example, WO 95/00164 describes antibodies directed against an N-terminal peptide (residues 9-29) of C5aR.

WO 03/062278 also describes antibodies directed against C5aR. Three of these mouse antibodies were termed 7F3, 6C12 and 12D4. These antibodies were shown to have excellent properties, such as being very effective at blocking C5a binding to its receptor, stopping C5a-directed migration of neutrophils in vitro, and preventing inflammation in animal models. To control chronic diseases it may be necessary to administer the antibody on successive occasions over months or years. However, one drawback from administering mouse antibodies is that the human immune system may generate its own antibodies directed against the mouse antibody (the HAMA response). The HAMA response can neutralize the mouse antibodies by rapidly clearing them from the blood, thus preventing the mouse antibody from binding to its target.

To avoid development of a HAMA response one strategy that has been adopted is to "humanize" the mouse antibody by replacing as many "foreign" residues in the non-epitope binding regions with human sequences. However, this process often results in loss of antigenicity. Furthermore, researchers in the art of humanizing antibodies have struggled to characterize appropriate guidelines to reliably produce humanized antibodies that have all the necessary requirements for use in human therapy.

A major problem of humanization procedures has been a loss of affinity for the antigen (Jones et al., 1986), in some instances as much as 10-fold or more, especially when the antigen is a protein (Verhoeyen et al., 1988). Loss of any affinity is, of course, highly undesirable. At the least, it means that more of the humanized antibody will have to be injected into the patient, at higher cost and greater risk of adverse effects. Even more critically, an antibody with reduced affinity may have poorer biological functions, such as complement lysis, antibody-dependent cellular cytotoxicity, or virus neutralization. Thus, the structure of any final antibody that is useful for therapeutic or diagnostic applications based on humanization is currently unpredictable, with several iterations and employment of several techniques often being required to obtain a useful humanized antibody.

There is a need for alternative and/or improved C5aR antagonists which can be used in diagnostic and/or therapeutic methods. In particular, there is a need for the development of suitable humanized anti-C5aR antibodies for said diagnostic and/or therapeutic methods in humans.

SUMMARY OF THE INVENTION

A large number of humanized antibodies which bind C5aR but have poor binding specificities and/or other undesirable characteristics have been produced. However, the present inventors have produced a few related humanized antibodies that have suitable activities to be used for diagnostic and/or therapeutic methods in humans.

In a first aspect, the present invention provides a substantially purified and/or recombinant humanized antibody which comprises i) an immunoglobulin light chain comprising a variable region comprising an amino acid sequence which is at least 93% identical to one or more of SEQ ID NO:31, SEQ ID NO:32, SEQ ID NO:33 and SEQ ID NO:48, and/or ii) an immunoglobulin heavy chain comprising a variable region comprising an amino acid sequence which is at least 90% identical to one or more of SEQ ID NO:34, SEQ ID NO:35, SEQ ID NO:36 and SEQ ID NO:39, wherein the antibody binds human C5aR.

In a preferred embodiment, the immunoglobulin heavy chain comprises a variable region comprising an amino acid sequence selected from the group consisting of: SEQ ID NO:34, SEQ ID NO:35 and SEQ ID NO:36. More preferably, the immunoglobulin heavy chain comprises a variable region comprising an amino acid sequence provided as SEQ ID NO:36.

In another preferred embodiment, the immunoglobulin light chain comprises a variable region comprising an amino acid sequence selected from the group consisting of: SEQ ID NO:31, SEQ ID NO:32 and SEQ ID NO:33. More preferably, the immunoglobulin light chain comprises a variable region comprising an amino acid sequence provided as SEQ ID NO:31.

In a particularly preferred embodiment, the immunoglobulin light chain comprises a variable region comprising an amino acid sequence provided as SEQ ID NO:31, and the immunoglobulin heavy chain comprises a variable region comprising an amino acid sequence provided as SEQ ID NO:36. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:42, SEQ ID NO:43, SEQ ID NO:44 or SEQ ID NO:45. More preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:43 or SEQ ID NO:45, more preferably SEQ ID NO:45.

In an embodiment, the immunoglobulin light chain comprises a variable region comprising an amino acid sequence provided as SEQ ID NO:31, and the immunoglobulin heavy chain comprises a variable region comprising an amino acid sequence provided as SEQ ID NO:34. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:42 or SEQ ID NO:43.

In another embodiment, the immunoglobulin light chain comprises a variable region comprising an amino acid sequence provided as SEQ ID NO:32, and the immunoglobulin heavy chain comprises a variable region comprising an amino acid sequence provided as SEQ ID NO:34. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:42 or SEQ ID NO:43.

In a further embodiment, the immunoglobulin light chain comprises a variable region comprising an amino acid sequence provided as SEQ ID NO:33, and the immunoglobulin heavy chain comprises a variable region comprising an amino acid sequence provided as SEQ ID NO:34. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:42, SEQ ID NO:43 or SEQ ID NO:44.

In another embodiment, the immunoglobulin light chain comprises a variable region comprising an amino acid sequence provided as SEQ ID NO:31, and the immunoglobulin heavy chain comprises a variable region comprising an amino acid sequence provided as SEQ ID NO:35. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:42, SEQ ID NO:43, SEQ ID NO:44 or SEQ ID NO:45.

In another embodiment, the immunoglobulin light chain comprises a variable region comprising an amino acid sequence provided as SEQ ID NO:32, and the immunoglobulin heavy chain comprises a variable region comprising an amino acid sequence provided as SEQ ID NO:35. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:43.

In a further embodiment, the immunoglobulin light chain comprises a variable region comprising an amino acid sequence provided as SEQ ID NO:33, and the immunoglobulin heavy chain comprises a variable region comprising an amino acid sequence provided as SEQ ID NO:35. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:43.

In another embodiment, the immunoglobulin light chain comprises a variable region comprising an amino acid sequence provided as SEQ ID NO:32, and the immunoglobulin heavy chain comprises a variable region comprising an amino acid sequence provided as SEQ ID NO:36. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:43.

In a further embodiment, the immunoglobulin light chain comprises a variable region comprising an amino acid sequence provided as SEQ ID NO:33, and the immunoglobulin heavy chain comprises a variable region comprising an amino acid sequence provided as SEQ ID NO:36. Preferably, the immunoglobulin light chain comprises a constant region comprising an amino acid sequence provided as SEQ ID NO:41, and the immunoglobulin heavy chain comprises a constant region comprising an amino acid sequence provided as SEQ ID NO:43.

In a preferred embodiment, the antibody binds the epitope EEYFPP (SEQ ID NO:38) on the second extracellular loop of human C5aR. In a further embodiment, the antibody does not detectably bind the epitope PDYGHYDDKDTLDLNT-PVDKT (SEQ ID NO:59) on the N-terminus of human C5aR.

In a preferred embodiment, the antibody binds human C5aR with an affinity which is at least within 8-fold of 7F3, more preferably at least within 4-fold of 7F3, and even more preferably at least within 3-fold of 7F3.

In a preferred embodiment, an antibody of the invention has an $EC_{50}$ of less than 4.5 nM for human neutrophils expressing human C5aR. In alternate embodiments, an antibody of the invention has an $EC_{50}$ of less than 3 nM, less than 2 nM, or less than 1 nM. The $EC_{50}$ of an antibody for human neutrophils expressing C5aR can be determined as described in Example 3.

In another embodiment, an antibody of the invention is capable of reducing human neutrophil migration by at least 40%, more preferably at least 50%, more preferably at least 60%, more preferably at least 70% and even more preferably at least 80%. In a further embodiment, an antibody of the invention has a greater ability, preferably at least a 2 fold greater ability, even more preferably 5 fold greater ability, to block C5aR induced human neutrophil migration than 7F3. A reduction in human neutrophil migration can be determined as described in Example 5.

In a further embodiment, an antibody of the invention does not detectably activate human neutrophils. Neutrophil activation can be determined by analysing CD62L and CD11b expression, and/or superoxide production, as described in Example 7.

In yet another embodiment, an antibody of the invention does not detectably deplete neutrophils or monocytes from blood ex vivo. Depletion of neutrophils or monocytes ex vivo can be determined as described in Examples 8 and 9.

In a further embodiment, an antibody of the invention is capable of blocking C5a-induced Ca$^{2+}$ influx into a human neurophil at an antibody concentration of less than 30 μg/ml, more preferably less than 10 μg/ml, more preferably less than 5 μg/ml, more preferably less than 1 μg/ml. Blocking C5a-induced Ca$^{2+}$ influx into a human neurophil can be determined as described in Example 6.

In one example, an antibody of the invention is non-depleting and non-activating. An example of such an antibody described herein is hAb-Q. In an alternate embodiment, an antibody of the invention is depleting and non-activating. An example of such an antibody described herein is hAb-N.

In a preferred embodiment,
i) the immunoglobulin light chain comprises a constant region comprising an amino acid sequence which is at least 90% identical to one or more of SEQ ID NO:40, and SEQ ID NO:41, and
ii) the immunoglobulin heavy chain comprises a constant region comprising an amino acid sequence which is at least 90% identical to one or more of SEQ ID NO:42, SEQ ID NO:43, SEQ ID NO:44 and SEQ ID NO:45. More preferably,
i) the immunoglobulin light chain comprises a constant region comprising an amino acid sequence which is at least 90% identical to SEQ ID NO:41, and
ii) the immunoglobulin heavy chain comprises a constant region comprising an amino acid sequence which is at least 90% identical to SEQ ID NO:45.

The humanized antibody can be of any suitable structure known in the art. Examples include, but are not limited to, a four-polypeptide chain structure consisting of two heavy and two light chains, a single chain antibody, diabody, triabody or tetrabody, as well as antibody fragments such as, but not limited to, a Fab fragment or single domain antibody.

In another aspect, the present invention provides a substantially purified and/or recombinant immunoglobulin light chain comprising a variable region comprising an amino acid sequence which is at least 93% identical to one or more of SEQ ID NO:31, SEQ ID NO:32, SEQ ID NO:33 and SEQ ID NO:48.

In a preferred embodiment, the immunoglobulin light chain comprises a variable region comprising an amino acid sequence which is at least 93% identical to SEQ ID NO:31.

In a further aspect, the present invention provides a substantially purified and/or recombinant immunoglobulin heavy chain comprising a variable region comprising an amino acid sequence which is at least 90% identical to one or more of SEQ ID NO:34, SEQ ID NO:35, SEQ ID NO:36 and SEQ ID NO:39.

In a preferred embodiment, the immunoglobulin heavy chain comprises a variable region comprising an amino acid sequence which is at least 90% identical to SEQ ID NO:36.

In another aspect, the present invention provides a substantially purified and/or recombinant antibody comprising the immunoglobulin light chain of the invention and/or the immunoglobulin heavy chain of the invention, wherein the antibody binds human C5aR.

Also provided is a conjugate comprising an antibody of the invention and a therapeutic agent which is directly or indirectly bound to the antibody. Examples of therapeutic agents include, but are not limited to, a cytotoxin, a radioisotope (for instance, iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent, and a therapeutic nucleic acid.

In an embodiment, the toxin is *Pseudomonas* exotoxin or a derivative thereof.

In a further embodiment, the therapeutic agent is indirectly bound to the antibody via a linker. Examples include, but are not limited to, 4-(4'acetylphenoxy)butanoic acid (AcBut), 3-acetylphenyl acidic acid (AcPac), 4-mercapto-4-methyl-pentanoic acid (Amide), and derivatives thereof.

In another aspect, the present invention provides conjugate comprising an antibody of the invention and a detectable label which is directly or indirectly bound to the antibody. Examples of suitable labels include, but are not limited to, a radiolabel, a fluorescent label, an enzymatic label and an imaging agent.

In a further aspect, the present invention provides an isolated and/or exogenous polynucleotide encoding an antibody of the invention or a chain thereof, an immunoglobulin light chain of the invention, an immunoglobulin heavy chain of the invention and/or a conjugate of the invention.

Preferably, the polynucleotide comprises a sequence provided as any one of SEQ ID NO's 52 to 57.

In another aspect, the present invention provides a vector comprising a polynucleotide of the invention. Preferably, the vector is an expression vector. More preferably, the polynucleotide is operably linked to a promoter.

In another aspect, the present invention provides a host cell comprising a polynucleotide of the invention and/or a vector of the invention. The host cell can be any cell type such as a bacterial, yeast, plant or animal cell.

Also provided is a non-human transgenic organism comprising a cell of the invention.

Also provided is a composition comprising an antibody of the invention, an immunoglobulin light chain of the invention, an immunoglobulin heavy chain of the invention, a conjugate of the invention, a polynucleotide of the invention, a vector of the invention and/or a host cell of the invention, and a carrier.

In another aspect, the present invention provides a process for producing an antibody comprising culturing a host cell of the invention so that the polynucleotide is expressed and the antibody produced, wherein the host cell comprises at least one polynucleotide of the invention.

In one embodiment, the immunoglobulin light chain and the immunoglobulin heavy chain are encoded by two separate open reading frames on one contiguous polynucleotide.

Preferably, the process further comprises recovering the antibody from the host cell culture.

In a further aspect, the present invention provides a method for inhibiting the interaction of human C5aR with a ligand thereof, the method comprising exposing the cell to an antibody of the invention or a conjugate of the invention.

Preferably, the ligand is human C5a.

Preferably, the antibody or a conjugate prevents at least some ligand binding to the cell.

In another aspect, the present invention provides a method for inhibiting human C5aR activity in a cell, the method comprising exposing the cell to an antibody of the invention or a conjugate of the invention.

With regard to the two preceding aspects, the methods can be performed in vitro or in vivo.

In another aspect, the present invention provides a method of treating or preventing a disorder in a subject, the method comprising administering to the subject an antibody of the invention, a conjugate of the invention, a polynucleotide of the invention, a vector of the invention, a host cell of the invention and/or a composition of the invention.

In one embodiment, the disorder is an immunopathological disorder such as an autoimmune disease.

In another embodiment, the disorder is an inflammatory disease such as acute inflammation or chronic inflammation.

In another embodiment, the immunopathological disorder or inflammatory disease involves leukocyte migration and/or leukocyte activation.

In a further embodiment; the immunopathological disorder or inflammatory disease involves complement activation.

Examples of disorders that can be treated or prevented include, but are not limited to, allergic rhinitis, hypersensitivity lung diseases, hypersensitivity pneumonitis, interstitial lung diseases, anaphylaxis responses, hypersensitivity responses, drug allergies, insect sting allergies, inflammatory bowel diseases, spondyloarthropathies, scleroderma, psoriasis, dermatitis, eczema, atopic dermatitis, allergic contact dermatitis, urticaria, vasculitis, arthritis, multiple sclerosis, systemic lupus erythematosus, myasthenia gravis, juvenile onset diabetes, nephritides, autoimmune thyroiditis, Behcet's disease, graft rejection, atherosclerosis, cancers with leukocyte infiltration of the skin or organs, reperfusion injury, stroke, adult respiratory distress syndrome, hematologic malignancies, cytokine-induced toxicity, polymyositis, dermatomyositis, pemphigoid, Alzheimers disease, granulomatous diseases, hemophilic synovitis, gout, adverse inflammatory reactions associated with infections, SAR, sepsis, chronic obstructive pulmonary disease (COPD), rheumatoid arthritis, anti-phospholipid syndrome, age-related macular degeneration, membranoproliferative glomerulonephritis and dense deposit disease.

The methods of the invention can be performed in combination with other known therapies. Thus, in an embodiment the method further comprises administering at least one other compound for treating or preventing the disorder. Such other therapies can be provided concurrently or sequentially.

As the skilled addressee will appreciate, when a polynucleotide of the invention, a vector of the invention and/or a host cell is administered to the subject it will be under suitable conditions such that the antibody or conjugate is expressed in vivo.

Preferably, the antibody, conjugate, polynucleotide, vector and/or host cell is administered as a composition of the invention.

In another aspect, the present invention provides a method for delivering a therapeutic agent to a site of inflammation in a subject, the method comprising administering to the subject a conjugate of the invention, or a polynucleotide encoding therefor.

In a further aspect, the present invention provides a method for introducing genetic material into cells presenting C5aR, the method comprising contacting the cells with an antibody according of the invention, or a conjugate of the invention, wherein the antibody or conjugate is attached to or associated with genetic material.

Examples of genetic material include DNA, RNA or a combination thereof. In a preferred embodiment, the genetic material is at least partially double stranded DNA or at least partially double stranded RNA.

In a preferred embodiment, the cells presenting C5aR are selected from the group consisting of leukocytes such as granulocytes (e.g. neutrophils, basophils, eosinophils), monocytes, mast cells and plasmacytoid dendritic cells, as well as immune cells in the tissues such as macrophages (e.g. microglia, hepatic Kupffer cells, renal glomerular mesangial cells), B lymphocytes, T lymphocytes, vascular endothelial cells, cardiomyocytes, astrocytes, neural stem cells, oligodendrocytes, synoviocytes, articular chrondocytes, stimulated hepatocytes, bronchial epithelial cells, keratinocytes and thymocytes. In a particularly preferred embodiment, the cells presenting C5aR are selected from the group consisting of leukocytes such as granulocytes (e.g. neutrophils, basophils, eosinophils), monocytes, mast cells and plasmacytoid dendritic cells, as well as immune cells in the tissues such as macrophages (e.g. microglia, hepatic Kupffer cells, renal glomerular mesangial cells).

In yet another aspect, the present invention provides a method of detecting the presence or absence of human C5aR in a sample, the method comprising contacting the sample with an antibody of the invention, and/or a conjugate of the invention, and analysing the sample for binding between human C5aR and the antibody or conjugate.

Examples of suitable samples which can be tested include, but are not necessarily limited to, blood, serum, plasma, as well as cell or tissue biopsies.

In another aspect, the present invention provides a method for diagnosing a disorder in a subject, the method comprising contacting the subject, or a sample obtained therefrom, with an antibody of the invention, or a conjugate of the invention, and analysing the subject or sample for binding between human C5aR and the antibody or conjugate.

Thus, the method can be performed in vitro or in vivo.

In an embodiment, the method is performed in vitro using histological specimens or subfractions of tissue or fluid obtained from the subject.

In another embodiment, the method comprises administering to the subject an antibody of the invention labeled with an imaging agent under conditions so as to form a complex between the antibody and cells presenting C5aR in the subject, and imaging the complex.

Preferably, the disorder is an immunopathological disorder.

Also provided is the use of an antibody of the invention, a conjugate of the invention, a polynucleotide of the invention, a vector of the invention, a host cell of the invention and/or a composition of the invention for the manufacture of a medicament for treating or preventing a disorder in a subject.

Also provided is the use of a conjugate of the invention, or a polynucleotide encoding therefor, for the manufacture of a medicament for delivering a therapeutic agent to a site of inflammation in a subject.

Also provided is the use of an antibody of the invention, a conjugate of the invention, a polynucleotide of the invention, a vector of the invention, a host cell of the invention and/or a composition of the invention as a medicament for treating or preventing a disorder in a subject.

Also provided is the use of a conjugate of the invention, or a polynucleotide encoding therefor, as a medicament for delivering a therapeutic agent to a site of inflammation in a subject.

In a further aspect, the present invention provides a kit comprising an antibody of the invention, a conjugate of the invention, a polynucleotide of the invention, a vector of the invention, a host cell of the invention and/or a composition of the invention.

As will be apparent, preferred features and characteristics of one aspect of the invention are applicable to many other aspects of the invention.

As the skilled addressee will appreciate, in many aspects of the invention it is preferred that the defined molecule (antibody or immunoglobulin etc) consists essentially of, or more preferably consist of, a sequence of the nominated SEQ ID NO as opposed to comprising said sequence.

The invention is hereinafter described by way of the following non-limiting Examples and with reference to the accompanying figures.

BRIEF DESCRIPTION OF THE ACCOMPANYING DRAWINGS

FIG. 1. ClustalW alignment of human Ig light chain sequences with greatest homology to the mouse 7F3 light chain Vk region. The CDRs as defined for 7F3 are boxed. The consensus framework sequence is shown, hVkFW Cons.

FIG. 2. ClustalW alignment of human Ig heavy chain V region sequences (A) and J region sequences (B) with greatest homology to the mouse 7F3 heavy chain Vh sequence. The CDRs as defined for 7F3 are boxed. The consensus framework sequences for the V region (hVhvFW Cons) and J region (hVhjFW Cons) as shown were joined to create a consensus sequence (hVhFW Cons) for grafting the 7F3 CDRs (note: the D region is contained within CDR-H3).

FIG. 3. An alignment of the consensus human Vk framework sequence from FIG. 1 with mouse 7F3 Vk sequence was used to create the humanized 7F3 Vk light chain sequence, h7Vk. The mouse 7F3 CDRs (boxed) were grafted into the hVkFW consensus framework sequence. The three amino acids marked by asterisk were back-mutated to the mouse 7F3 framework sequence.

FIG. 4. An alignment of the humanized RNOK203VL sequence with mouse 7F3 Vk sequence was used to create the humanized 7F3 Vk light chain sequence, h7aVk. The mouse 7F3 CDRs (boxed) were grafted into the RNOK203VL framework sequence.

FIG. 5. An alignment of the KV2F-HUMAN derived VLCD18-Q sequence with mouse 7F3 Vk sequence was used to create the humanized 7F3 Vk light chain sequence, h7bVk. The mouse 7F3 CDRs (boxed) were grafted into the VLCD18-Q framework sequence.

FIG. 6. An alignment of the humanized 7F3 Vk sequences with mouse 7F3 Vk sequences. The consensus sequence h7F3VkCons is a consensus of the three humanized sequences. The CDRs are boxed. Differences between the humanized 7F3 Vk sequences are indicated by white type on black background.

FIG. 7. An alignment of the consensus human Vh framework sequence from FIGS. 2A and 2B with mouse 7F3 Vh sequence was used to create the humanized 7F3 Vh heavy chain sequence, h7Vh. The mouse 7F3 CDRs (boxed) were grafted into the hVhFW consensus framework sequence. The amino acids marked by asterisk (*) were back-mutated to the mouse 7F3 framework sequence. The amino acid marked with # were mutated to alternate residues as discussed in the text.

FIG. 8. An alignment of the human SGI-VH sequence with mouse 7F3 Vh sequence was used to create the humanized 7F3 Vh heavy chain sequence, h7aVh. The mouse 7F3 CDRs (boxed) were grafted into the SGI-VH framework sequence.

The amino acids marked by asterisk (*) were back-mutated to the mouse 7F3 framework sequence.

FIG. 9. An alignment of the human HG3 sequence with mouse 7F3 Vh sequence was used to create the humanized 7F3 Vh heavy chain sequence, h7bVh. The mouse 7F3 CDRs (boxed) were grafted into the HG3 framework sequence. The amino acid marked by asterisk (*) was back-mutated to the mouse 7F3 framework sequence.

FIG. 10. An alignment of the humanized 7F3 Vh sequences with mouse 7F3 Vh sequences. The consensus sequence h7F3VhCons is a consensus of the three humanized sequences. The CDRs are boxed. Differences between the humanized 7F3 Vh sequences are indicated by white type on black background.

Figure 11:
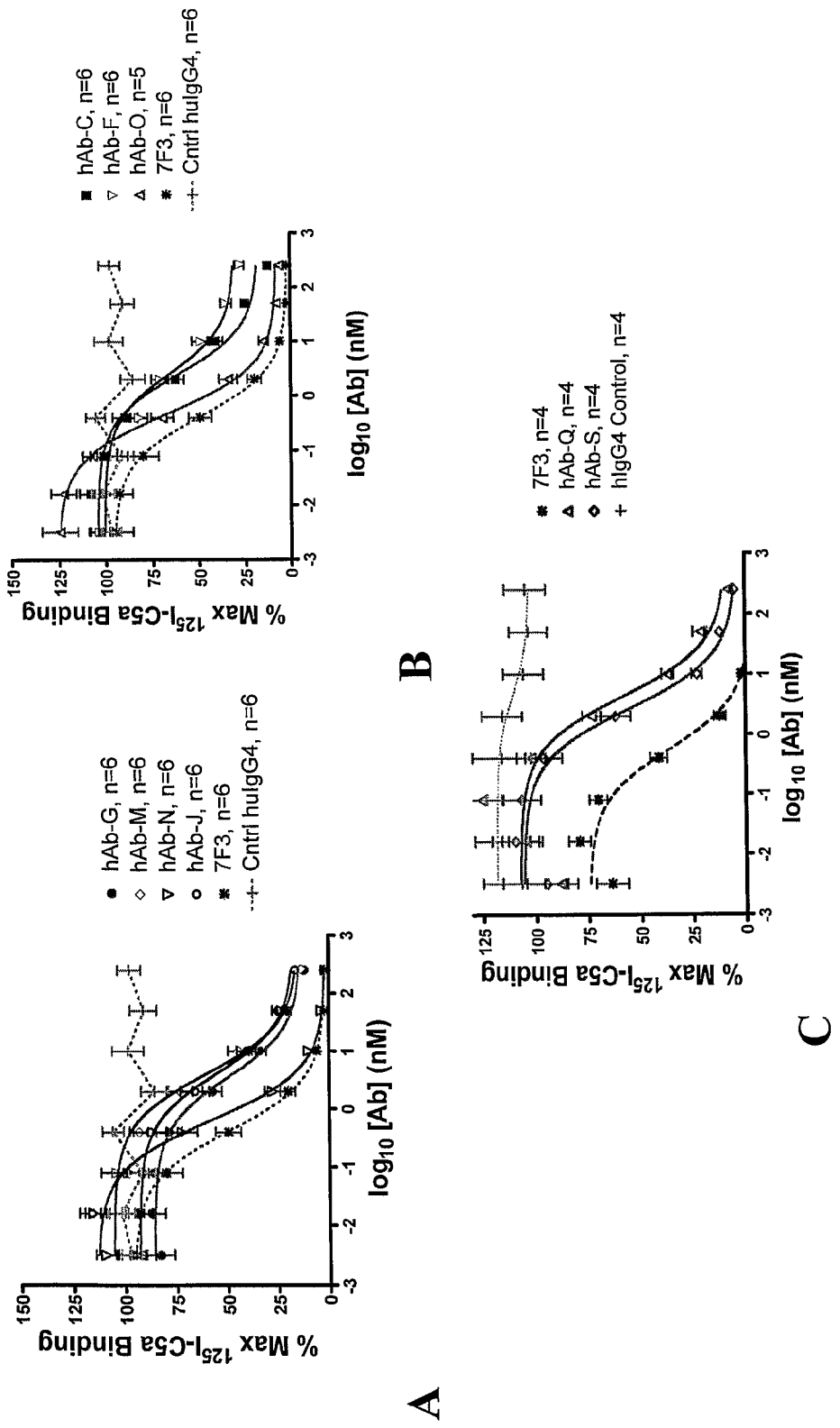

FIG. 11. Competitive ligand binding assays comparing displacement of $^{125}$I-C5a by humanized 7F3 antibodies and mouse 7F3 from hC5aR on human neutrophils.

Figure 12A:
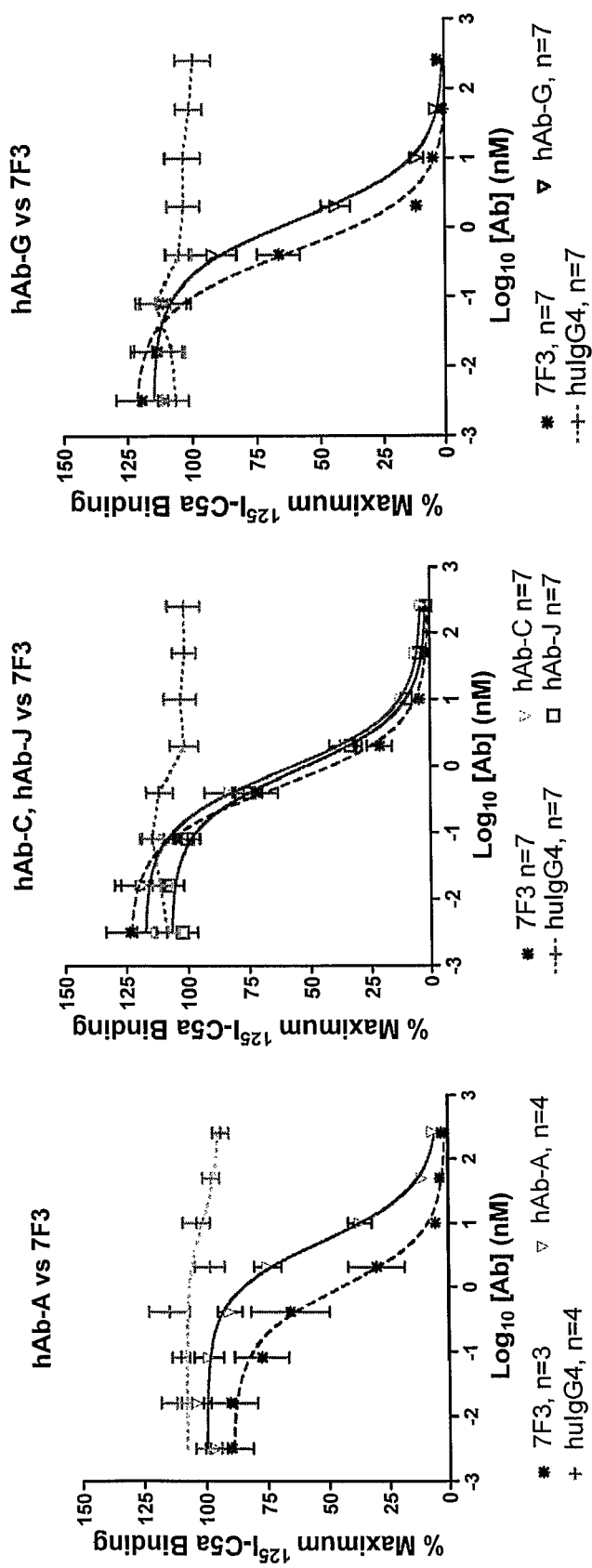
Figure 12B:
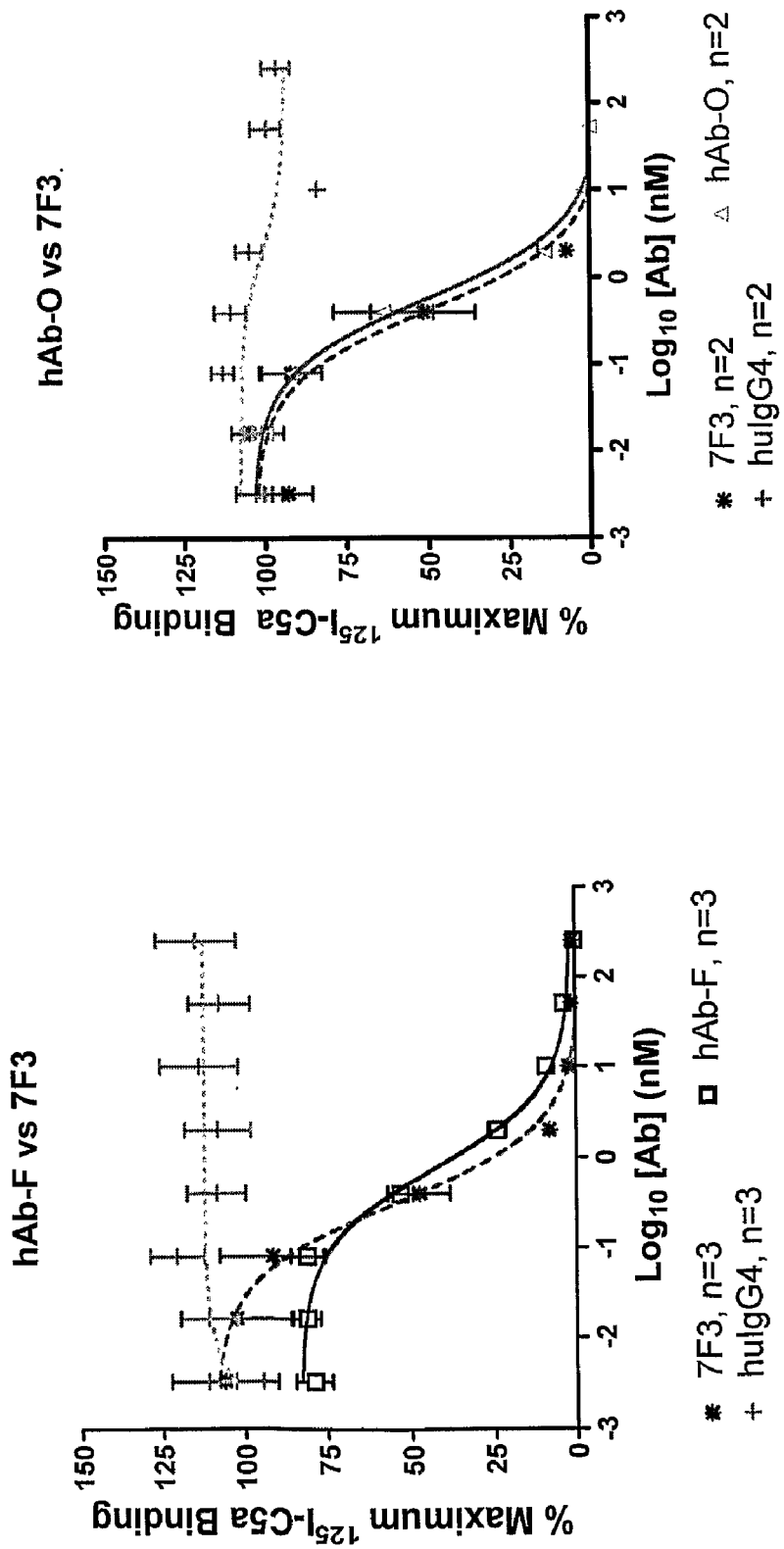
Figure 12C:
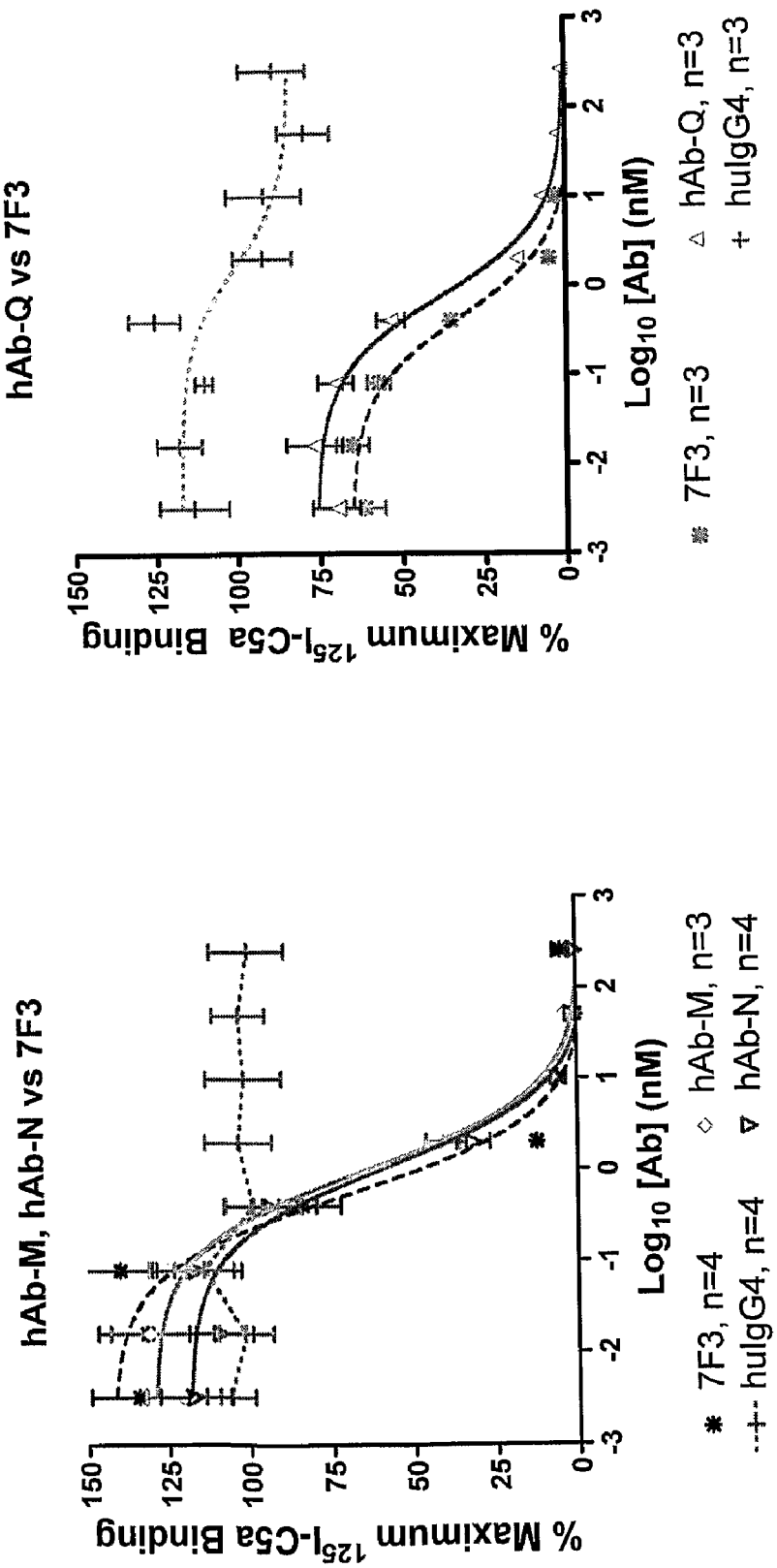

FIG. 12. Competitive ligand binding assays comparing displacement of $^{125}$I-C5a by humanized 7F3 antibodies and mouse 7F3 from hC5aR on L1.2/hC5aR transfectants.

FIG. 13. Saturation binding of anti-C5aR antibodies to human neutrophils at 4° C. plotted with $\log_{10}$ (top panel) and linear (bottom panel) scales on x-axis.

FIG. 14. Peptide ELISAs: Binding of humanized anti-C5aR antibodies hAb-J (panel A) and hAb-Q (panel B) to a series of overlapping peptides (no. 1-22) comprising a 12 mer sequence (each offset by one) from the 2nd extracellular loop of human C5aR and a 33 mer comprising residues 173-205 from SEQ ID NO:37 (no. 23). Binding of hAb-J (panel C) and hAb-Q (panel D) to a 12 mer sequence from the 2nd extracellular loop of human C5aR (no. A1) a series of mutated peptides (no. A2-A13) comprising the 12 mer with a single Ala mutation, and a scrambled peptide (no. A14).

Figure 15:
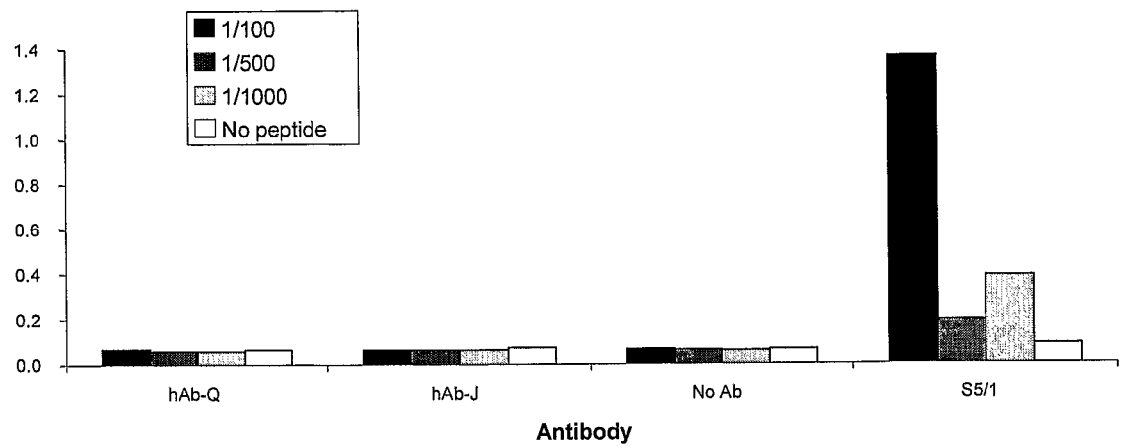

FIG. 15. Binding of humanized anti-C5aR mAbs hAb-J and Q or anti-C5aR mAb S5/1 (at 5 μg/ml) to peptide PEP1 (residues 9-29 of SEQ ID NO:37) coated onto an ELISA plate at different dilutions.

Figure 16:
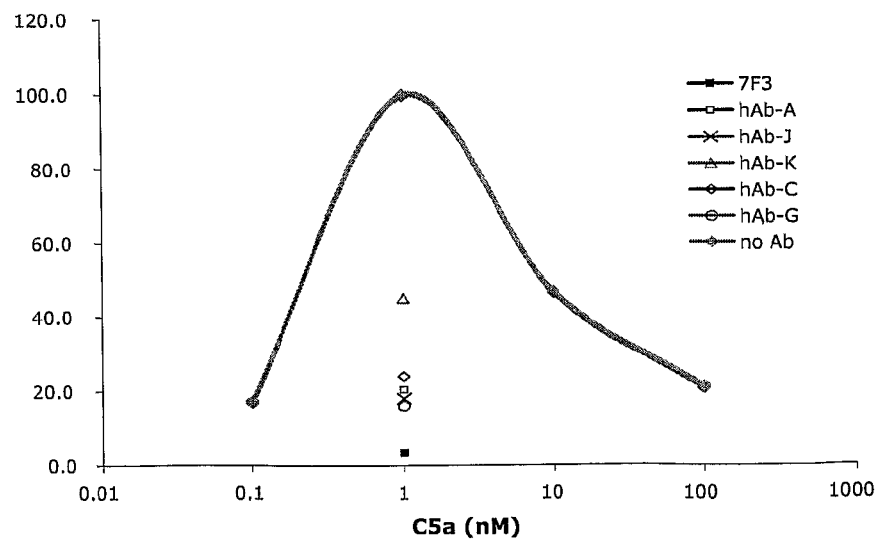

FIG. 16. Chemotaxis assay: migration of human neutrophils to 1 nM C5a in the presence of 5 μg/ml 7F3 and various humanized 7F3 antibodies.

FIG. 17. Inhibition of C5a-induced chemotaxis of human neutrophils by anti-C5aR antibodies hAb-Q (closed diamond) and 7F3 (open square). Average (±sem) results from 4 separate experiments are shown as percentage of maximum migration of no antibody control sample (upper panel) or as average number of migrating cells (lower panel). The units on the x-axis are $\log_{10}$ Ab concentration in μg/ml.

Figure 18:
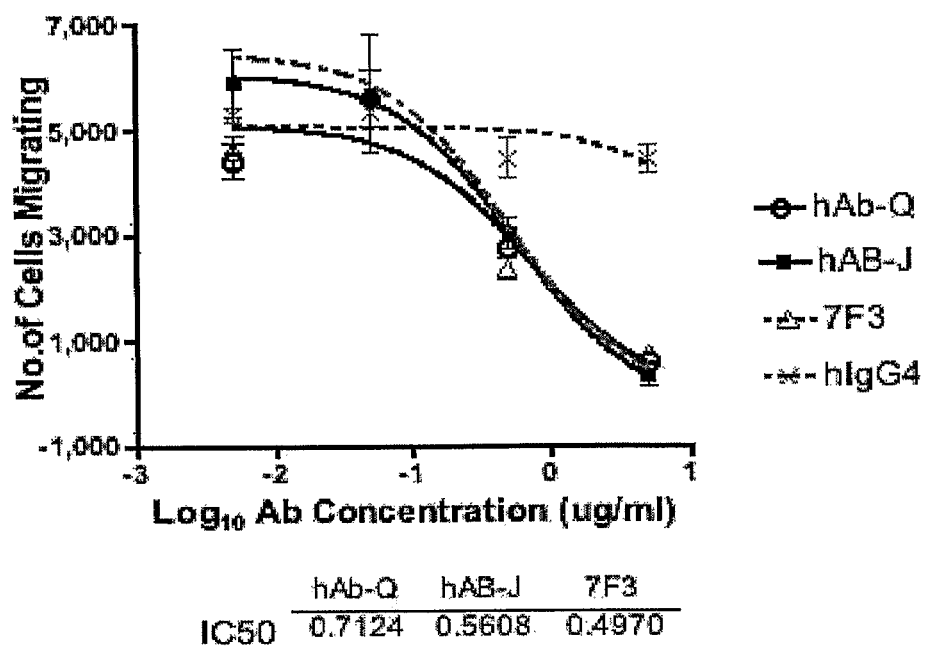

FIG. 18. Inhibition of C5a-directed hC5aR/L1.2 transfectant cell migration by the parent mouse antibody 7F3 and humanized antibodies J and Q.

Figure 19:
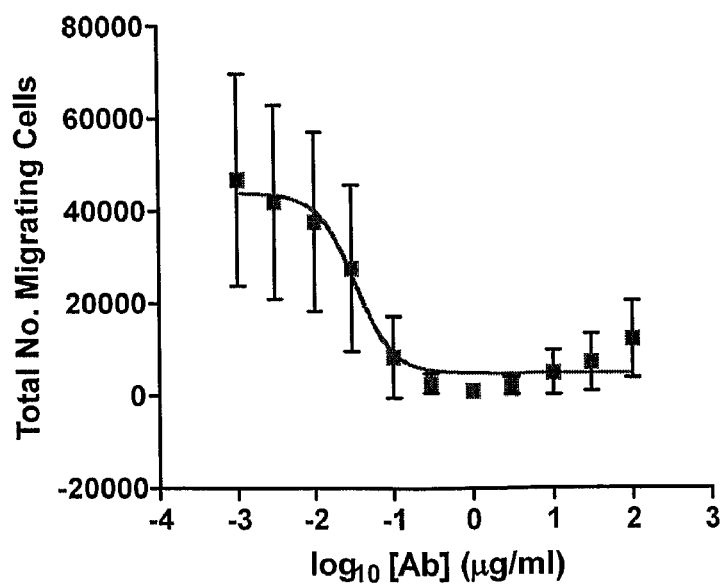

FIG. 19. C5a-induced chemotaxis of human neutrophils was repressed after pre-incubation with high concentrations of humanized anti-C5aR antibody hAb-Q.

Figure 20:
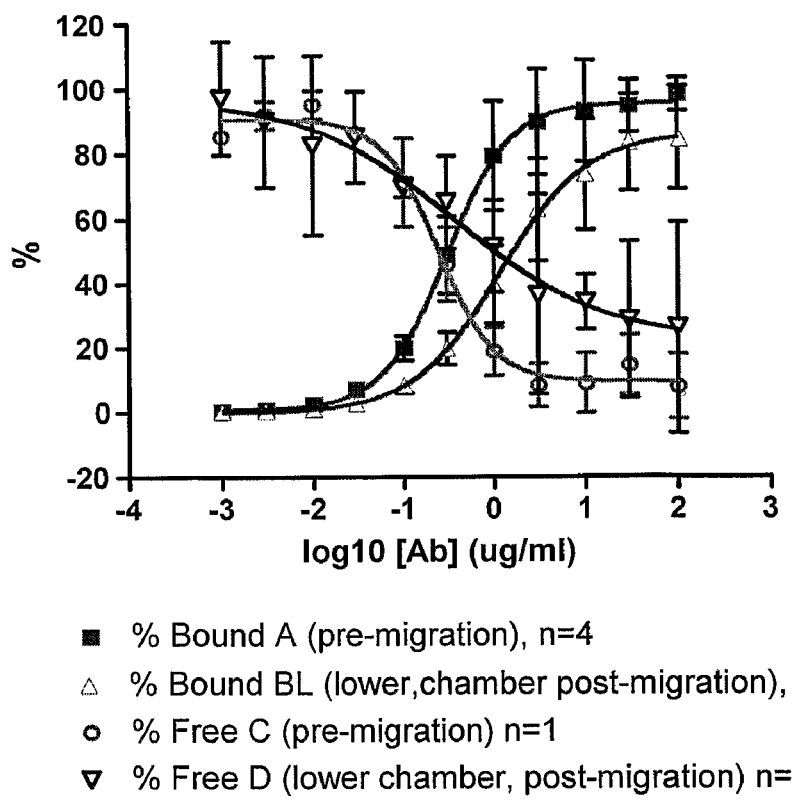

FIG. 20. Inverse relationship observed between level of free C5aR and bound anti-C5aR antibody hAb-Q on human neutrophils before and after C5a-induced chemotaxis of cells pre-incubated with various concentrations of humanized anti-C5aR antibody hAb-Q.

Figure 21:
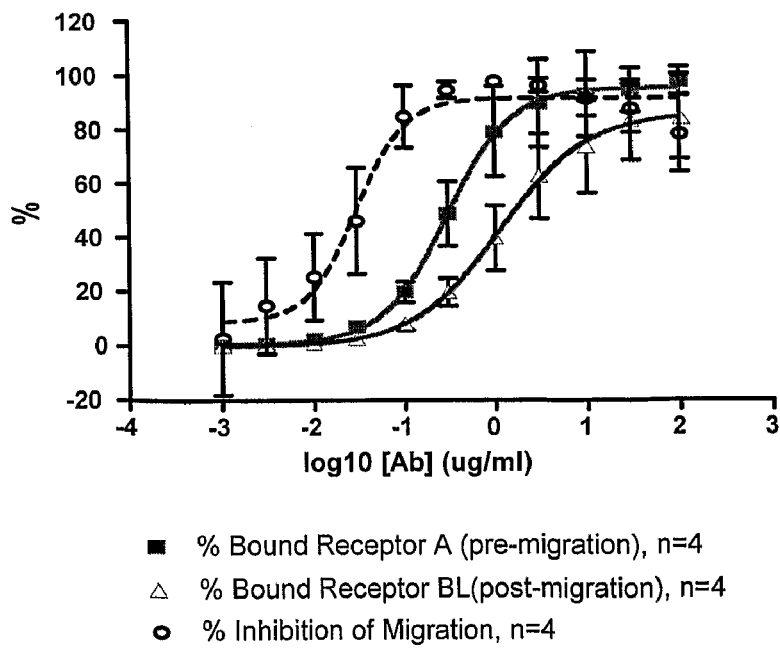

FIG. 21. Relationship observed between level of bound anti-C5aR antibody hAb-Q on human neutrophils (before and after C5a-induced chemotaxis) and inhibition of migration of cells pre-incubated with various concentrations of humanized anti-C5aR antibody hAb-Q.

Figure 22:
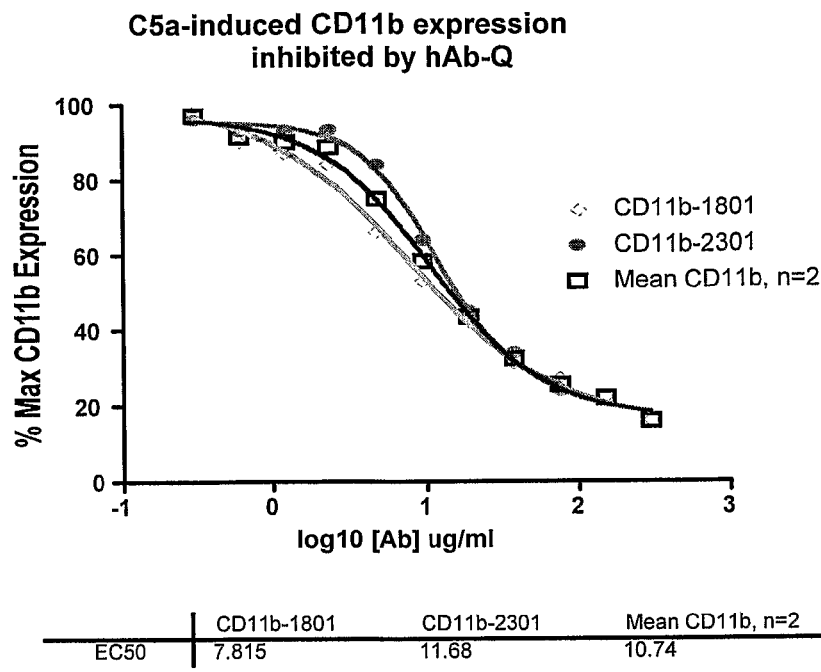

FIG. 22. Inhibition of C5a-induced expression of CD11b on human neutrophils pre-incubated with various concentrations of humanized anti-C5aR antibody hAb-Q.

Figure 23:
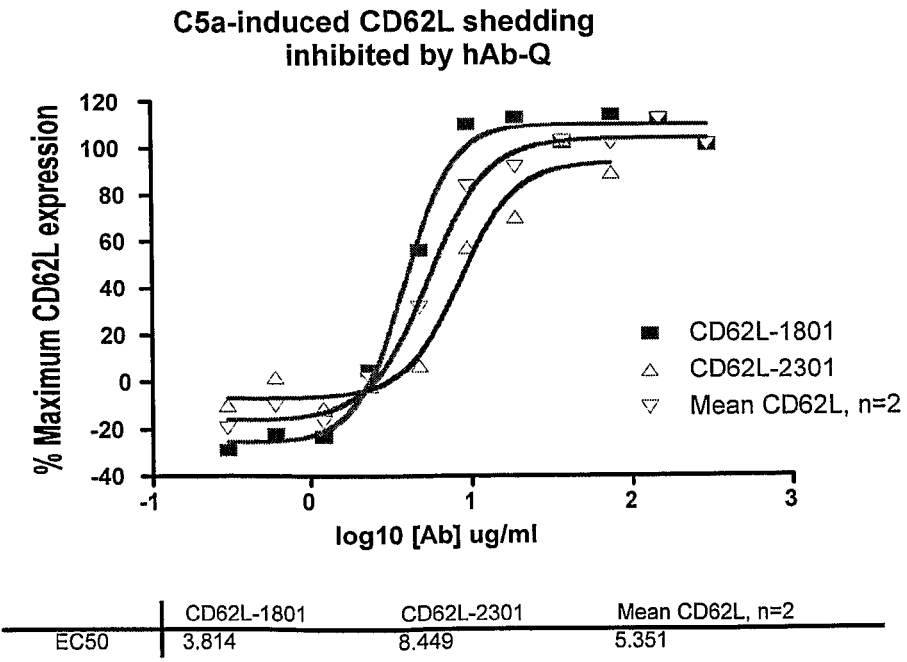

FIG. 23. Inhibition of C5a-induced CD62L down-regulation on human neutrophils pre-incubated with various concentrations of humanized anti-C5aR antibody hAb-Q.

Figure 24:
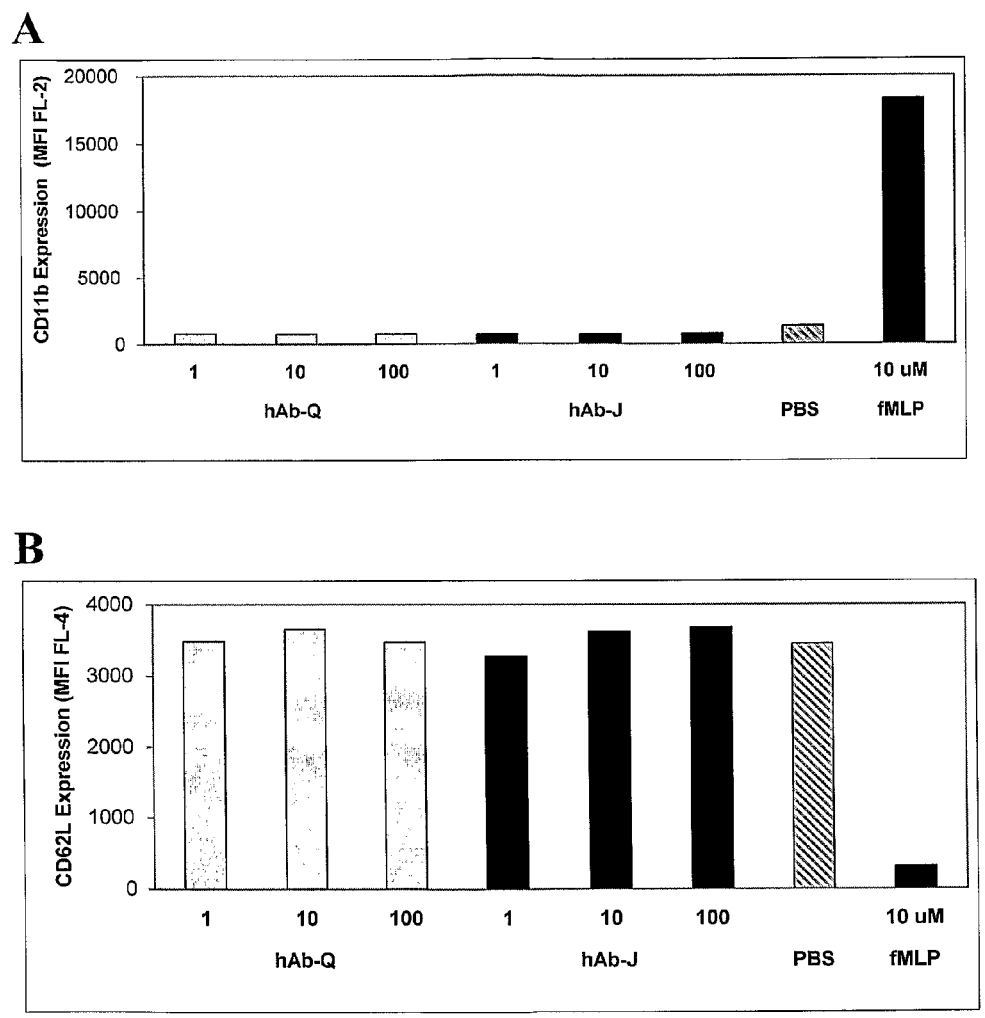

FIG. 24. Expression of CD11b (panel A) and CD62L (panel B) on neutrophils after 1 hour incubation of whole human blood with humanized anti-C5aR antibodies hAb-Q and hAb-J, PBS or the granulocyte activator fMLP.

FIG. 25. Expression of CD11b (panel A) and CD62L (panel B) on neutrophils relative to the PBS control after 20 min incubation of whole human blood with humanized anti-C5aR antibodies hAb-G or hAb-J, or C5a.

FIG. 26. Activation of neutrophils as indicated by changes in relative CD11b expression (panel A) and CD62L expression (panel B) in whole human blood incubated with hAb-Q, hIgG isotype control antibody alone or hIgG antibody plus 100 nM human C5a.

Figure 27:
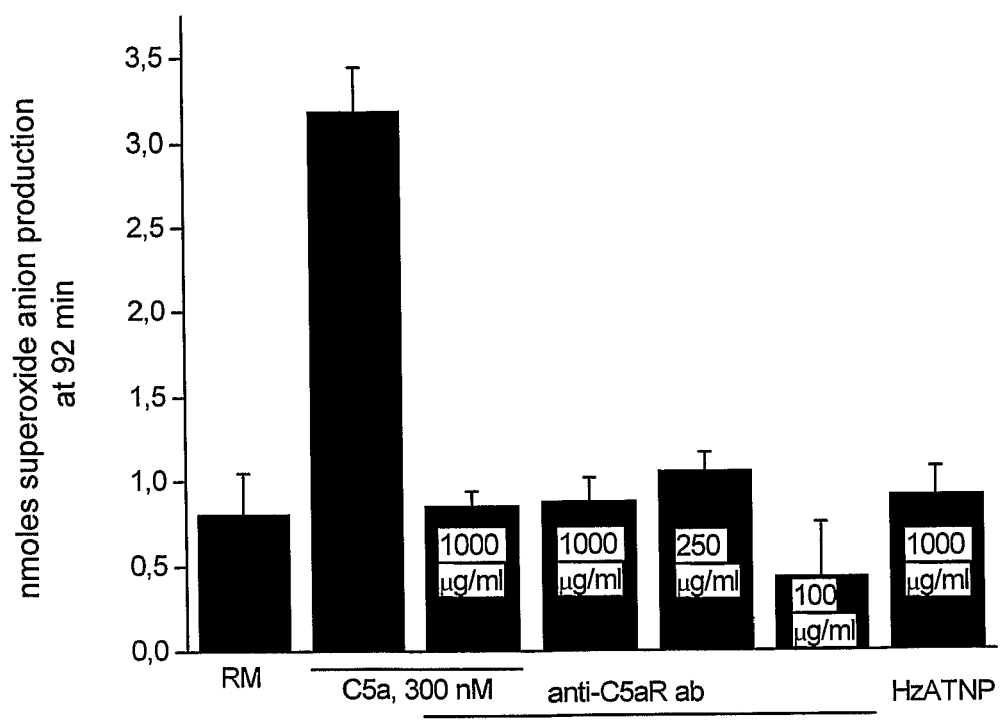

FIG. 27. hAb-Q (referred to as anti-C5aR ab) does not in itself stimulate human neutrophils bound to a solid support to produce superoxide but counteracts the evoked production by C5a.

Figure 28:
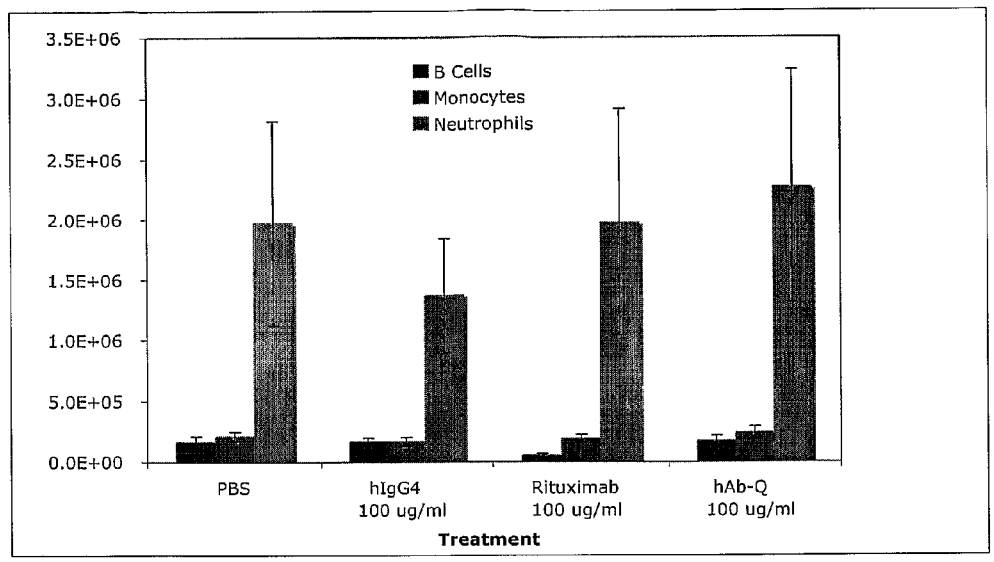

FIG. 28. Average number (±sd) of B cells, monocytes and neutrophils per ml human blood after 4 hr incubation ex vivo with humanized anti-C5aR antibody hAb-Q or controls (rituximab, irrelevant human IgG4, PBS).

Figure 29:
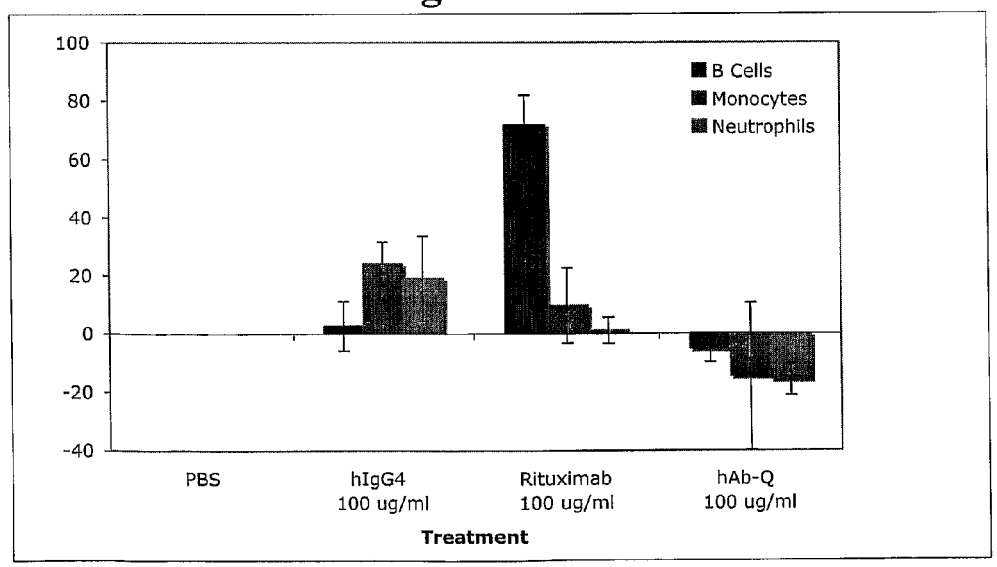

FIG. 29. Average percent depletion (±sd) relative to PBS control of B cells, monocytes and neutrophils per ml human blood after 4 hr incubation ex vivo with humanized anti-C5aR antibody hAb-Q or control antibodies (rituximab, irrelevant human IgG4).

Figure 30:
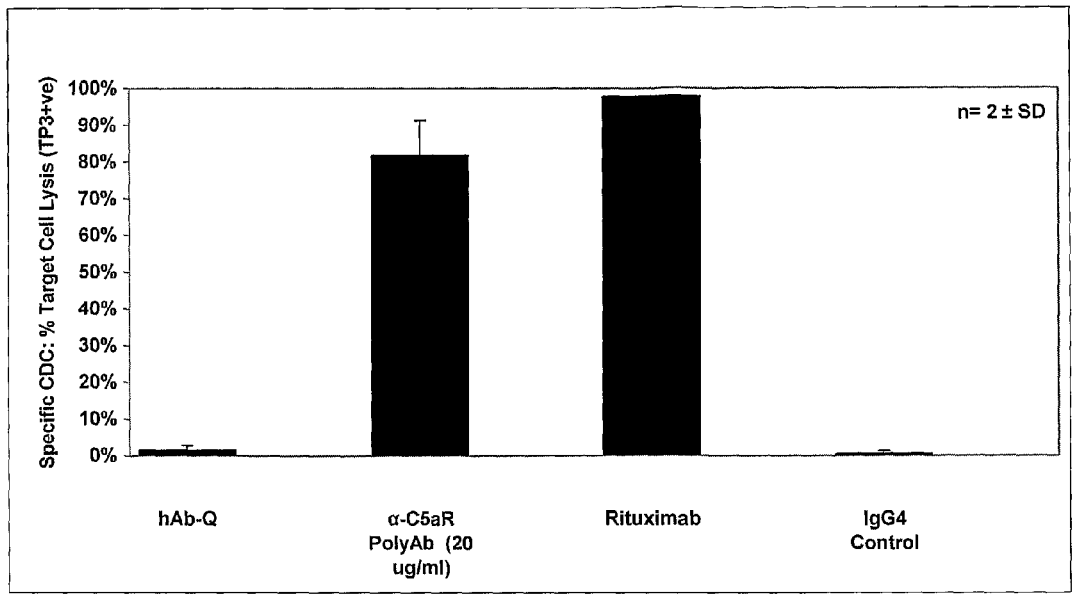

FIG. 30. Specific CDC (% ToPro3+ve (lysed) Ramos E2 cells) after incubation with 100 μg/ml hAb-Q, rituximab and hIgG4 or 20 μg/ml polyclonal anti-C5aR antibody in the presence of 1% rabbit complement.

Figure 31:
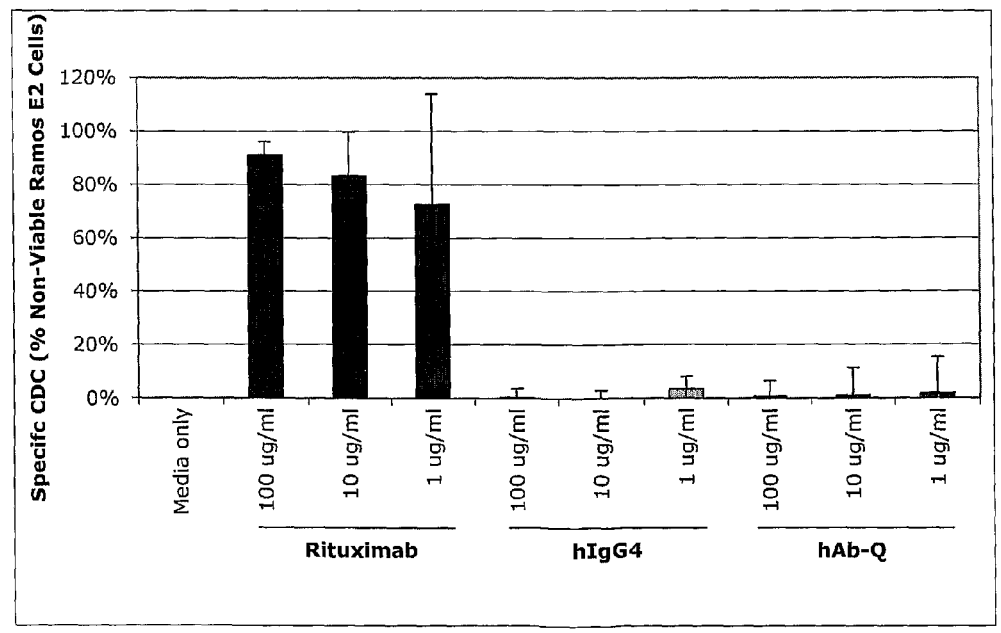

FIG. 31. Specific CDC (% non-viable Ramos E2 cells) after incubation with 1-100 μg/ml hAb-Q, rituximab and hIgG4 in the presence of 10% human serum. Non-specific lysis for each sample incubated with 10% heat-inactivated bovine serum has been subtracted.

Figure 32:
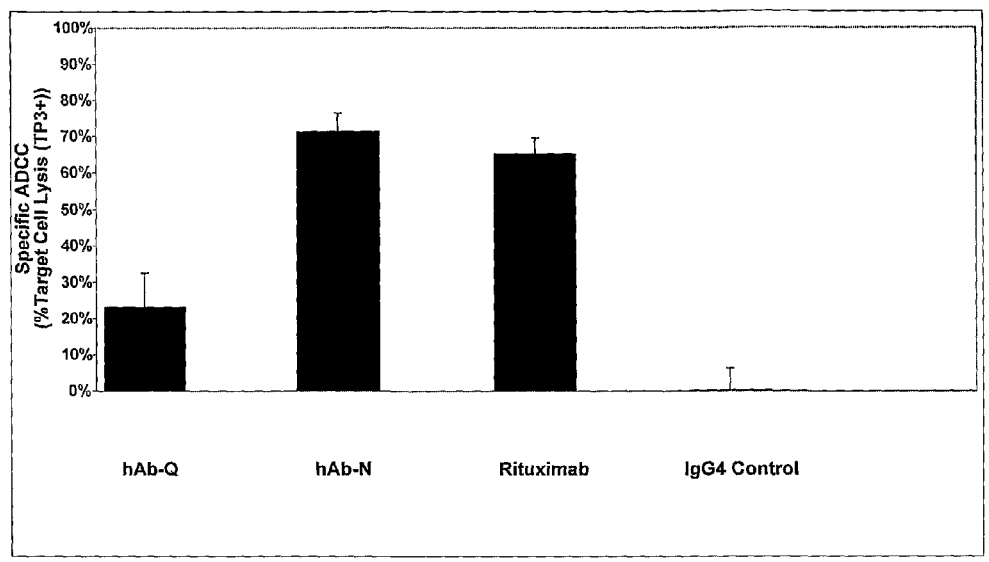

FIG. 32. Specific ADCC (% target cell lysis in 'Target+ Effector' samples after 'Media Only' and 'Target Only' background was subtracted): % non-viable (TP3+ve) Ramos E2 target cells after incubation with human PBMC effector cells plus 100 μg/ml antibody in medium with 10% heat-inactivated fetal calf serum.

Figure 33:
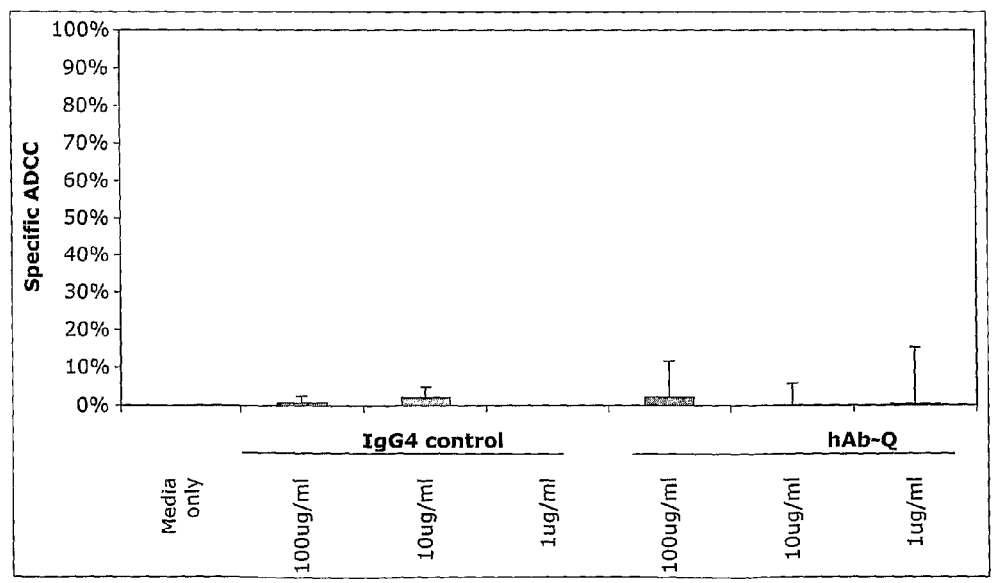

FIG. 33. Specific ADCC (% target cell lysis in 'Target+ Effector' samples after 'Media Only' and 'Target Only' background was subtracted): % non-viable (TP3+ve) Ramos E2 target cells after incubation with human donor PBMC effector cells plus 1-100 μg/ml antibody in medium with 10% human donor serum.

Figure 34:
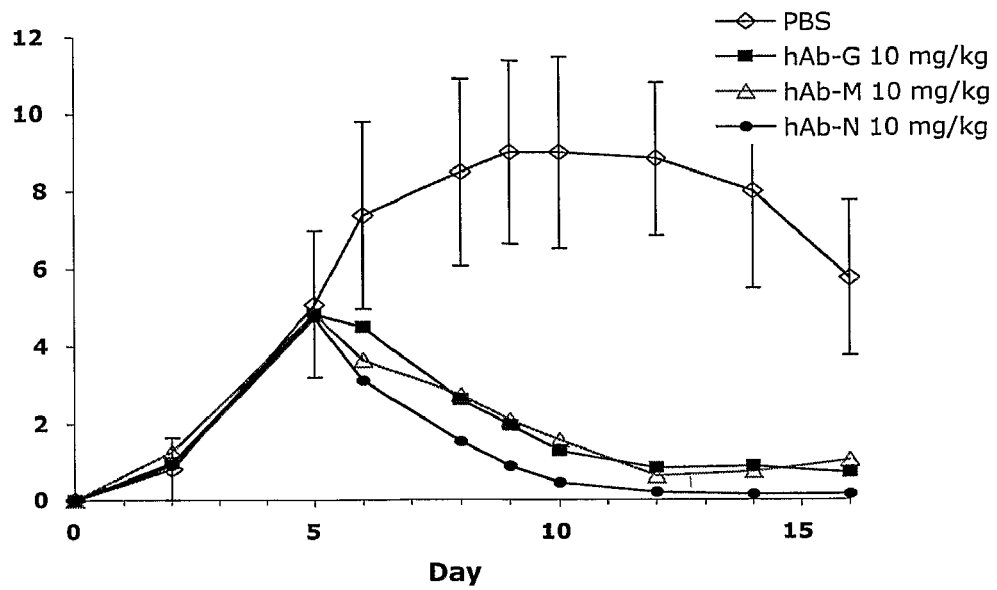

FIG. 34. Disease progression in model of inflammatory arthritis. Reversal of K/BxN serum-induced inflammation in hC5aR knock-in mice (n=6 per group) after i.p. administration of 10 mg/kg anti-hC5aR antibodies G, M and N on day 5 is shown by change in group average clinical scores.

Figure 35:
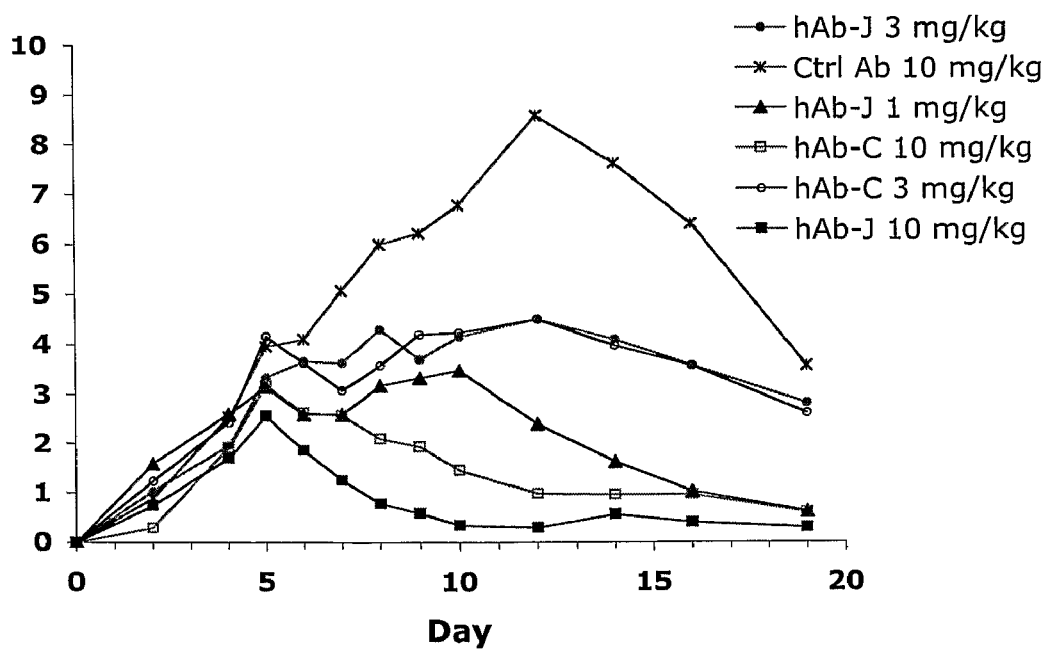

FIG. 35. Disease progression in model of inflammatory arthritis. Reversal of K/BxN serum-induced inflammation in hC5aR knock-in mice (n=4-5 per group) after i.p. administration of 1-10 mg/kg anti-hC5aR antibodies C and J on day 5 is shown by change in group average clinical scores.

Figure 36A:
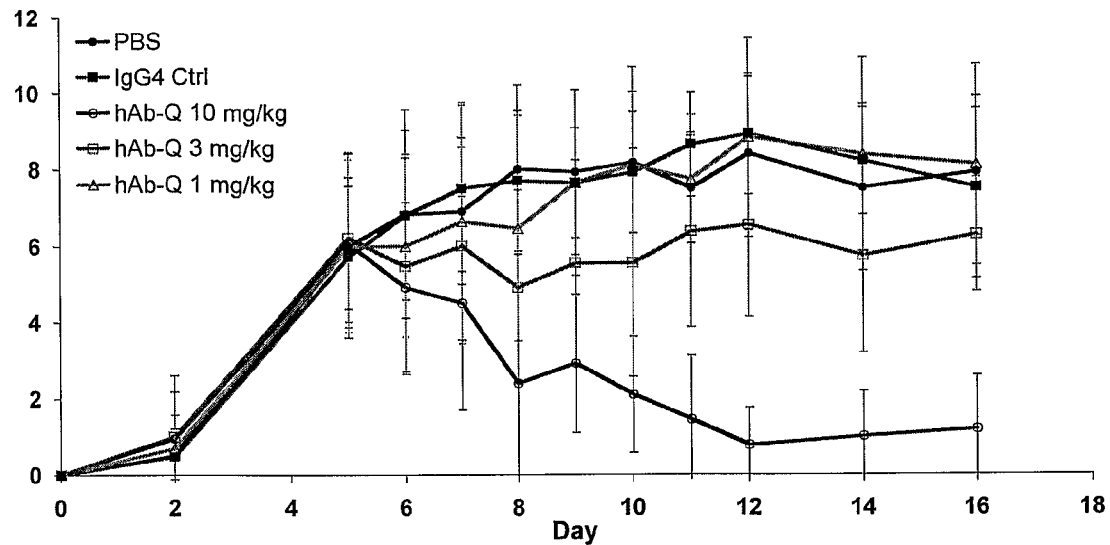
Figure 36B:
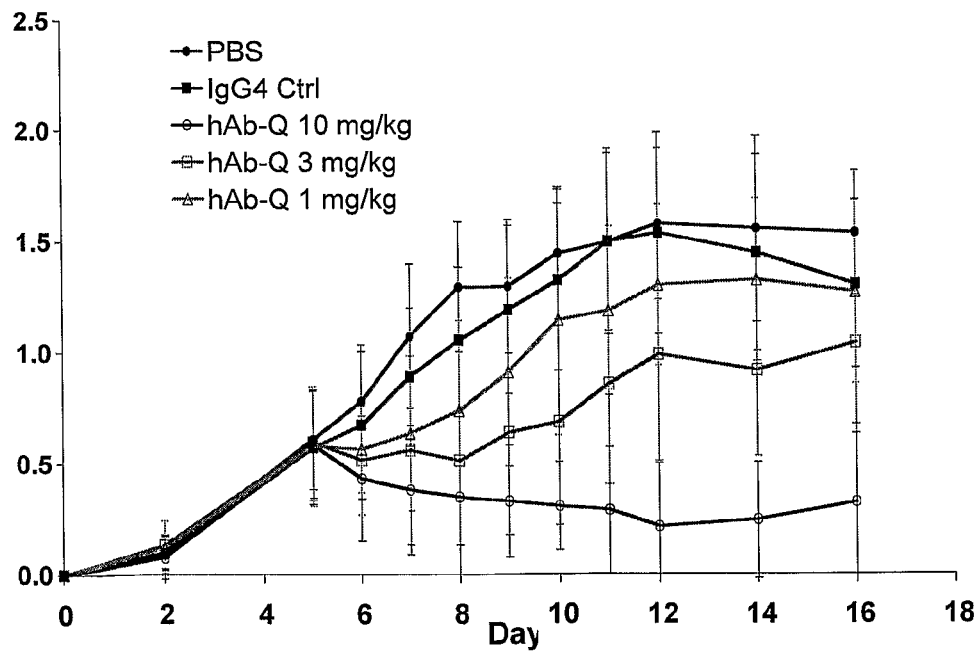

FIG. 36. Disease progression in model of inflammatory arthritis. Reversal of K/BxN serum-induced inflammation in hC5aR knock-in mice (n=10+ per group) after i.p. administration of 1-10 mg/kg hAb-Q on day 5 is shown by change in group average paw size (A) clinical scores (B).

FIG. 37. Level of occupied C5aR over time after in vivo administration of various doses of humanized anti-C5aR antibody, control antibody or PBS.

FIG. 38. Level of free C5aR over time after in vivo administration of various doses of humanized anti-C5aR antibody, control antibody or PBS.

FIG. 39. Serum concentration over time of hAb-Q therapeutically administered on day 5 to mice with inflammation of the joints.

Figure 40:
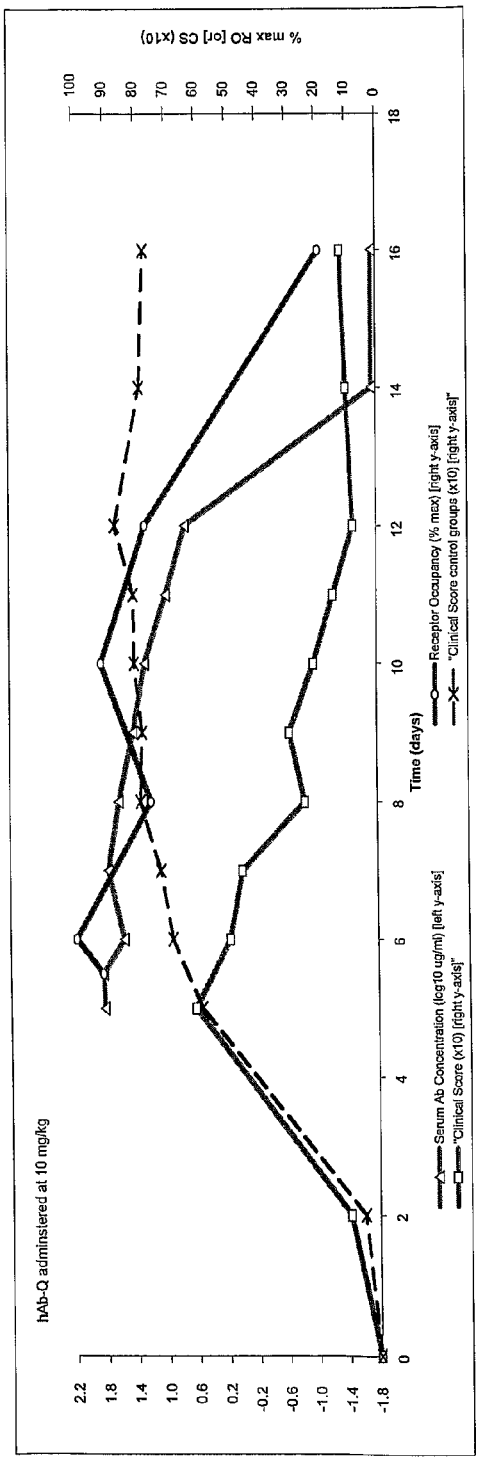

FIG. 40. Relationship between clinical score (level of inflammation in paws and joints), the level of occupied C5a receptor and serum concentration of hAb-Q in mice injected with K/BxN serum on days 0 and 2, and 10 mg/kg humanized anti-C5aR antibody on day 5.

Figure 41:
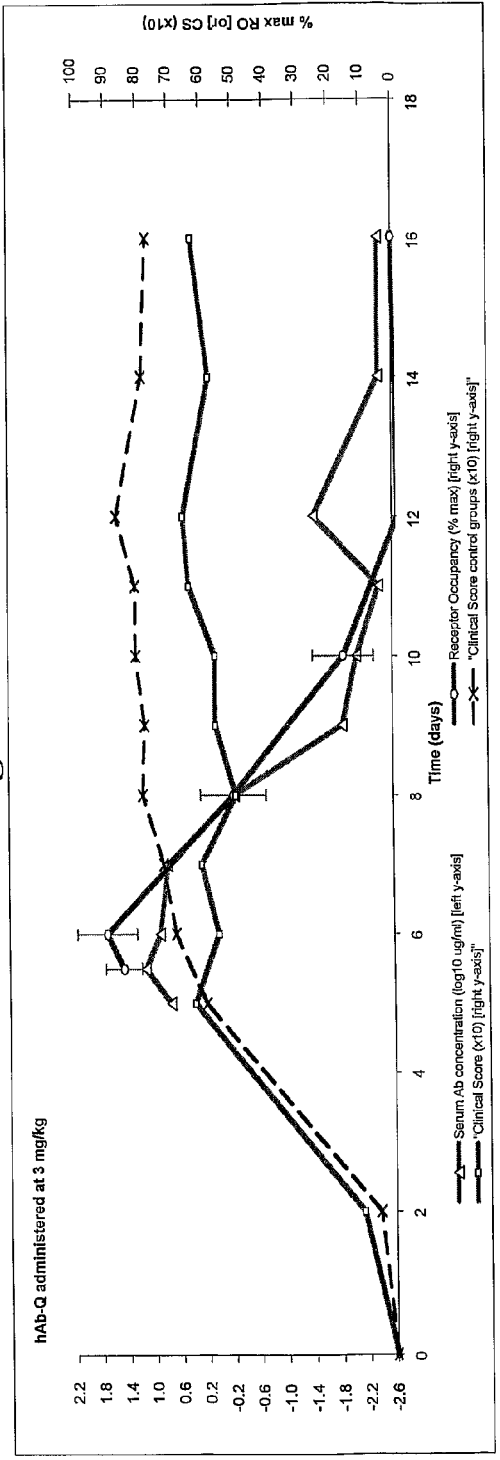

FIG. 41. Relationship between clinical score (level of inflammation in paws and joints), the level of occupied C5a receptor and serum concentration of hAb-Q in mice injected with K/BxN serum on days 0 and 2, and 3 mg/kg humanized anti-C5aR antibody on day 5.

Figure 42:
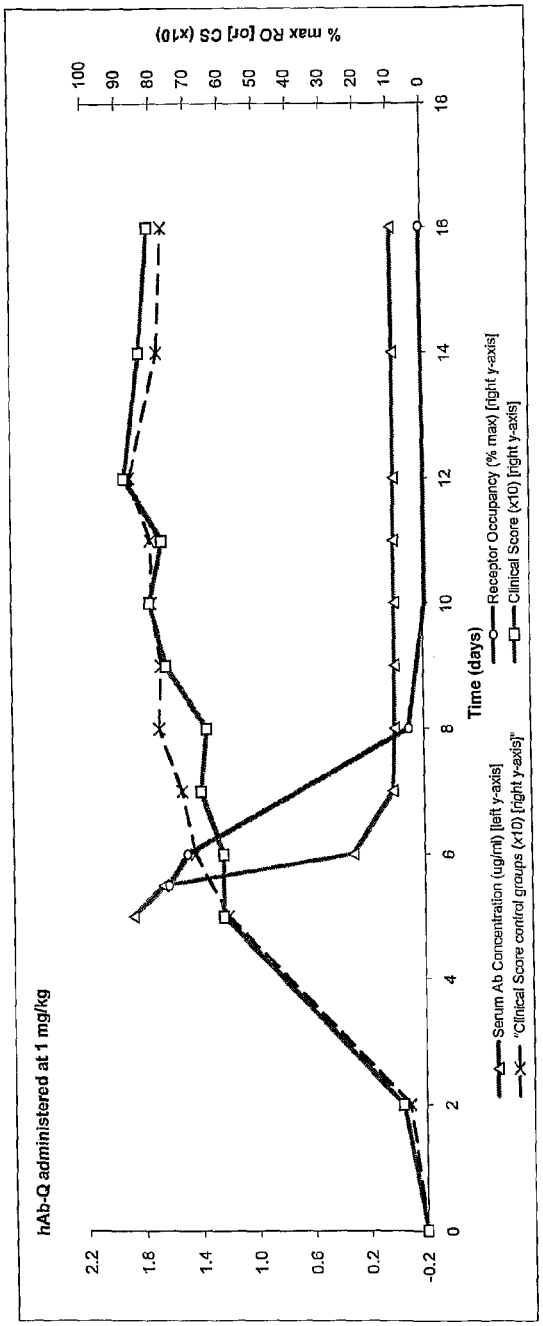

FIG. 42. Relationship between clinical score (level of inflammation in paws and joints), the level of occupied C5a receptor and serum concentration of hAb-Q in mice injected with K/BxN serum on days 0 and 2, and 1 mg/kg humanized anti-C5aR antibody on day 5.

Figure 43:
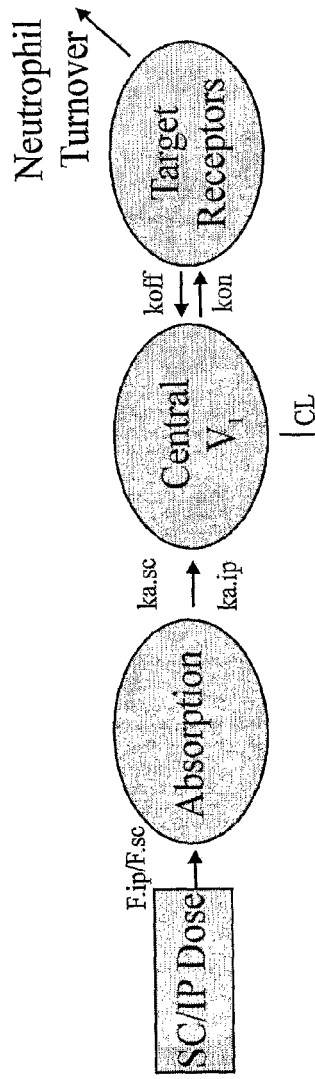

FIG. 43. Schematic representation of the integrated PK/PD model for hAb-Q in a toxicology study and a pharmacology study in transgenic mice.

Figure 44:
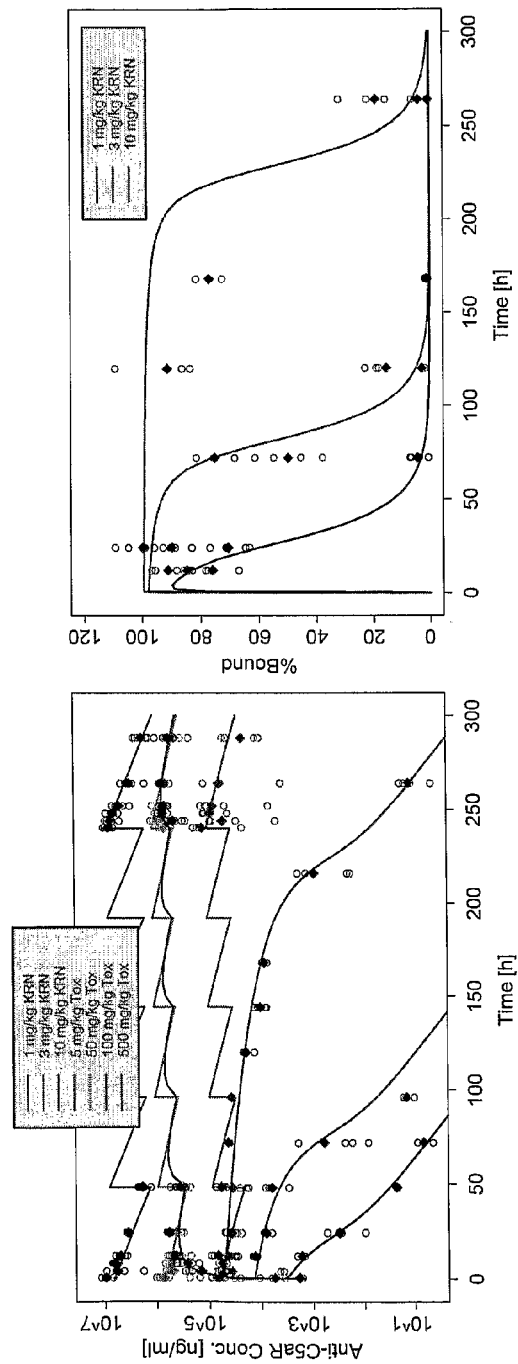

FIG. 44. Model predicted and observed concentration (left) and occupancy (right) vs. time for various i.v., s.c., and i.p. doses of hAb-Q (referred to as anti-C5aR ab) in a toxicology study (denoted Tox in legend) and a pharmacology study (denoted KRN in legend). For the toxicology study PK samples are taken after the dose at day 1 and after the dose at day 43. The day 43 data was assumed to be in steady state, and implemented to follow the $6^{th}$ dose. Average group values: diamonds, individual mice: open circles, model fit via target compartment: thick line.

Figure 45:
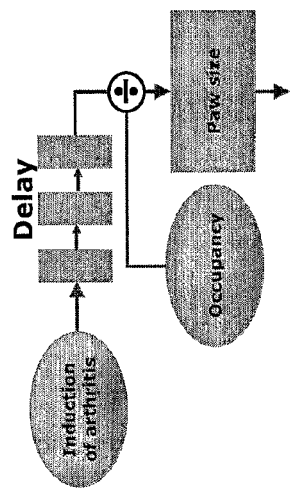

FIG. 45. Schematic representation of the PK/PD model for effect of hAb-Q on inhibition of experimentally induced arthritis in the pharmacology study. This model incorporate the occupancy calculated in the PK/PD model illustrated in FIG. 43.

Figure 46:
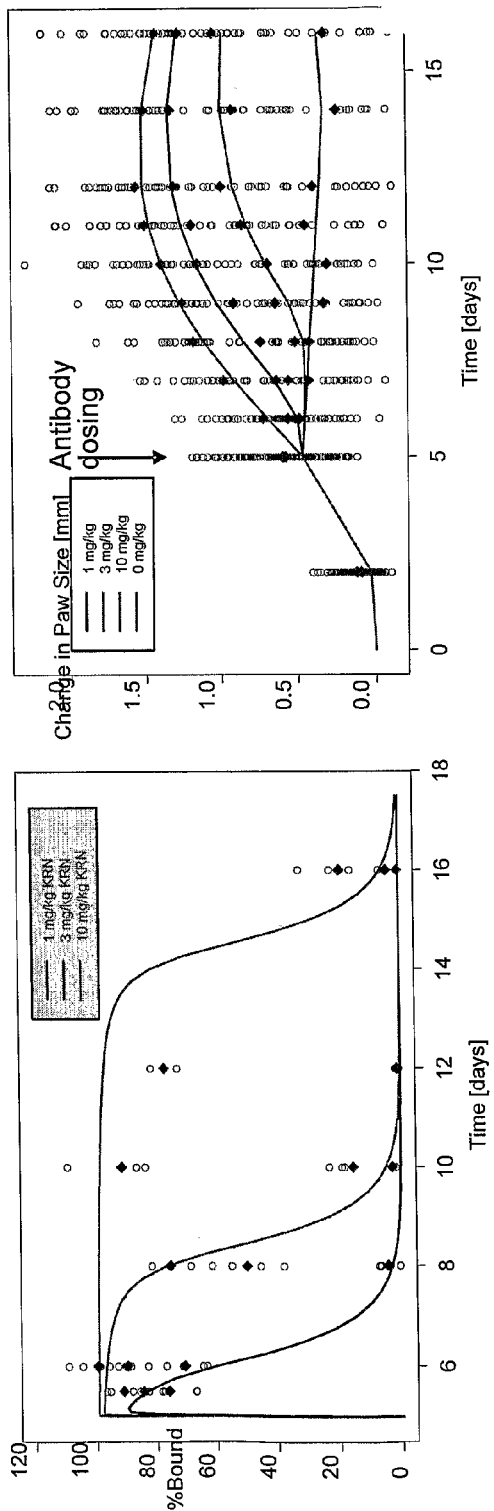

FIG. 46. Occupancy (left) and change in paw size (right) versus time after an inflammatory challenge at day 0, with different i.p. doses of hAb-Q administered on day 5 in transgenic mice. Average group measurements: coloured solid diamonds. Individual mouse values: coloured open circles. Model fit in each group: coloured line.

Figure 47:
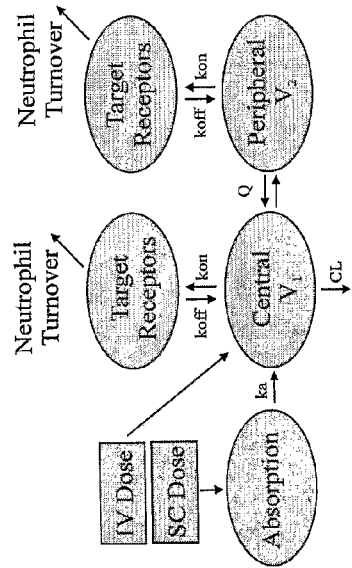

FIG. 47. Schematic representation of the PK/PD model applied for human predictions. The model is composed of a two-compartment model using typical IgG parameters, augmented with target-mediated disposition. $V_1$=central volume. $V_2$=peripheral volume. CL=clearance. Q=distribution clearance. koff/kon=rate constant for association/dissociation. Turnover=Time it takes to renew the target and remove bound antibodies. Two target compartments were used to reflect that target is believed to distribute both inside and outside the blood.

Figure 48:
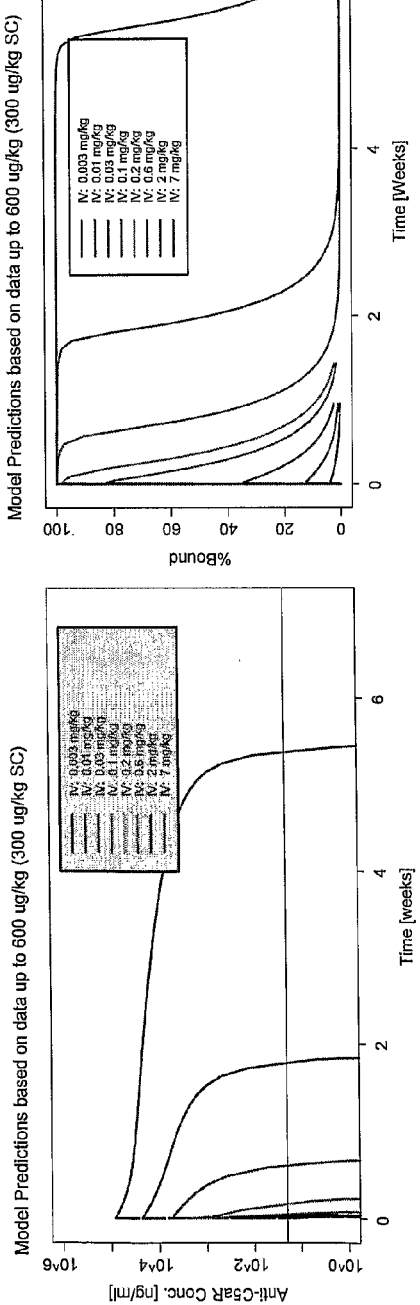

FIG. 48. Model predictions for pharmacokinetics (left) and occupancy (right) following i.v. dosing of anti-C5aR (hAb-Q). Lower limit of quantification is indicated by horizontal line.

Figure 49:
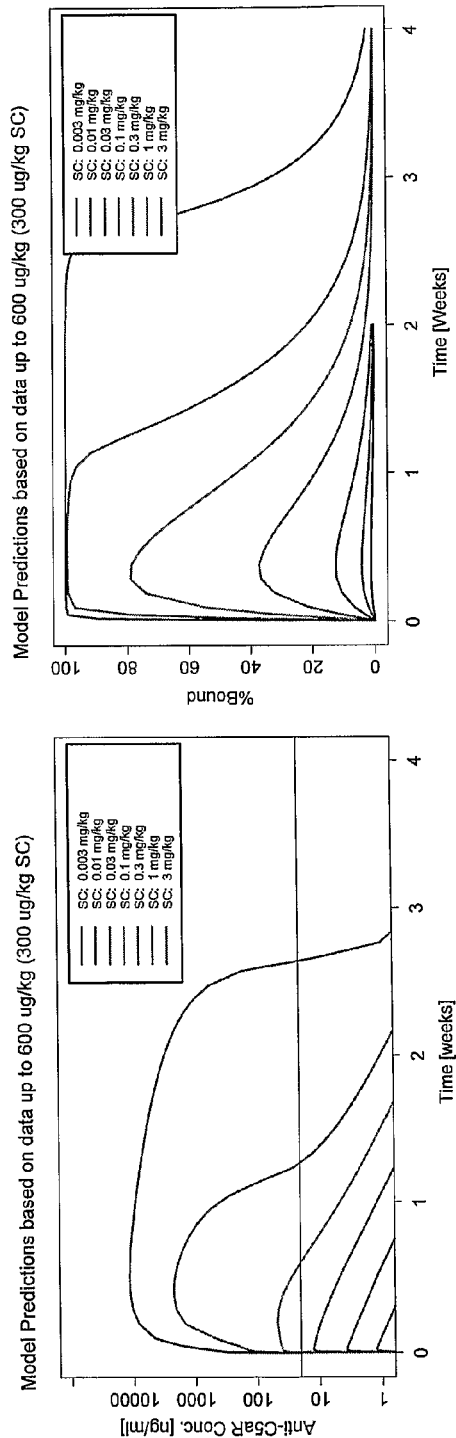

FIG. 49. Model predictions for pharmacokinetics (left) and occupancy (right) following s.c. dosing of Anti-C5aR (hAb-Q). Lower limit of quantification is indicated by horizontal line.

KEY TO THE SEQUENCE LISTING

SEQ ID NO:1—7F3 variable light chain protein sequence.
SEQ ID NO:2—7F3 variable heavy chain protein sequence.
SEQ ID NO:3—7F3 variable light chain coding sequence.
SEQ ID NO:4—7F3 variable heavy chain coding sequence.
SEQ ID NO:5—Human light chain variable region of KV2F_human.
SEQ ID NO:6—Human light chain variable region of KV2E_human.
SEQ ID NO:7—Human light chain variable region of KV2D_human.
SEQ ID NO:8—Human light chain variable region of KV2B_human.
SEQ ID NO:9—Human light chain variable region of KV2A_human.
SEQ ID NO:10—Human light chain variable region of X12691.
SEQ ID NO:11—Human light chain variable region of U41645.
SEQ ID NO:12—Human light chain variable region of U41644.
SEQ ID NO:13—Human light chain variable region of M31952.
SEQ ID NO:14—hVkFW Cons consensus sequence of human light chain variable sequences as provided in FIG. 1.
SEQ ID NO:15—Human heavy chain variable region of Hv1Av_human.
SEQ ID NO:16—Human heavy chain variable region of Hv1Bv_human.
SEQ ID NO:17—Human heavy chain variable region of Hv1Cv_human.
SEQ ID NO:18—Human heavy chain variable region of Hv1Gv_human.
SEQ ID NO:19—Human heavy chain variable region of M99641.aa.
SEQ ID NO:20—Human heavy chain variable region of M99642.aa.
SEQ ID NO:21—Human heavy chain variable region of X62109.aa.
SEQ ID NO:22—Human heavy chain variable region of X92343.aa.
SEQ ID NO:23—Human heavy chain variable region of Z12305.aa.
SEQ ID NO:24—hVhvFW Cons consensus sequence of human heavy chain variable (V) region sequences as provided in FIG. 2A.
SEQ ID NO:25—Human heavy chain joining region of Hv1Cj_human.
SEQ ID NO:26—Human heavy chain joining region of Hv2Ij_human.
SEQ ID NO:27—Human heavy chain joining region of Hv3Hj_human.
SEQ ID NO:28—Human heavy chain joining region of Hv3Kj_human.
SEQ ID NO:29—Human heavy chain joining region of Hv3Tj_human.
SEQ ID NO:30—hVhjFW Cons consensus sequence of human heavy chain joining (J) region sequences as provided in FIG. 2B.
SEQ ID NO:31—Humanized 7F3 V region light chain h7Vk amino acid sequence.
SEQ ID NO:32—Humanized 7F3 V region light chain h7aVk amino acid sequence.
SEQ ID NO:33—Humanized 7F3 V region light chain h7bVk amino acid sequence.
SEQ ID NO:34—Humanized 7F3 V region heavy chain h7Vh amino acid sequence.
SEQ ID NO:35—Humanized 7F3 V region heavy chain h7aVh amino acid sequence.
SEQ ID NO:36—Humanized 7F3 V region heavy chain h7bVh amino acid sequence.
SEQ ID NO:37—Human C5aR.
SEQ ID NO:38—Epitope on the second extracellular loop of human C5aR.
SEQ ID NO: 39—h7F3VhCons consensus sequence of humanized 7F3 heavy chain variable regions of the invention as provided in FIG. 10.
SEQ ID NO:40—Human light chain constant region hCκ-R.
SEQ ID NO:41—Human light chain constant region hCκ.
SEQ ID NO:42—Human heavy chain constant region hCγ4.
SEQ ID NO:43—Human heavy chain constant region hCγ4$_{PE}$.
SEQ ID NO:44—Human heavy chain constant region hCγ1.
SEQ ID NO:45—Human heavy chain constant region hCγ4$_P$.
SEQ ID NO:46—Humanized RNOK203VL sequence.
SEQ ID NO:47—KV2F-HUMAN derived VLCD18-Q sequence.
SEQ ID NO:48—h7F3VkCons consensus sequence of humanized 7F3 light chain variable regions of the invention as provided in FIG. 6.
SEQ ID NO:49—hVhFW Cons consensus human heavy chain VJ framework sequence
SEQ ID NO:50—Human SGI-VH sequence.
SEQ ID NO:51—Human germline HG3 sequence.
SEQ ID NO:52—Polynucleotide sequence encoding humanized 7F3 V region light chain h7Vk amino acid sequence.
SEQ ID NO:53—Polynucleotide sequence encoding humanized 7F3 V region light chain h7aVk amino acid sequence.
SEQ ID NO:54—Polynucleotide sequence encoding humanized 7F3 V region light chain h7bVk amino acid sequence.
SEQ ID NO:55—Polynucleotide sequence encoding humanized 7F3 V region heavy chain h7Vh amino acid sequence.
SEQ ID NO:56—Polynucleotide sequence encoding humanized 7F3 V region heavy chain h7aVh amino acid sequence.
SEQ ID NO:57—Polynucleotide sequence encoding humanized 7F3 V region heavy chain h7bVh amino acid sequence.
SEQ ID NO:58—Fragment of the second extracellular loop of human C5aR.
SEQ ID NO:59—Fragment of the N-terminal extracellular domain of human C5aR.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, antibody technology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Selected Definitions

As used herein, "C5a receptor", "C5aR", "C5aR1" or "human C5aR" and variations thereof refers to the human complement component 5 receptor 1 which is also known in the art as the C5a anaphylatoxin receptor and the CD88 antigen. C5aR belongs to the family of seven transmembrane G-protein-coupled receptors, and binds C5a (Gerard and Gerard, 1991). An example of the amino acid sequence of a human C5aR is provided in SEQ ID NO:37, however, as the skilled person will be aware there are naturally occurring allelic variants of this molecule which are also encompassed by the term "C5aR". The various domains of human C5aR are defined as follows:

| amino acids | 1-37 | extracellular domain - N-terminus |
| amino acids | 38-61 | transmembrane domain |
| amino acids | 62-71 | intracellular domain |
| amino acids | 72-94 | transmembrane domain |
| amino acids | 95-110 | extracellular domain - extracellular loop 1 |
| amino acids | 111-132 | transmembrane domain |
| amino acids | 133-149 | intracellular domain |
| amino acids | 150-174 | transmembrane domain |
| amino acids | 175-206 | extracellular domain - extracellular loop 2 |
| amino acids | 207-227 | transmembrane domain |
| amino acids | 228-242 | intracellular domain |
| amino acids | 243-264 | transmembrane domain |
| amino acids | 265-283 | extracellular domain - extracellular loop 3 |
| amino acids | 284-307 | transmembrane domain |
| amino acids | 308-350 | intracellular domain - C-terminus. |

The term "subject" as used herein is intended to mean any animal, in particular mammals, such as humans, horses, cows, cats and dogs, and may, where appropriate, be used interchangeably with the term "patient". Preferably, the subject is a human.

As used herein the terms "treating", "treat" or "treatment" and variations thereof include administering a therapeutically effective amount of an antibody of the invention sufficient to reduce or eliminate at least one symptom of the disorder.

As used herein the terms "preventing", "prevent" or "prevention" or variations thereof refers to protecting a subject from developing at least one symptom of a disease, or reducing the severity of a symptom of a disorder.

As used herein, the term "exposing the cell" refers to providing the antibody such that it is able to contact/bind human C5aR providing that C5aR is present on the cell.

The term "effective concentration 50%" (abbreviated as "$EC_{50}$") represents the concentration of an antibody of the invention that is required for 50% of a given effect of the molecule the antibody targets (e.g. inhibiting/displacing binding of human C5a to human C5aR). It will be understood by one in the art that a lower $EC_{50}$ value corresponds to a more potent antibody.

As used herein, the term "inhibiting" refers to reducing, and possibly completely abolishing, the defined activity. Preferably, the defined activity is reduced by at least 50%, more preferably at least 75% and even more preferably at least 90%.

As used herein, the term "about" refers to a range of +/−5% of the specified value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. In an embodiment, a molecule "consists essentially of" the defined sequence. In another embodiment, a molecule "consists of" the defined sequence.

Humanized Anti-C5aR Antibodies

The term immunoglobulin refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized, see for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region (abbreviated herein as $C_H$). The heavy chain constant region typically is comprised of three domains, $C_H1$, $C_H2$, and $C_H3$. Each light chain typically is comprised of a light chain variable region (abbreviated herein as $V_L$) and a light chain constant region (abbreviated herein as $C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). In a preferred embodiment, an antibody of the invention at least comprises a $V_L$ domain and a $V_H$ domain.

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk, 1987). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain.

The term "humanized antibody", as used herein, refers to herein an antibody derived from a non-human antibody, typically murine, that retains or substantially retains the antigen-binding properties of the parent antibody but which is less immunogenic in humans. Due the the antibodies of the invention being defined by structural and functional features, the term "humanized antibody" is used interchangeably with "antibody".

The term complementarity determining region (CDR), as used herein, refers to amino acid sequences which together define the binding affinity and specificity of a variable fragment (Fv) region of a immunoglobulin binding site.

The term framework region (FR), as used herein, refers to amino acid sequences interposed between CDRs. These portions of the antibody serve to hold the CDRs in appropriate orientation (allows for CDRs to bind antigen). A variable region, either light or heavy, comprises a framework and typically three CDRs.

The term constant region (CR) as used herein, refers to the portion of the antibody molecule which confers effector functions. The constant regions of the subject humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Preferred heavy chain constant regions are gamma 1 (IgG1), gamma 2 (IgG2), gamma 3 (IgG3) and gamma 4 (IgG4), more preferably gamma 4 (IgG4). More preferred is a fragment crystallizable (Fc) region of the gamma 4 (IgG4) isotype with mutations Ser228Pro (referred to as "P" mutation) and/or Leu235Glu (referred to as "E" mutation). Particularly preferred heavy chain constant region sequences are provided as SEQ ID NO's 42 to 45. The light chain constant region can be of the kappa or lambda type, preferably of the kappa type. Particularly preferred light chain constant region sequences are provided as SEQ ID NO's 40 and 41.

In a preferred embodiment, an immunoglobulin light chain variable region described herein is joined directly to an immunoglobulin light chain constant region described herein. Similarly, in a further preferred embodiment an immunoglobulin heavy chain variable region described herein is joined directly to an immunoglobulin heavy chain constant region described herein. Thus, in a preferred embodiment, the C-terminus of the amino acid sequence provided as SEQ ID NO:31 is directly joined to the N-terminus of the amino acid sequence provided as SEQ ID NO:41, and the the C-terminus of the amino acid sequence provided as SEQ ID NO:36 is directly joined to the N-terminus of the amino acid sequence provided as SEQ ID NO:45.

A skilled person will understand that the variable and constant regions of an immunoglobulin heavy or light chain can be joined as described by using standard recombinant DNA technology to create a polynucleotide (encoding the joined variable and constant domains) that can be expressed in a suitable host (to produce the said immunoglobuin chain(s)) or by using peptide chemistry to synthesise the joined variable and constant domains.

Humanized antibodies of the invention retain a significant proportion of the binding properties of the parent antibody, namely monoclonal antibody designated 7F3 produced by the hydridoma deposited on 6 Nov. 2000 with ECACC under accession number 00110609. In particular, humanized antibodies of the invention retain the ability to specifically bind the antigen recognized by the parent antibody used to produce such humanized antibody. Preferably the humanized antibody exhibits the same or substantially the same antigen-binding affinity and avidity as the parent antibody. Ideally, the affinity ($K_D$) of the antibody will not be greater than 10 times that of the parent antibody affinity, more preferably not greater than about 5 times and most preferably the affinity will not be greater than three times that of the parent antibody. Methods for assaying antigen-binding affinity are well known in the art and include half-maximal binding assays, competition assays, and Scatchard analysis. Suitable antigen binding assays are described in this application (see, for instance, Example 3).

As the skilled person will appreciate, "avidity" relates to the overall strength of interaction between two molecules, such as an antibody and antigen. Avidity depends on both the affinity and the valency of interactions. Furthermore, "affinity" relates to the strength of the binding between a single binding site of a molecule (e.g., an antibody) and a ligand (e.g., an antigen). The affinity of a molecule X for a ligand Y is represented by the dissociation constant ($K_d$), which is the concentration of Y that is required to occupy the combining sites of half the X molecules present in a solution. A smaller $K_d$ indicates a stronger or higher affinity interaction, and a lower concentration of ligand is needed to occupy the sites.

The term "humanized antibody" or "antibody" as used in this invention includes intact molecules as well as fragments thereof, such as Fab, F(ab')2, and Fv which are capable of binding the epitopic determinant. These antibody fragments retain some ability to selectively bind to human C5aR, examples of which include, but are not limited to, the following:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc which may or may not be polyspecific (see, for example, WO 94/07921 and WO 98/44001) and (6) Single domain antibody, typically a variable heavy domain devoid of a light chain.

Humanized antibody fragments include separate heavy chains, light chains, Fab, Fab', F(ab')2, Fc, a variable light domain devoid of any heavy chain, a variable heavy domain devoid of a light chain and Fv. Fragments are produced by recombinant DNA techniques, or by enzymatic or chemical separation of intact immunoglobulins.

A "humanized antibody" or antibody of the invention may also be a heteroconjugate antibody. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 586505). It is contemplated that the antibodies may be prepared in vitro using known methods in synthetic protein chemistry, including those involving crosslinking agents.

It may be desirable to modify an antibody of the invention with respect to effector function, so as to enhance, e.g., the effectiveness of the antibody in treating a disorder described herein such as arthritis. For example, cysteine residue(s) may be introduced into the Fc region, thereby allowing interchain disulfide bond formation in this region. The homodimeric humanized antibody thus generated may have improved internalization capability and/or increased complement-mediated cell killing and antibody-dependent cellular cytotoxicity (ADCC) (Caron et al., 1992; Shopes, 1992). Homodimeric antibodies with enhanced activity may also be prepared using heterobifunctional cross-linkers as described in Wolff et al. (1993). Alternatively, an antibody can be engineered that has dual Fc regions and may thereby have enhanced complement lysis and ADCC capabilities (Stevenson et al., 1989).

As used herein, a "non-depleting antibody" refers to an antibody that binds to its target but does not recruit the immune system's effector functions which effect target cell lysis. The immune system's effector functions are dependent on interactions of the Fc-domain with C1q, the first component of the complement cascade, and/or receptors (FcR). Complement-dependent cytotoxicity (CDC) is initiated by multiple Fc-domains interacting with C1q, which can ultimately result in lysis of target cells through the formation of the membrane attack complex (MAC). Additionally, cells of the immune system, such as granulocytes, macrophages, and NK cells, may interact via FcRs with mAbs bound to target cells. Lysis of target cells is triggered via antibody-dependent cell mediated cytotoxicity (ADCC) or phagocytosis. Non-depleting antibodies include antibody fragments without an Fc domain, including for example, monovalent (e.g., Fab, scFv, nanobodies and dAbs), bivalent (e.g., F(ab')$_2$ and diabodies) and multivalent (e.g., triabodies and pentabodies) formats. In addition, non-depleting antibodies include antibodies that have been modified to remove effector functions without impacting pharmokinetics, for example, amino acid residues in the Fc-domain that play a dominant role in interaction with C1q and FcRs could be modified, or the N-linked glycosylation site in the CH2 domain could be removed. As a skilled person is aware, the chances of engineering a non-depleting antibody are linked to the constant region used to produce the antibody. An IgG3 constant region is more likely to produce a depleting antibody than an IgG1 constant region which in turn is more likely to produce a depleting antibody than an IgG2 constant region, whereas an IgG4 constant region will generally mean that the antibody is non-depleting. A skilled person would also understand that modifications to a constant region could convert a depleting antibody into a non-depleting antibody and vice versa.

As used herein, a "non-activating antibody" refers to antibodies that bind cell surface receptors and negate or block the action of endogenous ligands The humanized antibodies of the invention are produced by the intervention of man. Thus, they are not expected to occur in nature. Nonetheless, in a preferred embodiment, an antibody or immunoglobulin chain of the invention is "substantially purified" or "purified". By "substantially purified" or "purified" we mean an antibody that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. In another embodiment, "substantially purified" or "purified" means that the molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition).

The term "recombinant" in the context of an antibody or immunoglobulin chain refers to the antibody or immunoglobulin chain when produced by a cell, or in a cell-free expression system, in an altered amount or at an altered rate compared to its native state. In one embodiment, the cell is a cell that does not naturally produce the antibody or immunoglobulin chain. However, the cell may be a cell which comprises a non-endogenous gene that causes an altered, preferably increased, amount of the polypeptide to be produced. A recombinant antibody or immunoglobulin chain of the invention includes polypeptides which have not been separated from other components of the transgenic (recombinant) cell, or cell-free expression system, in which it is produced, and an antibody or immunoglobulin chain produced in such cells or cell-free systems which are subsequently purified away from at least some other components.

The % identity of a polypeptide (immunoglobulin chain) is determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids. Most preferably, the two sequences are aligned over their entire length.

With regard to a defined immunoglobulin chain, it will be appreciated that % identity figures higher than those provided above will encompass preferred embodiments. Thus, where applicable, in light of the minimum % identity figures, it is preferred that the immunoglobulin chain comprises an amino acid sequence which is at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In another embodiment, one residue is added to the nominated SEQ ID NO, one residue is deleted from the nominated SEQ ID NO, one residue is added and one residue is deleted compared to the nominated SEQ ID NO, two residues are added to the nominated SEQ ID NO, two residues are deleted from the nominated SEQ ID NO, one residue is changed from the nominated SEQ ID NO, two residues are changed from the nominated SEQ ID NO, one residue is changed and one residue is deleted from the nominated SEQ ID NO, or one residue is changed and one residue is added to the nominated SEQ ID NO, or any combination thereof.

In a preferred embodiment, there are no gaps in the alignment. More specifically, the algorithm does not need to create a gap in a contiguous stretch of amino acids to obtain an optimal (highest % identity) alignment.

Amino acid sequence mutants of the antibody and/or immunoglobulin chain of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. Products derived from mutated/altered DNA can readily be screened using techniques described herein to determine if they have receptor-binding and/or -inhibitory activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the antibody and/or immunoglobulin chain molecule removed and a different residue inserted in its place. The sites of greatest interest for substitutional mutagenesis include sites identified as important for antigen binding. These sites, especially those falling within a sequence of at least three other identically conserved sites of human antibodies and/or immunoglobulin chains, are preferably substituted in a relatively conservative manner. Such conservative substitutions are shown in Table 1 under the heading of "exemplary substitutions". Specific examples of substitutions are provided in FIGS. 6 and 10, where an amino acid at a given site can be substituted with another amino acid present at the same site in other humanized chain.

TABLE 1

Exemplary substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Furthermore, if desired, unnatural amino acids or chemical amino acid analogues can be introduced as a substitution or addition into the antibody and/or immunoglobulin chain of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Polypeptides of the present invention can be produced in a variety of ways, including production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides and Expression thereof

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the terms "nucleic acid" and "genetic material".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The present invention relates to a polynucleotide encoding one or more of SEQ ID NO:31, SEQ ID NO:32, SEQ ID NO:33, SEQ ID NO:48, SEQ ID NO:34, SEQ ID NO:35, SEQ ID NO:36 and SEQ ID NO:39, and/or a polynucleotide which is at least 67% identical to a polynucleotide encoding one or more of SEQ ID NO:31, SEQ ID NO:32, SEQ ID NO:33, SEQ ID NO:48, SEQ ID NO:34, SEQ ID NO:35, SEQ ID NO:36 and SEQ ID NO:39. Examples of such polynucleotides include, but are not limited to, those comprising a sequence as provided in any one of SEQ ID NO's 52 to 57.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 100 nucleotides in length, and the GAP analysis aligns the two sequences over a region of at least 100 nucleotides. Most preferably, the two sequences are aligned over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

The present invention also relates to a polynucleotide which hybridizes under stringent conditions to a polynucleotide encoding one or more of SEQ ID NO:31, SEQ ID NO:32, SEQ ID NO:33, SEQ ID NO:48, SEQ ID NO:34, SEQ ID NO:35, SEQ ID NO:36 and SEQ ID NO:39. The term "stringent hybridization conditions" or "stringent conditions" and the like as used herein refers to parameters with which the art is familiar, including the variation of the hybridization temperature with length of an polynucleotide or oligonucleotide. Nucleic acid hybridization parameters may be found in references which compile such methods, Sambrook, et al., (supra), and Ausubel, et al., (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA) and washing twice in 0.2×SSC, 0.1% SDS at 65° C., with each wash step being about 30 min.

Antibodies and immunoglobulin chains of the invention are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the antibodies and/or immunoglobulin chains.

These expression vectors are typically replicable in the host cells either as episomes or as an integral part of the host chromosomal DNA. Commonly, expression vectors contain selection markers (e.g., ampicillin-resistance, hygromycin-resistance, tetracycline resistance, neomycin resistance, G418-resistance, DHFR (dihydrofolate reductase), ADA (adenosine deaminase), GS (glutamine synthetase)) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, a T7 promoter or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Another example of yeast useful for expression is *Pichia pastoris*.

In addition to microorganisms, mammalian tissue cell culture may also be used to express and produce the antibodies and/or immunoglobulin chains of the present invention (e.g., polynucleotides encoding immunoglobulins or fragments thereof) (see Winnacker, From Genes to Clones, VCH Publishers, N.Y., N.Y. (1987)). Eukaryotic cells are actually preferred, because a number of suitable host cell lines capable of secreting heterologous proteins (e.g., intact immunoglobulins) have been developed in the art, and include CHO cell lines, various Cos cell lines, NSO cells, HEK293 cells, PerC6 cells, HeLa cells, preferably, myeloma cell lines, or transformed B-cells or hybridomas. Preferably, the cells are non-human. Expression vectors for these cells can include expression control sequences, such as an origin of replication, a promoter, and an enhancer (Queen et al., 1986), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like (see Co et al., 1992).

Alternatively, antibody-coding sequences can be incorporated in transgenes for introduction into the genome of a transgenic animal and subsequent expression in the milk of the transgenic animal (see, e.g., U.S. Pat. Nos. 5,741,957, 5,304,489, and 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts (see generally Sambrook et al., supra). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)).

Conjugates

Also provided are conjugates (immunoconjugates) comprising an antibody of the invention conjugated to a therapeutic agent which is directly or indirectly bound to the antibody. Examples of therapeutic agents include, but are not limited to, a cytotoxin, a radioisotope (e.g., iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

A cytotoxin includes any agent that is detrimental to (e.g., kills) cells. For a description of these classes of drugs which are well known in the art, and their mechanisms of action, see Goodman et al., Goodman and Gilman's The Pharmacological Basis of Therapeutics, 8th Ed., Macmillan Publishing Co., 1990. Additional techniques relevant to the preparation of antibody immunotoxins are provided in for instance Vitetta (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

A variety of radionuclides are available for the production of radioconjugated antibodies, examples include, but are not limited to, $^{212}$Bi, $^{131}$I, $^{90}$Y, and $^{186}$Re.

Conjugates of the antibody and therapeutic agent are made using a variety of bifunctional protein-coupling agents such as, but not limited to, 4-(4'acetylphenoxy)butanoic acid (AcBut), 3-acetylphenyl acidic acid (AcPac), 4-mercapto-4-methyl-pentanoic acid (Amide), N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene), and derivatives thereof. For example, a ricin immunotoxin can be prepared as described by Vitetta et al. (1987). Carbon-14-labeled 1-isothiocyanato-benzyl-3-methyldiethylene triaminepentaacetic acid (MX-DTPA) is an exemplary chelating agent for conjugation of radionucleotide to the antibody (WO 94/11026).

In another embodiment, the antibody may be conjugated to a "receptor" (such as streptavidin) for utilization in C5a-expressing cell pretargeting wherein the antibody-receptor conjugate is administered to the patient, followed by removal of unbound conjugate from the circulation using a clearing agent and then administration of a "ligand" (e.g., avidin) that is conjugated to a therapeutic agent (e.g., a radionucleotide).

In one embodiment, an antibody of the invention is used to deliver genetic material. The genetic material can be conjugated to the antibody by any technique known in the art. Examples include, but are not limited to, the use of biotin-avidin interaction, formation of disulfide bridges, amine coupling (see, for example, Hendrickson et al., 1995), thiol coupling (see, for example, Niemeyer et al., 2003), or aldehyde-hydrazine interaction (see, for example, Kozlov et al., 2004). Other coupling agents known to those in the art, include m-maleimidobenzoyl N-hydroxysuccinimide ester or related compounds, carbodiimides, such as, 1-ethyl-3-(3-diethylaminopropyl)carbodiimide (EDC), succinimidyl 4-(N-maleimidomethyl)cyclohexane-1-carboxylate (SMCC), and glutaraldehyde cross-linkers.

Signalling Assays

The binding of a ligand, such as an agonist or C5a, to C5aR can result in signalling by this G protein-coupled receptor, and the activity of G proteins as well as stimulating other intracellular signalling molecules. The inhibitory activity of an antibody of the invention can be determined using a ligand in a suitable assay, and assessing the ability of the antibody to inhibit the activity induced by ligand.

G protein activity, such as hydrolysis of GTP to GDP, or later signalling events triggered by receptor binding, such as induction of rapid and transient increase in the concentration of intracellular (cytosolic) free calcium can be assayed by methods known in the art or other suitable methods (see, for example, Neote et al., 1993; Van Riper et al., 1993; and Dahinden et al., 1994).

The functional assay described in U.S. Pat. No. 5,284,746 of using hybrid G protein coupled receptors can be used to monitor the ability of a ligand to bind receptor and activate a G protein.

Such assays can be performed in the presence of the antibody to be assessed, and the ability of the antibody to inhibit the activity induced by the ligand is determined using known methods and/or methods described herein.

Chemotaxis and Assays of Cellular Stimulation

Chemotaxis assays can also be used to assess the ability of an antibody of the invention to block binding of a ligand to C5aR and/or inhibit function associated with binding of the ligand to the receptor. These assays are based on the functional migration of cells in vitro or in vivo induced by a compound (chemoattractant). Chemotaxis can be assessed by any suitable means, for example, in an assay utilizing a 96-well chemotaxis plate, or using other art-recognized methods for assessing chemotaxis. For example, the use of an in vitro transendothelial chemotaxis assay is described by Springer et al. (WO 94/20142) and Berman et al. (1988). Migration across endothelium into collagen gels has also been described (Kavanaugh et al., 1991). Stable transfectants of mouse L1.2 pre-B cells or of other suitable host cells capable of chemotaxis may be used in chemotaxis assays.

Generally, chemotaxis assays monitor the directional movement or migration of a suitable cell (such as a leukocyte (e.g., lymphocyte, eosinophil, basophil, neutrophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains a chemoattractant and antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy and flow cytometry). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay). The extent of migration induced by an antibody antagonist can be determined relative to a suitable control (e.g., compared to background migration determined in the absence of the antibody, compared to the extent of migration induced by a second compound (i.e., a standard), compared with migration of untransfected cells induced by the antibody). In one embodiment, particularly for T cells, monocytes or cells expressing C5aR, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

In one embodiment used to test for an antibody inhibitor of C5a signalling, a composition comprising cells capable of migration and expressing C5aR can be placed in the first chamber. A composition comprising one or more ligands or promoters capable of inducing chemotaxis of the cells in the first chamber (having chemoattractant function) is placed in the second chamber. Preferably, shortly before the cells are placed in the first chamber, or simultaneously with the cells, a composition comprising the antibody to be tested is placed, preferably, in the first chamber. Antibodies can bind receptor and inhibit the induction of chemotaxis, by a ligand or promoter, of the cells expressing C5aR in this assay are inhibitors of receptor function (e.g., inhibitors of stimulatory function). A reduction in the extent of migration induced by the ligand or promoter in the presence of the antibody is indicative of inhibitory activity. Separate binding studies could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody on the stimulatory function of C5aR can be assessed by monitoring cellular responses induced by active receptor, using suitable host cells containing receptor.

Other examples of chemotaxis assays are described herein see, for instance, Example 4.

Models of Inflammation

In vivo models of inflammation are available which can be used to assess the effects of antibodies in vivo as therapeutic agents. For example, leukocyte infiltration upon intradermal injection of a chemokine and an antibody reactive with C5aR into a suitable animal, such as rabbit, mouse, rat, guinea pig or rhesus macaque can be monitored (see, for example, Van Damme et al., 1992; Zachariae et al., 1990; Jose et al., 1994).

In one embodiment, skin biopsies are assessed histologically for infiltration of leukocytes (e.g., eosinophils, granulocytes). In another embodiment, labeled cells (e.g., stably transfected cells expressing C5aR) capable of chemotaxis and extravasation are administered to the animal. An antibody to be assessed can be administered, either before, simultaneously with or after the labeled cells are administered to the test animal. A decrease of the extent of infiltration in the presence of antibody as compared with the extent of infiltration in the absence of inhibitor is indicative of inhibition.

Uses

The antibodies of the present invention are useful in a variety of applications, including research, diagnostic and therapeutic applications.

C5aR has an important role in leukocyte trafficking. C5aR is a chemoattractant receptor for cells of the innate immune system, including neutrophils, eosinophils, mast cells, macrophages, dendritic cells, monocytes and microglia, and so anti-C5aR antibodies can be used to inhibit (reduce or prevent) leukocyte migration, particularly that associated with neutrophil tissue injury such as reperfusion injury and stroke, or with monocyte-mediated disorders such as atherosclerosis.

The antibodies described herein can act as inhibitors to inhibit (which can be reducing or preventing) (a) binding (e.g., of a ligand, an inhibitor) to the receptor, (b) a receptor signalling function, and/or (c) a stimulatory function. Antibodies which act as inhibitors of receptor function can block ligand binding directly or indirectly (e.g., by causing a conformational change). For example, antibodies can inhibit receptor function by inhibiting binding of a ligand, or by desensitization (with or without inhibition of binding of a ligand).

In one aspect, the present invention provides a method of treating or preventing a disorder in a subject. As used herein, a "disorder" is a disruption of or interference with normal function.

In an embodiment, the disorder is an immunopathological disorder.

Immunopathology is the study of disease having an immunological cause and immunologic disease is any condition caused by the reactions of antibodies to antigens. Thus, an "immunopathological disorder" can be defined as a disorder arising from reaction of antibodies to antigens—this includes autoimmune diseases and hypersensitivity responses (e.g. Type I: anaphylaxis, hives, food allergies, asthma; Type II: autoimmune haemolytic anaemia, blood transfusion reactions; Type III: serum sickness, necrotizing vasculitis, glomerulonephritis, rheumatoid arthritis, lupus; Type IV: contact dermatitis, graft rejection).

Autoimmune disease arise where the immune system fails to clear self-reacting lymphocytes during development and a subsequent breakdown in regulation leads to activation of self-reacting T or B cell clones, generating humoral or cell-mediated responses against self-antigens that causes serious damage to cells and organs.

In another embodiment, the disorder is an inflammatory disease.

Inflammation is a protective response of body tissues to irritation or injury- and can be acute or chronic. Thus, inflammatory disorders include diseases involving neutrophils, monocytes, mast cells, basophils, eosinophils, macrophages where cytokine release, histamine release, oxidative burst, phagocytosis, release of other granule enzymes and chemotaxis occur. Hypersensitivity responses (defined above under immunopathological disorders) can also be regarded as inflammatory diseases (acute or chronic) since they often involve complement activation and recruitment/infiltration of various leukocytes such as neutrophils, mast cells, basophils, etc.

Thus, disorders of humans or other species which can be treated or prevented using the invention include, but are not limited to:

i) disorders involving leukocyte migration and/or leukocyte activation such as ischaemia/reperfusion injury, reperfusion injury, stroke, adult respiratory distress syndrome (ARDS), asthma, chronic obstructive pulmonary disease (COPD), atherosclerosis, rheumatoid arthritis, psoriasis, graft rejection, cancers with leukocyte infiltration of skin or organs, Bullous pemphigoid, antiphospholipid syndrome (APS);

ii) acute inflammation such as systemic inflammatory response syndrome (SIRS), septic shock, endotoxic shock, anaphylactic shock, anaphylaxis, drug allergies, hypersensitivity responses, acute lung injury;

iii) chronic inflammation such as psoriasis, inflammatory bowel disease, Crohn's disease, ulcerative colitis, chronic obstructive pulmonary disease (COPD), asthma;

iv) autoimmune diseases, such as systemic lupus erythematosus (SLE), rheumatoid arthritis (RA), multiple sclerosis (MS) Sjogren's syndrome, ankylosing spondylitis, scleroderma, glomerulonephritis, autoimmune thyroiditis (Hashimoto's thyroiditis), Goodpasture's syndrome, psoriatic arthritis, Bullous pemphigoid, myasthenia gravis, Grave's disease, Type I/juvenile-onset/insulin-dependent diabetes, autoimmune anaemias (e.g. pernicious anaemia, autoimmune haemolytic anaemia) (which includes examples where there is overlap with i));

v) inflammatory diseases, including disorders not covered in i) or ii), as well as interstitial inflammatory diseases, spondyloarthropathies, spondylitis, vasculitis (e.g. necrotizing, cutaneous, hypersensitivity, allergic), dermatomyositis, dermatitis (e.g. allergic contact, atopic, eczema), allergic rhinitis;

vi) immunopathological disorders, including disorders not covered in i)-iii) such as graft rejection (after transplantation e.g. allograft, xenograft), graft-versus-host disease (GVHD);

vii) other types of disorders not mentioned above including age-related macular degeneration, sepsis, membranoproliferative glomerulonephritis, dense deposit disease and Alzheimer's disease.

Typically, a therapeutically effective amount of the antibody will be administered. The phrase "a therapeutically effective amount" refers to an amount sufficient to promote, induce, and/or enhance treatment or other therapeutic effect in a subject. An example of "a therapeutically effective amount" as described in the Examples section is 10 mg/kg.

In another embodiment, the various antibodies of the present invention can be used to detect C5aR or to measure the expression of receptor, for example, on neutrophils, monocytes and/or on cells transfected with a receptor gene. Thus, they also have utility in applications such as cell sorting (e.g., flow cytometry, fluorescence activated cell sorting), for diagnostic or research purposes.

The anti-C5aR antibodies of the present invention have value in detecting the presence or absence of C5aR, particularly for diagnostic applications. Typically, diagnostic assays entail detecting the formation of a complex resulting from the binding of an antibody or fragment thereof to C5aR. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). Immunohistochemistry of tissue samples may also be used in the diagnostic methods of the present invention. When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

With regard to imaging agents, any suitable agents which can be used include, but are not limited to, an MRI agent, a CT imaging agent, an optical imaging agent, an ultrasound imaging agent, a paraCEST imaging agent, and a combination thereof. In an embodiment, the agent is a proton based MRI or paraCEST agent comprising a chelate of a paramagnetic metal selected from the group consisting of scandium, titanium, vanadium, chromium, manganese, iron, cobalt, nickel, copper, molybdenum, ruthenium, cerium, indium, praseodymium, neodymium, promethium, samarium, europium, gadolinium, terbium, dysprosium, holmium, erbium, thulium, and ytterbium. In a further embodiment, the agent can be CT imaging agent comprising an iodinated oil nanoparticles or an entrapped solid metal particle. A further example of imaging agents useful for the present invention is halocarbon-based nanoparticle such as PFOB or other fluorine-based MRI agents.

Kits for use in detecting the presence of a C5aR protein in a biological sample can also be prepared. Such kits may include an antibody of the invention which binds to C5aR, as well as one or more ancillary reagents suitable for detecting the presence of a complex between the antibody or fragment and C5aR. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the antibody is employed, such antibody can be provided in the kit, for instance in a separate vial or container. The second antibody, if present, is typically labeled, and can be formulated in an analogous manner with the antibody formulations described herein.

Compositions and Modes of Administration

The formulation of an antibody of the invention to be administered will vary according to the route of administration and nature of the composition (e.g., solution, emulsion, capsule) selected. An appropriate pharmaceutical composition comprising an antibody of the invention to be administered can be prepared in a physiologically acceptable carrier. A mixture of antibodies can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (see, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate.

The antibodies of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

A variety of routes of administration are possible including, but not necessarily limited to, oral, dietary, topical, parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices.

The pharmaceutical compositions of this invention can also be administered as part of a combinatorial therapy with other agents. Such other therapies/agents are well known to those skilled in the art. In one embodiment, the disorder is rheumatoid arthritis and the other therapeutic agent is selected from the ATC code M01C class of anti-rheumatic drugs and ATC code L04 class of immunosuppresants including, but not limited to, azathioprine, chloroquine, hydroxychloroquine, cyclosporine, D-penicillamine, gold salts (sodium aurothiomalate, auranofin), leflunomide, methotrexate, minocycline, sulfasalazine and cyclophosphamide and glucocorticosteroids. In another embodiment, the disorder is systemic lupus erythematosus and the other therapeutic agent is selected from the ATC code M01C class of anti-rheumatic drugs and ATC code L04 class of immunosuppresants including, but not limited to, azathioprine, chloroquine, hydroxychloroquine, cyclosporine, D-penicillamine, gold salts (sodium aurothiomalate, auranofin), leflunomide, methotrexate, minocycline, sulfasalazine and cyclophosphamide, glucocorticosteroids, mycophenolic acid or mycophenolate and tacrolimus. In another example, the antibodies of the present invention can also be used in combination with other antibodies (e.g., in combination with antibodies which bind chemokine receptors, including, but not limited to, CCR2 and CCR3) or with anti-TNF or other anti-inflammatory agents or with existing blood plasma products, such as commercially available gamma globulin and immune globulin products used in prophylactic or therapeutic treatments. The antibodies of the present invention can be used as separately administered compositions given in conjunction with antibiotics and/or antimicrobial agents.

The dosage ranges for the administration of the antibodies of the invention are those large enough to produce the desired effect in which the symptoms of the immunopathological disease are ameliorated or the likelihood of infection or over stimulation of the immune system decreased. The dosage should not be so large as to cause adverse side effects, such as hyper-viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, preferably from about 0.2 mg/kg to about 200 mg/kg, and more preferably from about 0.5 mg/kg to about 20 mg/kg. Dose administration can be daily, weekly, or biweekly, or any other frequency as determined necessary as well as one or more daily, and dosing can go on for many months (or even years) in the case of chronic diseases.

It will be appreciated by those skilled in the art that the antibodies of the present invention may be introduced into a subject by administering a nucleic acid molecule comprising a sequence encoding the antibody. The nucleic acid molecule may be in the form of DNA or RNA or a chimeric molecule comprising both DNA and RNA. A nucleotide sequence(s) encoding the antibody may be cloned into an expression vector where the sequence encoding the agent is operably linked with expression control elements. Expression control elements are well known in the art and include, for example, promoters, enhancers and appropriate start and stop codons.

A variety of methods can be used for introducing a nucleic acid encoding the antibody into a target cell in vivo. For example, the naked nucleic acid may be injected at the target site, may be encapsulated into liposomes, or may be introduced by way of a viral vector.

Direct injection of a nucleic acid molecule alone or encapsulated, for example, in cationic liposomes may be used for stable gene transfer of a nucleic acid encoding TSP-1 into non-dividing or dividing cells in vivo (Ulmer et al., 1993). In addition, the nucleic acid can be transferred into a variety of tissues in vivo using the particle bombardment method (Williams et al., 1991).

Viral vectors are useful for gene transfer of nucleic acid molecules encoding the antibody into a specific cell type in vivo. Viruses are specialized infectious agents that can infect and propagate in specific cell types. This specificity for infecting particular cell types is especially suitable for targeting the antibody to selected cells in vivo. The selection of a viral vector will depend, in part, on the cell type to be targeted.

Specialized viral vectors are well known in the art that can target to specific cell types. Such vectors include, for example, recombinant adeno-associated viral vectors having general or tissue-specific promoters (U.S. Pat. No. 5,354,678). Recombinant adeno-associated viral vectors have the added advantage that the recombinant virus can stably integrate into the chromatin of even quiescent non-proliferating cells (Lebkowski et al., 1988).

Viral vectors can be constructed to further control the type of cell that expresses the encoded antibody by incorporating a tissue-specific promoter or enhancer into the vector (Dai et al., 1992).

Retroviral vectors are also suitable for the methods for delivering nucleic acid molecules encoding the antibody in vivo. Such vectors can be constructed either to function as infectious particles or as non-infectious particles that undergo only a single initial round of infection.

Receptor-mediated DNA delivery approaches also can be used to deliver a nucleic acid molecule encoding the antibody into a cell in a tissue-specific manner using a tissue-specific ligand or an antibody that is non-covalently complexed with the nucleic acid molecule via a bridging molecule (Curiel et al., 1992; Wu and Wu, 1987).

Gene transfer to obtain expression of the antibody in a subject also can be performed by, for example, ex vivo transfection of autologous cells. Suitable cells for such ex vivo transfection include blood cells since these cells are readily accessible for manipulation and reintroduction back into the subject by methods well known in the art.

Gene transfer through transfection of cells ex vivo can be performed by a variety of methods, including, for example, calcium phosphate precipitation, diethyaminoethyl dextran, electroporation, lipofection, or viral infection. Such methods are well known in the art (see, for example, Sambrook et al., Molecular Cloning: A Laboratory Manual, Cold Springs Harbour Laboratory Press (1989)). Once the cells are transfected, they are then transplanted or grafted back into a subject to be treated. The cells once introduced into the body can produce the antibody, which can enter the circulation and inhibit platelet aggregation at the site of the disease or condition.

EXAMPLES

Example 1

Humanization Process

Defining CDR and Framework Residues

The CDR and framework regions of an antibody have usually been defined according to various numbering schemes such as Kabat, Chothia or IMGT (ImMunoGeneTics information system® http://imgt.cines.fr). The Kabat definition is based on sequence variability and is the most commonly used. However, the CDRs for a given antibody as defined by Kabat are not necessarily identical to the CDRs defined by the other numbering systems. The CDRs defined by two numbering systems may overlap, or one may extend a few residues either side of the other.

The inventors used a combination of the Kabat and IMGT numbering systems to define the CDRs and framework regions in the variable (V) domain. The inventors wanted to maximise the extent of the mouse CDR sequences that were grafted into the human framework in order to preserve the structure of the antigen-binding pocket. So, the C5aR antibody CDRs included all residues classified as CDR by both the Kabat and IMGT numbering systems. The remaining sequences comprised the V domain framework.

ii) Known human antibodies with high homology to a mouse C5aR antibody heavy or light chain were identified and the V region framework (or a modified version) used to graft the mouse C5aR antibody CDRs.

iii) Other successfully humanized antibodies utilising framework sequences similar to the mouse C5aR antibodies were identified and the mouse CDRs were grafted onto these frameworks.

Selecting Homologous Antibodies from Sequence Databases

The mouse C5aR antibody, 7F3 variable region amino acid sequences (both heavy and light chains, see SEQ ID NO's 1 and 2) were individually used as the query sequence in Blastp searches of the human immunoglobulin sequences in SWIS-SPROT and Genbank databases.

The mouse 7F3 variable region DNA sequences (encoding both heavy and light chains, see SEQ ID NO's 3 and 4) were individually used as the query sequence in Blast searches of the IMGT database of human immunoglobulin genes.

A list of sequences with the highest homology to the query sequence was generated from each search (Tables 2 and 3).

TABLE 2

Human Sequences Homologous to Mouse C5aR mAb Variable Light Chain

| Query | Database | Sequence ID | Description | Score |
|---|---|---|---|---|
| mouse 7F3 Vk amino acid | SWSS_PROT | KV2F HUMAN | Ig kappa chain V-II: RPMI6410 | 181.0 |
| | | KV2D HUMAN | Ig kappa chain V-II: TEW | 181.0 |
| | | KV2E HUMAN | Ig kappa chain V-II: GM607 | 176.0 |
| | | KV2B HUMAN | Ig kappa chain V-II: FR | 173.0 |
| | | KV2A HUMAN | Ig kappa chain V-II: CUM | 169.0 |
| | | KV2C HUMAN | Ig kappa chain V-II: MIL | 166.0 |
| | | KV4C HUMAN | Ig kappa chain V-IV: B17 | 150.0 |
| | | KV4A HUMAN | Ig kappa chain V-IV: LEN | 150.0 |
| | | KV4B HUMAN | Ig kappa chain V-IV: JI | 148.0 |
| | | KV3D HUMAN | Ig kappa chain V-III: TI | 138.0 |
| mouse 7F3 Vk DNA | IMGT human Ig V genes | U416644 | IGKV2D-29*02 | 993 |
| | | M31952 | IGKV2D-29*01 | 984 |
| | | X63396 | IGKV2-29*01 | 984 |
| | | U41645 | IGKV2-29*02 | 975 |
| | | X12691 | IGKV2D-28*02 | 975 |

Selecting Suitable Human Antibody Framework Sequences

To select suitable human antibody framework sequences onto which the mouse CDRs were grafted the inventors used a number of strategies:

i) Blast searches of sequence databases identified human Ig V region light and heavy chain sequences with the highest homology to mouse C5aR antibodies. The most highly homologous sequences were aligned and consensus framework sequences were generated for the light and heavy chains.

Consensus Framework Sequence—Light Chain 7F3

A light chain human framework consensus sequence for grafting the 7F3 light chain CDRs was generated using ClustalW by aligning the following sequences from Table 2: KV2F_HUMAN, KV2D_HUMAN, KV2E_HUMAN, KV2B_HUMAN, KV2A_HUMAN and the amino acid translation of DNA sequences X12691, U41645, U41644, M31952. This alignment and consensus sequence are shown in FIG. 1. The human consensus framework was 86% identical to the murine C5aR antibody 7F3 light chain framework sequence.

TABLE 3

Human Sequences Homologous to Mouse C5aR mAb Variable Heavy Chain

| Query | Database | Sequence ID | Description | Score |
|---|---|---|---|---|
| mouse 7F3 Vh amino acid (V gene region) | SWSS_PROT | HV1C HUMAN | Ig heavy chain V-I: ND | 142.0 |
| | | HV1B HUMAN | Ig heavy chain V-I: HG3 | 138.0 |
| | | HV1G HUMAN | Ig heavy chain V-I: V35 | 134.0 |
| | | HV3J HUMAN | Ig heavy chain V-III: HIL | 130.0 |
| | | HV1A HUMAN | Ig heavy chain V-I: EU | 127.0 |
| | | HV3G HUMAN | Ig heavy chain V-III: CAM | 123.0 |
| | | HV3K HUMAN | Ig heavy chain V-III: KOL | 122.0 |
| | | HV3H HUMAN | Ig heavy chain V-III: GA | 122.0 |
| | | HV1H HUMAN | Ig heavy chain V-I: DOT | 120.0 |
| | | HV1F HUMAN | Ig heavy chain V-I: MOT | 120.0 |

TABLE 3-continued

Human Sequences Homologous to Mouse C5aR mAb Variable Heavy Chain

| Query | Database | Sequence ID | Description | Score |
|---|---|---|---|---|
| mouse 7F3 Vh amino acid (J gene region) | SWISS-PROT | HV3K HUMAN | Ig heavy chain V-III: KOL | 29.0 |
| | | HV2I HUMAN | Ig heavy chain V-II: ARH-77 | 28.2 |
| | | HV1C HUMAN | Ig heavy chain V-I: ND | 28.2 |
| | | HV3T HUMAN | Ig heavy chain V-III: GAL | 27.8 |
| | | HV3H HUMAN | Ig heavy chain V-III: GA | 27.8 |
| mouse 7F3 Vh DNA (V gene region) | IMGT human Ig V genes | Z12305 | IGHV1-f*01 | 777 |
| | | M99642 | IGHV1-24*01 | 768 |
| | | L06612 | IGHV1-46*03 | 750 |
| | | J00240 | IGHV1-46*02 | 750 |
| | | X92343 | IGHV1-46*01 | 750 |

Consensus Framework Sequence—Heavy Chain 7F3

A consensus human framework sequence for grafting the 7F3 heavy chain CDRs was generated as follows:

a) V region amino acid sequences HV1C_HUMAN, HV1B_HUMAN, HV1G_HUMAN & HV1A_HUMAN and the amino acid translations of V gene sequences X92343, X62109, M99641, M99642 and Z12305 were aligned using CLUSTALW to generate consensus V region framework sequence.

b) J region amino acid sequences HV3K_HUMAN, HV2I_HUMAN, HV1C_HUMAN, HV3H_HUMAN and HV3T_HUMAN were aligned using CLUSTALW to generate consensus J region framework sequence.

These alignments and consensus sequences are shown in FIG. 2.

Selecting Homologous Humanized Antibodies

Other suitable framework sequences were selected by searching the literature for successfully humanized antibodies with the closest match to the murine antibody sequences.

Two light chain framework sequences were identified for grafting the 7F3 light chain CDRs:

KV2F-based sequence described in Caldas et al. (2003).
HuVL-19-based sequence described in Nisihara et al. (2001).

Heavy chain framework sequences identified for grafting the 7F3 heavy chain CDRs were:

HG3-based sequence described in Caldas et al. (2000).
SGI-VH-based sequence described in Nisihara et al. (2001).

Grafting CDRs into Framework Sequences and Creation of Humanized Light and Heavy Chain Sequences Humanized 7F3 Light Chain Three versions of a humanized 7F3 light chain variable region were created.

The first was designed by taking the consensus human framework sequence from FIG. 1, comparing this sequence with the mouse 7F3 framework sequence, changing selected amino acids in the human framework back to the mouse residue and then grafting on the mouse 7F3 light chain CDRs (FIG. 3). The residues in the human framework selected to change back to the mouse sequence were: #2 from Ile to Val, #15 from Pro to Leu and #92 from Tyr to Phe. The first two changes were made because the residue found in mouse matched the amino acid in the human sequence most homologous to mouse 7F3 i.e. KV2F_HUMAN. The third change was made because of its proximity to CDR3 and the need to minimize changes to the structure of the antibody-binding region. The mouse 7F3 light chain CDRs were grafted into the modified consensus framework sequence to create sequence h7Vk (FIG. 3) (SEQ ID NO:31).

The second humanized 7F3 light chain variable region was created by grafting the mouse 7F3 light chain CDRs onto the humanized HuVL-19 framework sequence, RNOK203VL, described above (FIG. 4). This gave sequence h7aVk (FIG. 4) (SEQ ID NO:32).

The third humanized 7F3 light chain variable region was created by grafting the mouse 7F3 light chain CDRs onto the KV2F-derived framework sequence VLCD18-Q described above (FIG. 5). Compared with the KV2F_HUMAN framework sequence (see FIG. 1 and SEQ ID NO:5), 2 amino acids were changed back to the mouse 7F3 sequence: #51 from Arg to Leu to remove a $2^{nd}$ charged residue where there was only one in the mouse and #109 from Val to Leu. One further difference was a change at residue #105 from Gln to Gly to remove a bulky side chain. This gave sequence h7bVk (FIG. 5) (SEQ ID NO:33).

A comparison of the 3 humanized 7F3 Vk sequences created is shown in FIG. 6. These sequences vary from a consensus sequence h7F3VkCons at 2-5 positions in the framework regions, meaning all are over 93% identical to each other. Data presented below shows that humanized 7F3 antibodies containing certain light chains are preferred over others. In particular, residues between CDR loops L1 and L2 are critical and certain changes in this region can have detrimental effects (e.g. introduction of a Cys residue at residue #41). Other changes such as the introduction of additional charged residues had very little relative effect. It is possible that other changes could be made to the humanized 7F3 Vk sequences that would not be detrimental to the properties of an antibody containing these changes.

Humanized 7F3 Heavy Chain

Three versions of a humanized 7F3 heavy chain variable region were created.

The first was designed by taking the consensus human framework sequence from FIG. 2, comparing this sequence with the mouse 7F3 framework sequence, changing selected amino acids in the human framework and then grafting on the mouse 7F3 heavy chain CDRs (FIG. 7). The residues in the human consensus framework that were altered were: #20 to Ile, #43 to Lys (to keep a charged residue), #72 to Ala (to remove a charged residue), #91 to Ser, and #95 to Phe. These residues are the same as the mouse framework but are also found in at least one human Ig sequence. In addition, a relatively ambiguous region in F3 was resolved by selecting the HV1Av sequence at this point, thus incorporating Ile at residue #70 and Glu at #74. Grafting the mouse 7F3 heavy chain CDRs into the modified consensus framework sequence created sequence h7Vh (FIG. 7) (SEQ ID NO:34).

The second humanized 7F3 heavy chain variable region was created by grafting the mouse 7F3 heavy chain CDRs onto the SGI-VH-derived framework sequence described above (FIG. 8). At six positions in the SGI-VH framework the human residue was changed to the mouse 7F3 residue. These changes were made at residues #38 (Arg to Lys), #48 (Val to Ile), #67 (Arg to Lys), #68 (Val to Ala), #72 (Leu to Ala) and #77 (Asn to Ser). These changes were made since the residues are in close proximity to CDRs H1 or H2 and were thought to be important in formation of the binding pocket. For instance, back-mutations at these positions in SGI-VH to create sequence RNOK203VH had been shown to improve neutralizing activity of a humanized anti-FasL antibody (Nisihara et al, 2001). This gave sequence h7aVh (FIG. 8) (SEQ ID NO:35).

The third humanized 7F3 heavy chain variable region was created by grafting the mouse 7F3 light chain CDRs onto the HG3-derived framework sequence described above (FIG. 9). One position in the HG3 framework, residue #71(Arg), was back-mutated to the mouse 7F3 residue (Ala) to remove a positively charged residue. This gave sequence h7bVh (FIG. 9) (SEQ ID NO:36).

A comparison of the 3 humanized 7F3 Vh sequences created is shown in FIG. 10. These sequences vary from a consensus sequence h7F3VhCons at 1-8 positions in the framework regions, meaning all are over 90% identical to each other. Some significant differences between the sequences include Lys vs Gln at residue #43 and Glu vs Thr at #74. However, data presented below shows that humanized 7F3 antibodies containing any of the 3 heavy chains are effective at blocking C5a binding to human C5aR. It seems therefore that the differences between the Vh sequences are not critical and that it is possible that other changes could be made to the humanized 7F3 Vh sequences that would not be detrimental to the properties of an antibody containing such a modified sequence. Nevertheless, it is likely that certain substitutions made to a humanized 7F3 Vh sequence could improve the properties of the antibody, and that other substitutions would likely be detrimental.

Molecular Modelling
Background

Modelling of antibody binding sites is a combination of protein homology modelling, in which a large number of antibody structures can serve as a knowledge database, and ab initio modelling that must be used for those parts of the antibody that are too variable to apply homology methods. The majority of the variable fragment (Fv) framework region (FW) is well conserved in structure between different antibodies. After taking into account those variations that do occur in particular β-strands, the framework can be modelled by selection of a known structure that is closest in sequence to the Fv to be modelled.

Most sequence and structural variability in antibodies is restricted to the hypervariable regions (CDRs) that bind antigen. These six loops (L1, L2, L3, H1, H2 and H3) are located on the antibody surface and it is the modeling of these CDRs that poses the greatest challenge. All CDRs except H3 usually fall into one of between 2 and 6 structural (canonical) classes (Chothia and Lesk, 1987; Chothia et al., 1989). Members of a canonical class all have approximately the same backbone conformation. So, to model an unknown CDR, the sequence is examined, the appropriate canonical class assigned, and the most sequence-homologous known CDR used. The H3 loop is more difficult to model as its conformation varies considerably between structures.

Current methods of antibody modelling have usually taken the homology approach (see, for example, Pulito et al., 1996; Eigenbrot et al., 1993; Barry et al., 1994). The algorithm used by WAM (Web Antibody Modelling, see http://antibody.bath.ac.uk) uses the most sequence-homologous frameworks and canonical CDR loops to the sequence being modeled, chosen from a database of known antibody structures.

For non-canonical loops, a different method is used. This is the CAMAL (Combined Antibody Modelling Algorithm) of Martin et al. (1989), and consists of a combined database/conformational search.

Model Generation

WAM was used to generate models of the mouse 7F3 Fv regions (with both heavy and light chains) as well as models of the humanized 7F3 Fv regions.

A number of models of the humanized Fv regions were generated (each containing one V region light chain and one V region heavy chain) since the inventors had produced several sequence variants for each of humanized 7F3 heavy and light chain. Each humanized Fv model was compared to the mouse 7F3 Fv structure, with the structures of the CDRs being compared in detail using DeepView/SWISS-PdbViewer. Differences between the two structures were highlighted. For instance, when the h7Vk-h7Vh structure was compared to 7F3 Fv structure, the h7Vk light chain fit to 7F3 Vk was very good, being almost identical, but the heavy chain CDRs H2 and H3 were not as closely aligned. By contrast, in another model, comprising the h7aVk-h7aVh sequences, the heavy chain alignment with 7F3 Vh was better than with h7Vh, but the light chain alignment was considerably different in the CDRs. From this analysis it was speculated that the combination of h7Vk and h7aVh might produce an antibody most similar to 7F3. Analysis of the antibody comprising the h7bVk-h7bVh sequences revealed CDRs L1, H1, H2 and H3 were more structurally different from equivalent 7F3 CDRs than the other h7F3 heavy and light chains, suggesting that antibodies containing the h7bVk or h7bVh sequences may not be as effective as 7F3 or humanized 7F3 antibodies not containing these sequences. Given this, it was surprising and unexpected that one antibody containing the h7bVh sequence was shown to have superior activity to 7F3 (see Example 5, FIG. 17).

The next step was to convert the humanized 7F3 heavy and light chain sequences described above into antibodies for testing in vitro and in vivo.

Example 2

Expression and Production of Humanized Antibodies

Cloning Antibody Variable Region Genes into Vectors with Constant Region Gene

The heavy and light chain variable amino acid sequences were designed as described above. To produce antibodies containing these domains a DNA sequence encoding each variable region was synthesized (Genescript Corp.). EcoR1 and HindIII sites were added at the 5' or 3' end to facilitate cloning into the vector pUC18. In addition, the light chain variable gene had unique BsmB1 restriction sites at each end. The heavy chain gene had a BsmB1 site at the 5' end and an Nhe1 site at the 3' end.

To construct a full-length antibody gene a variable region gene was subcloned into a vector encoding a secretion signal and the constant domain. For the light chain, this vector contained the secretion signal sequence and the human constant kappa (Cκ) region gene separated by two unique BsmB1 sites. The heavy chain vectors contained the secretion signal and a human constant gamma (Cγ) region gene separated by BsmB1 and Nhe1 sites. Heavy chain vectors contained either the gamma 1 ($C\gamma_1$), gamma 2 ($C\gamma_2$), gamma 3 ($C\gamma_3$), gamma 4 ($C\gamma_4$), gamma $4_{PE}$ mutant ($C\gamma 4_{PE}$) or gamma $4_P$ mutant ($C\gamma 4_P$) gene.

The cloning process involved preparation of plasmid DNA by standard methods, digestion of the plasmid DNA with BsmB1 (light chain vector and Vk region gene) or BsmB1 and Nhe1 (heavy chain vector and Vh region gene) as recommended by the manufacturer (New England Biolabs and Promega), separation of DNA fragments by agarose gel electrophoresis, recovery of DNA fragments from the gel using a gel extraction kit (JetQuick, Genomed), ligation of variable gene fragment to vector fragment (T4 DNA ligase, Promega), transformation of DNA into competent E. coli cells (TOP10, Invitrogen). Plasmid DNA from transformed cells was analysed by restriction digest and the antibody gene in the plasmid was sequenced to confirm that the variable region had been subcloned in the correct reading frame.

Subcloning Antibody Genes into Expression Vector

After confirmation that the full-length antibody gene had the correct sequence it was subcloned into an expression vector. Examples of expression vectors that could be used include any of the pcDNA-, pLENTI-, pT-REX-, pAd-, pREP- or pCEP-mammalian expression vectors (Invitrogen), pTriEx1 or pBac vectors (Novagen), ZAP and pCMV expression vectors (Stratagene), GS expression system vectors e.g. pEE12.4 and pEE6.4 (Lonza), pCMV5 cumate expression system vectors (Qbiogene), UCOE expression system plasmids (ML Laboratories) or MARtech expression plasmids (Selexis). In this instance the heavy chain genes (with HindIII site at 5' end and EcoR1 site at 3' end) were subcloned into the HindIII-EcoR1 sites downstream of the CMV promoter in a pcDNA3-derived vector (Invitrogen) containing the mouse DHFR gene and/or into a GS expression vector (Lonza). The light chain genes (with Spelsite at 5' end and EcoR1 site a 3' end) were subcloned into the Nhe1-EcoR1 sites of pTracer-CMV/BSD (Invitrogen). The light chain genes with HindIII site at 5' end and EcoRI site at 3' end were also subcloned into the HindIII-EcoRI sites of a GS expression vector (Lonza). In some cases the heavy chain expression cassette (promoter, light chain coding sequence and polyadenylation signal) was subcloned into the light chain vector to create a single vector that expressed both heavy and light chains.

Expressing Humanized Antibody in Mammalian Cells

To express a humanized antibody a heavy and light chain vector were cotransfected into CHO cells using lipofectamine (Invitrogen). Alternatively, the vector DNA could be transfected by electroporation, calcium phosphate precipitation, direct injection, gene gun or another method known to those skilled in the art. Alternatively, the vector DNA could be transfected into any number of mammalian cell lines e.g. CHOK1SV, HEK293, PerC6 or NS0. On some occasions a single vector encoding both heavy and light chains was transfected into cells by electroporation or using lipofectamine.

One day before transfection $4\times10^5$ CHO dhfr$^-$ cells (ATCC) were seeded into a T175 flask in 15 ml non-selective medium (alpha-MEM with nucleosides (Invitrogen), 2 mM L-glutamine, 10% FBS) and incubated at 37° C. in 5% $CO_2$. Immediately prior to transfection plasmid DNA (15 µg) in 800 µl growth medium was added to 100 µl lipofectamine (Invitrogen) in 800 µl growth medium and incubated at room temperature for 20 min. The cell monolayer was rinsed with PBS and the DNA/lipofectamine mix was added to the flask with 5 ml growth medium. After 16 hours incubation at 37° C. in 5% $CO_2$ another 10 ml medium was added. One day later the cells were washed with PBS and 15 ml selective medium (alpha-MEM minus nucleosides and 5% dialysed FBS) was added. After 2 days adherent cells were replated in 96 well tissue culture plates at an average density of ~2-5 cells per well. After a further 2-3 weeks growth antibody production was measured using a human IgG-specific ELISA. Cells expressing antibody were expanded into T-flasks for production. Culture medium was harvested and antibody purified as described below. GS system expression vectors were transfected into CHOK1SV cells and antibody secreting cell lines isolated and expanded for production as recommended by the manufacturer (Lonza).

Purification of Humanized Antibody

The transfected cells secrete antibody into the growth medium. Antibody was purified by protein A or protein G affinity chromatography. Fractions containing antibody, identified by SDS-PAGE or by human IgG-specific ELISA, were pooled. A human IgG-specific ELISA was used to determine the amount of antibody recovered and its concentration. Antibody purity was estimated by polyacrylamide gel electrophoresis.

List of Humanized Antibodies Produced and Assayed.

The Table 4 lists the different antibodies produced, showing the heavy and light chain sequences present in the antibody.

TABLE 4

Humanized Antibodies Produced

| Antibody hAb | Light Chain Variable (V) | Light Chain Constant | Heavy Chain Variable (V) | Heavy Chain Constant |
|---|---|---|---|---|
| A | 7Vk | hCκ-R | 7Vh | hCγ4 |
| B | 7aVk | hCκ-R | 7Vh | hCγ4 |
| C | 7bVk | hCκ-R | 7Vh | hCγ4 |
| D | 7Vk | hCκ-R | 7Vh | hCγ4$_{PE}$ |
| E | 7aVk | hCκ-R | 7Vh | hCγ4$_{PE}$ |
| F | 7bVk | hCκ-R | 7Vh | hCγ4$_{PE}$ |
| G | 7Vk | hCκ-R | 7aVh | hCγ4$_{PE}$ |
| H | 7aVk | hCκ-R | 7aVh | hCγ4$_{PE}$ |
| I | 7bVk | hCκ-R | 7aVh | hCγ4$_{PE}$ |
| J | 7Vk | hCκ-R | 7bVh | hCγ4$_{PE}$ |
| K | 7aVk | hCκ-R | 7bVh | hCγ4$_{PE}$ |
| L | 7bVk | hCκ-R | 7bVh | hCγ4$_{PE}$ |
| M | 7Vk | hCκ-R | 7aVh | hCγ4 |
| N | 7Vk | hCκ-R | 7aVh | hCγ1 |
| O | 7bVk | hCκ-R | 7Vh | hCγ1 |
| P | 7Vk | hCκ | 7bVh | hCγ1 |
| Q | 7Vk | hCκ | 7bVh | hCγ4$_P$ |
| R | 7Vk | hCκ | 7aVh | hCγ4$_P$ |
| S | 7Vk | hCκ | 7bVh | hCγ4$_{PE}$ |
| T | 7Vk | hCκ | 7aVh | hCγ4$_{PE}$ |
| U | 7Vk | hCκ | 7aVh | hCγ1 |
| V | 7Vk | hCκ | 7aVh | hCγ4$_P$ |

Example 3

Binding Studies with Humanized Anti-C5aR Antibodies

To characterise the binding kinetics of the humanized anti-C5aR antibodies to the human C5a receptor (hC5aR), two types of binding studies are described in this example. The first compared the binding of antibodies and C5a to human C5aR in competitive-ligand binding assays. The second involved saturation binding in cells expressing human C5aR.

A. Humanized Anti-C5aR Displace C5a Binding to C5aR—Competition Ligand Binding Assay The ability of humanized Abs to inhibit $^{125}$I-labelled C5a binding to L1.2 cells transfected with hC5aR gene or human neutrophils was tested as described below. Recombinant human C5a was obtained from Sigma Chemical Co. (St. Louis, Mo.). $^{125}$I-Bolton-Hunter-labelled complement C5a was purchased from NEN-Dupont (Boston, Mass.), with a specific activity of 2200 Ci/mM. Briefly, L1.2/hC5aR stable transfectants were grown for several days prior to an experiment then treated overnight with 5 mM butyric acid to stimulate hC5aR expression prior to the binding assay. Human neutrophils were purified from venous blood collected from healthy volunteers. Neutrophils were separated from other leukocytes by percoll density centrifugation followed by a red blood cell lysis step. Both cell types were washed once in PBS and resuspended in binding buffer (50 mM Hepes, pH 7.5, 1 mM $CaCl_2$, 5 mM $MgCl_2$, 0.5% BSA) at a concentration of $1 \times 10^7$/ml. Aliquots of 40 µl ($4 \times 10^5$ cells) were dispensed into 96 well microtitre plates, followed by the addition of cold competitor (antibody or human C5a). Cells and cold competitor were incubated for 15 min at room temperature before-radiolabelled C5a was added to a final concentration of 0.4 nM. The final reaction volume was 120 µl. After 60 min incubation at room temperature, the cells were washed three times with 150 µl of binding buffer containing 0.15 M NaCl. Cell pellets were then counted on a TopCount Scintillation Counter (Packard). Samples were assayed in triplicate at each of 6-8 concentrations. Each antibody was tested in at least 3 separate assays. The number of counts in each sample was expressed as a percentage of the maximum $^{125}$I-C5a binding observed in wells with no added cold competitor after subtraction of background.

Results of this analysis (the displacement curves) for each of the humanized antibodies compared to the mouse antibody 7F3 in human neutrophils and L1.2/hC5aR transfectants are given in FIGS. 11 and 12 respectively. Table 5 shows the $EC_{50}$ values for each antibody. These values were obtained using Graphpad Prism software fitting the data to the non-linear equation for one site competition. Data shows that not all humanized antibodies were equally effective in displacing radiolabelled C5a from the receptor. Humanized antibodies O and N were as effective as mouse 7F3 in human neutrophils, while antibodies C, J, M, N, O and Q were not significantly different from 7F3 in the L1.2/hC5aR transfectants.

TABLE 5

$EC_{50}$ Values for each Antibody shown in FIGS. 11 and 12.

| Antibody or Ligand | EC50 (human neutrophils) nM | 95% CI | EC50 (L1.2/hC5aR transfectants) nM | 95% CI |
|---|---|---|---|---|
| human C5a | 0.5 | 0.37-0.88 | | |
| m7F3 | 0.54 | 0.39-0.75 | 0.51 | 0.35-0.75 |
| A | nd | | 2.78 | 1.81-4.27 |
| C | 2.48 | 1.49-4.12 | 0.90 | 0.56-1.47 |
| F | 2.55 | 1.51-4.31 | 1.26 | 0.88-1.80 |
| G | 3.52 | 1.95-6.35 | 1.53 | 0.92-2.52 |
| J | 4.11 | 2.14-7.91 | 0.93 | 0.63-1.31 |
| M | 4.05 | 2.53-6.49 | 0.95 | 0.60-1.48 |
| N | 0.65 | 0.45-0.94 | 1.03 | 0.56-1.90 |
| O | 0.48 | 0.32-0.70 | 0.68 | 0.39-1.17 |
| Q | 3.50 | 2.42-5.05 | 0.86 | 0.52-1.46 |
| S | 2.69 | 1.46-4.96 | nd | |

B. Saturation Binding of Anti-C5aR Antibodies to Purified Human Neutrophils

Human neutrophils, isolated as described above, were resuspended in dPBS and $1 \times 10^5$ cells (in 25 µl) were dispensed into wells of a 96-well plate. An equal volume (25 µl) of 2x antibody (diluted in PBS) was added to each well. The final antibody concentration using 2-fold serial dilution ranged from 40 to 0 ug/ml (using unlabelled hAb-Q, hAb-J and 7F3). Cells and antibody were incubated for 20 min times at 4° C. After incubation, 100 µl PBS+1% BCS was added to each well and the plate centrifuged at 2,000 rpm for 3 min. Cells were washed 3 times in PBS+1% BCS and resuspended in anti-human IgG-FITC (Sigma F1641) or anti-mouse IgG-FITC (Jackson 195-115-003) diluted 1/300 in PBS and incubated for 20 min on ice. The cells were washed once as above and resuspended in PBS+1% FCS for analysis by flow cytometry. FSC v SSC scatter was used to identify neutrophils, with the Median Fluorescence Intensity (MFI) determined for each sample. EC50 values were determined by fitting data (MFI—background vs $\log_{10}$[antibody concentration]) to the sigmoidal dose-response (variable slope) i.e. 4-parameter logistic equation using GraphPad Prism (v4.0) software. $B_{max}$ and $K_D$ were determined by fitting data to the one-site binding hyperbola equation.

FIG. 13 shows two saturation binding graphs, with the x-axis in $\log_{10}$ (to calculate $EC_{50}$) and linear (to calculate $B_{max}$ and $K_D$) scales. The data shows that the $K_D$ and $EC_{50}$ values of the humanized anti-C5aR antibodies N and Q binding to human neutrophils at 4° C. were about 2-3 fold higher than 7F3. The $K_D$ and $EC_{50}$ for the humanised antibodies are similar, each around 20-25 nM (~3 ug/ml), while the $K_D$ and $EC_{50}$ for 7F3 were in the range ~8-10 nM under the conditions of this assay.

Example 4

Humanized Anti-C5aR Antibodies Bind to the Epitope EEYFPP (SEQ ID NO:38) in the Second Extracellular Loop of Human C5aR Methods Antibody Binding to Chimeric Receptors A series of chimeric receptors comprising segments of mouse and human C5aR were constructed to identify the region of the C5a receptor that the antibodies bound. These receptors were generated using standard molecular techniques (Lee et al., 2006). Each recombinant vector (5 µg diluted in DMEM) encoding a different chimeric receptor was transfected into $5 \times 10^5$ mouse L1.2 cells using Lipofectamine 2000 (Invitrogen). Cells were grown in DMEM or RPMI (Invitrogen) plus 10% foetal bovine serum (Hyclone). After 24 hours or 48 hours, cells were harvested by centrifugation at 1,500 rpm for 5 min and resuspended in FACS buffer (phosphate buffered saline plus 2% bovine serum albumin). For staining with hAb-Q, $0.5 \times 10^5$ transfected cells were incubated with 5 or 10 µg/ml antibody in a volume of 50 µl per well at 4° C. for 20 minutes. Cells were pelleted as above and rinsed 3 times with 150 µl FACS buffer before addition of 50 µl FITC-conjugated anti-human IgG diluted 1:200 or 1:300 (Sigma, F1641). This mix was incubated for 20 min at 4° C. before cells were pelleted, washed with FACS buffer 3 times and finally resuspended in 150-200 µl FACS buffer. Samples were analysed on a FACS Calibur (BD Biosciences).

Antibody Binding to Peptides from the Second Extracellular Loop

A set of 22 overlapping peptides (12 mers), each offset by 1 residue from the next, spanning the second extracellular loop ($3^{rd}$ extracellular domain) of human C5aR was synthesised (Mimotopes, Melbourne). Each peptide was made with a biotin group and 4-amino acid linker (SGSG) at its N-terminus. One peptide synthesised, no. 23, was a 33 mer, representing the full length of the 2nd extracellular loop of hC5aR (residues 173-205 from SEQ ID NO:37), also had biotin-SGSG at the N-terminus. The peptides used in this experiment are described in Lee e al. (2006).

The experiment was conducted by binding the peptides to a 384-well streptavidin-coated plate then incubating the antibodies with the peptides and detecting bound antibody with an anti-mouse IgG conjugated to horse radish peroxidase (HRP) as follows. Each peptide was dissolved in 200 μl of 60% DMSO to a concentration of 10 mg/ml. Peptides were further diluted 1:1000 to a working strength of 10 μg/ml with PBS/Tween 20/azide solution (0.1% w/v sodium azide in PBS/0.05% Tween 20).

A 384 well streptavidin-coated plate (Nunc) was blocked with 20 μl of blocking buffer (1% w/v BSA in PBS) per well. The plate was washed 4 times with PBS/Tween20 buffer (0.1% v/v Tween 20 in PBS). 20 μl of diluted peptide solution was transferred into a well and the plate incubated for 1 hour at room temperature. After washing the plate 4 times (as above) 20 μl antibody (0.5, 1, 1.25, 2.5 or 5 μg/ml) was added to the well and the plate was incubated for 1 hour at 20° C. The plate was washed 4 times as above then 20 μlHRP-conjugated anti-mouse IgG (1:5000 dilution in PBS/Tween 20) was added to each well. After a 1 hour incubation at room temperature the plate was washed 3 times (as above) then twice with PBS to remove traces of Tween. The presence of peroxidase was detected by adding 20 μl of freshly prepared TMB Substrate reagent (BD Opt EIA) to each well and incubating at room temperature for 20 min. Finally the plate was read at 650 nm/450 nm.

Identification of Critical Amino Acids within the 2nd Extra-Cellular Loop: Alanine Scanning Mutant Peptides.

To further define the critical binding residues in the epitope EEYFPP (residues 179-184 from SEQ ID NO:37) (SEQ ID NO:38), a series of short peptides (12 mers) comprising the human C5aR $2^{nd}$ extracellular loop sequence VREEYFPP-KVLC (residues 177-188 from SEQ ID NO:37) (SEQ ID NO:58) with alanine substituted at different positions in the binding motif were synthesised as above with a biotin group and 4 amino acid linker (SGSG) at their N-terminus (Lee et al., 2006). Peptide A1 had no Ala substitution and peptide A14 was a scrambled version of peptide A1. Peptides A2-A13 contained a single alanine substitution at each amino acid position from 12 to 1 respectively. Binding of antibodies to the peptides coated on ELISA plates was carried out as described above.

N-Terminal Peptide (PEP1) ELISA

A 384-well MaxiSorp plate (Nunc) was coated with a peptide corresponding to residues 9-29 of human C5aR (PEP1), at concentrations of 1-15 μg/ml in PBS/0.01% Tween-20 at 37° C. for 1.5 hours, then washed 3 times. The plate was blocked with 20 μl of blocking buffer (1% w/v BSA in PBS) per well for overnight at 4° C. The plate was washed 3 times with PBS/Tween buffer (0.05% v/v Tween-20 in PBS). 20 μl antibody (final concentration 5 μg/ml) was added to each well and the plate was incubated for 2 hours at 37° C. The plate was washed 3 times as above then 20 μl HRP-conjugated anti-human IgG kappa (1:8000 dilution in PBS/Tween 20) or HRP-conjugated anti-mouse IgG (1:7500 dilution) was added to each well. After a 2 hour incubation at room temperature the plate was washed 4 times (as above). The presence of peroxidase was detected by adding 20 μl of freshly prepared TMB Substrate reagent (BD Opt EIA) to each well and incubating at room temperature for 20 min. Finally after stopping the reaction with 20 μl 1M $H_2SO_4$ per well the plate was read at 450 nm (reference 620 nm) in a plate reader.

Results

To confirm that the humanised anti-C5aR antibodies recognized the same binding site in human C5aR as the parental antibody 7F3 four experiments were performed. Firstly, hAb-Q was used to stain cells expressing various chimeric human/mouse C5aR. Secondly, hAb-J and Q were incubated with a series of overlapping peptides (12 mers) comprising the $2^{nd}$ extracellular loop of hC5aR. Thirdly, hAb-J and Q were incubated with a series of mutant peptides comprising a 12 amino acid motif from the $2^{nd}$ extracellular loop of human C5aR with an A1a substitution at each position. Fourthly, hAb-J and Q were incubated with a peptide comprising residues 9-29 from the N-terminal extracellular domain of human C5aR.

Humanized Anti-C5aR Antibody Binds to Chimeric Receptors Containing Human C5aR 2nd Extracellular Loop A series of chimeric receptors comprising either human or mouse C5aR sequences in each of the extracellular domains: the N-terminal domain, and the $1^{st}$, $2^{nd}$ and $3^{rd}$ extracellular loops (ECL) was constructed as described above. The origin of each extracellular domain, as well as the transmembrane and intracellular segments is detailed in Table 6. The origin of the extracellular domains in each construct was defined by a 4-letter code: e.g. mHHH defines a chimeric receptor with the mouse C5aR N-terminus and human C5aR $1^{st}$, $2^{nd}$ and $3^{rd}$ ECLs.

TABLE 6

Chimeric Receptor Constructs: Staining by hAb-Q

| EC Domain Code* | Chimeric Receptor Residues | Sequence Origin | Staining by hAb-Q |
|---|---|---|---|
| 1. HHHH | 1-350 | human C5aR$^a$ 1-350 | +++ |
|  | 351-360 | GTETSQVAPA (bovine rhodopsin tag) |  |
| 2. mHHH | 1-39 | mouse C5aR$^b$ 1-39 | +++ |
|  | 40-350 | human C5aR$^a$ 40-350 |  |
|  | 351-360 | GTETSQVAPA (bovine rhodopsin tag) |  |
| 3. mmHH | 1-111 | mouse C5aR$^b$ 1-111 | +++ |
|  | 112-350 | human C5aR$^a$ 112-350 |  |
|  | 351-360 | GTETSQVAPA (bovine rhodopsin tag) |  |
| 4. mmmH | 1-206 | mouse C5aR$^b$ 1-206 | − |
|  | 207-351 | human C5aR$^a$ 206-350 |  |
|  | 352-361 | GTETSQVAPA (bovine rhodopsin tag) |  |
| 5. mmmm | 1-351 | mouse C5aR$^b$ 1-351 | − |
|  | 352-361 | GTETSQVAPA (bovine rhodopsin tag) |  |
| 6. HmHH | 1-92 | human C5aR$^a$ 1-92 | +++ |
|  | 93-111 | mouse C5aR$^b$ 93-111 |  |
|  | 112-350 | human C5aR$^a$ 112-350 |  |
|  | 351-360 | GTETSQVAPA (bovine rhodopsin tag) |  |
| 7. HHmH | 1-172 | human C5aR$^a$ 1-172 | − |
|  | 173-206 | mouse C5aR$^b$ 173-206 |  |
|  | 207-351 | human C5aR$^a$ 206-350 |  |
|  | 352-361 | GTETSQVAPA (bovine rhodopsin tag) |  |
| 8. HHHm | 1-262 | human C5aR$^a$ 1-262 | +++ |
|  | 263-282 | mouse C5aR$^b$ 264-283 |  |
|  | 283-350 | human C5aR$^a$ 283-350 |  |
|  | 351-360 | GTETSQVAPA (bovine rhodopsin tag) |  |
| 9. Hmmm | 1-92 | human C5aR$^a$ 1-92 | − |
|  | 93-283 | mouse C5aR$^b$ 93-283 |  |
|  | 284-351 | human C5aR$^a$ 283-350 |  |
|  | 352-361 | GTETSQVAPA (bovine rhodopsin tag) |  |
| 10. mHmm | 1-90 | mouse C5aR$^b$ 1-90 | − |
|  | 91-111 | human C5aR$^a$ 91-111 |  |
|  | 112-351 | mouse C5aR$^b$ 112-351 |  |
|  | 352-361 | GTETSQVAPA (bovine rhodopsin tag) |  |
| 11. mmHm | 1-111 | mouse C5aR$^b$ 1-111 | +++ |
|  | 112-262 | human C5aR$^a$ 112-262 |  |
|  | 263-350 | mouse C5aR$^b$ 264-351 |  |
|  | 351-360 | GTETSQVAPA (bovine rhodopsin tag) |  |

*Chimeric receptors are designated by their extracellular (EC) domains: HHHH is human C5aR, Hmmm designates a chimera with the N terminus of human C5aR and the first, second, and third extracellular loops of mouse C5aR, etc.
$^a$human C5aR: SEQ ID NO: 37
$^b$mouse C5aR: GenPept Accession No. NP_031603

The parental anti-C5aR mAb 7F3 exhibited a pattern of staining cells expressing chimeric C5aR that suggested it recognised an epitope in the 2nd extracellular loop (3rd extracellular domain) of human C5aR. To confirm that the humanised antibody hAb-Q, which was derived from mouse mAb 7F3 by CDR grafting, and therefore should contain the same antigen-binding site, had the same staining pattern as 7F3, transiently transfected cells expressing the different chimeric human/mouse C5aR were stained with hAb-Q and analysed by flow cytometry. The chimeric receptors that stained positive are indicated in Table 6. The pattern of staining by hAb-Q was identical to that observed with 7F3. There was no staining by the secondary antibody (anti-hIgG-FITC) alone. Chimeric receptors 1, 2, 3, 6, 8 and 11 were stained with hAb-Q indicating that this antibody recognises an epitope in the human C5aR $2^{nd}$ extracellular loop.

Antibody Binding to Peptides from the Second Extracellular Loop

To further define the epitope in the $2^{nd}$ extracellular loop that the humanized anti-C5aR antibodies bind a set of 22 overlapping peptides (12 mers), each offset by 1 residue from the next, spanning the second extracellular loop of human C5aR was synthesised. The binding of antibodies to these peptides was analysed by peptide ELISA.

The pattern of peptide binding by 7F3 was similar to that by the humanised 7F3 antibodies hAb-Q and hAb-J. The humanized antibodies bound to most strongly to peptides 4 and 5 and peptide 23 (FIGS. 14A and 14B). Peptide 23 is the complete $2^{nd}$ extracellular loop of human C5aR (residues 173-205 from SEQ ID NO:37). There was weaker binding to peptides 1-3 and 6-7. By contrast 7F3 bound strongly to peptides 1-7. Peptides 1-7 contain a common element: the 6 amino acid motif: EEYFPP. The antibodies did not bind to peptides 13-22 which lack this motif, or peptides 8-12 which contain a truncated version of the motif. The anti-C5aR antibodies recognise and bind to a linear epitope (EEYFPP; residues 179-184 from SEQ ID NO:37) on the $2^{nd}$ extracellular loop of the human C5a receptor. The humanized antibodies do not bind to peptides containing the EEYFPP motif close to one or other end, but rather peptides where the motif is located centrally.

Critical Binding Residues within the EEYFPP Motif of the 2nd Extracellular Loop

To further define the critical binding residues in the epitope EEYFPP that the humanized anti-C5aR antibodies bind, a series of short peptides (12 mers) comprising the human C5aR $2^{nd}$ extracellular loop sequence VREEYFPPKVLC (residues 177-188 from SEQ ID NO:37) with alanine substituted at different positions in the binding motif were synthesised. The binding of antibodies to these peptides was analysed by peptide ELISA.

In this experiment, the critical amino acids for binding of the murine anti-C5aR mAb 7F3 were found to be $Y_3$, and $F_4$ in the epitope $E_1E_2Y_3F_4P_5P_6$ (Lee et al., 2006). Like 7F3 the humanised antibodies hAb-J and Q (FIGS. 14C and D respectively) did not bind peptides with A1a substitutions at positions $Y_3$ or $F_4$. In addition, substitutions at $E_1$, $E_2$, and $P_5$ also reduced binding by hAb-J and Q.

The Lead Antibody hAb-Q Does Not Bind to the N-Terminal 9-29 Peptide (PEP1)

The present Example shows that the humanized anti-C5aR antibodies bind to an epitope in the $2^{nd}$ extracellular loop of C5aR. Furthermore, they did not bind chimeric mouse/human C5aR constructs #7 and #9 comprising human N-terminal domain and mouse $2^{nd}$ extracellular loop (see Table 6).

To confirm that the anti-C5aR antibodies did not bind to a linear peptide from the N-terminal domain of human C5aR, the peptide PEP1 having the sequence PDYGHYD-DKDTLDLNTPVDKT (residues 9-29 from SEQ ID NO:37) (SEQ ID NO:59) was synthesised and binding of antibodies to the peptide was analysed by peptide ELISA.

Early studies demonstrated that anti-C5aR mAbs 7F3, 12D4 and 6C12 did not compete with PEP1 binding to human C5aR on transfectants, and nor did these mAbs bind to PEP1 coated on an ELISA plate (WO 03/062278). FIG. 15 shows that the humanized anti-C5aR antibodies hAb-J and Q (at 5 µg/ml) did not bind to PEP1 bound to an ELISA plate at 3 different concentrations (1/100, 1/500 and 1/1000 i.e. 10 µg/ml, 2 µg/ml and 1 µg/ml respectively). However, the anti-C5aR (CD88) mAb S5/1 (AbD Serotec, Cat No. MCA1283) which was raised against the human C5aR N-terminal peptide 1-31 did bind PEP1 at 5 µg/ml as expected.

Example 5

Blocking Migration of Cells Expressing Human C5aR

A. Humanized Antibodies Block Migration of Human Neutrophils

Human neutrophils were isolated from peripheral blood by first obtaining the leucocyte fraction via a dextran sedimentation step for 40 min at room temperature. The cells were then layered onto Ficoll-Paque (GE Healthcare) for density gradient centrifugation at 2500 rpm for 15 min at room temperature. After hypotonic lysis of residual red blood cells, neutrophils were resuspended in chemotaxis buffer (49% RPMI 1640 (Invitrogen), 49% Medium 199 (Invitrogen), 2% dialysed FBS (Invitrogen)). Anti-C5aR antibodies were added to neutrophils ($1\times10^7$/ml) at concentration of 5 µg/ml. A negative control (no Ab addition, but 1×PBS added) was included.

The cells were then loaded into the upper chamber of the insert in the 24-well tissue culture plate (Corning Inc.) with a polycarbonate membrane of 3.0 µm porosity and incubated for 10 min at room temperature. The inserts were then placed onto lower chambers containing human neutrophil chemoattractant recombinant human C5a (Sigma) at a concentration of 0.1 to 100 nM. Maximum neutrophil migration occurred when 1-10 nM C5a was present in the lower chamber. The neutrophils were then incubated for 30 min at 37° C. The number of neutrophils migrating through the membrane to the lower chamber was quantified by flow cytometry (FACSCalibur; BD Biosciences). Relative cell counts were obtained by acquiring events for a set time period of 30 seconds. This method was found to be highly reproducible, and enabled gating on the live cells and the exclusion of debris.

The results presented in FIG. 16 show that the humanized antibodies inhibited human neutrophil migration towards C5a compared to negative (no antibody) controls. At a concentration of 5 µg/ml mouse antibody 7F3, blocked 97% human neutrophil migration. Humanized antibodies G and J, blocked 84% and 82% migration respectively at 5 µg/ml, whereas antibodies C and K were less effective blocking only 75% and 55% neutrophil migration respectively.

B. C5a-Induced Migration of Cells Expressing Human C5aR is Prevented by Humanised anti-C5aR Antibodies In Vitro in a Dose-Dependent Manner Methods Human Neutrophil Migration Human venous blood was collected from healthy volunteers in tubes containing EDTA as anti-coagulent (BD Vacutainer #366457). Neutrophils were purified from the blood by percoll density centrifugation followed by a red blood cell lysis step (Lee et al., 2006). Purified neutrophils were centrifuged at 1,200 rpm for 5 min and resuspended in Chemotaxis buffer (49% RPMI 1640, 49% Medium199, 2% dialysed FBS; GIBCO) at $2 \times 10^7$ cells/ml Chemotaxis buffer. Antibody (diluted in chemotaxis buffer, final concentration 0.003-10 µg/ml) and cells ($2 \times 10^6$ cells/well) in a total volume of 200 µl were incubated at 37° C. in 5% $CO_2$ for ~20 min. This was then split into $2 \times 100$ µl samples and added to 2 wells in the upper chamber of a 24-well transwell plate (HTS Transwell, 3.0 micron pore size; Corning). Chemotaxis buffer (600 µl total) containing C5a (final concentration 0-100 nM) was placed into the lower chamber. Plates were incubated at 37° C. in 5% $CO_2$ for ~1 hr to allow cell migration. Control wells contained cells without antibody, or buffer without C5a. The standard curve for this assay was set up in the 96-well plate with CyQUANT dye as described below.

L1.2/hC5aR Transfectant Cell Migration

L1.2/hC5aR cells growing in RPMI 1640, 10% FBS, 0.5 mg/ml G418 (Invitrogen) and stimulated overnight with 5 mM butyric acid were centrifuged at 1,200 rpm for 5 min and washed in Chemotaxis buffer (49% RPMI 1640, 49% Medium199, 2% dialysed FBS; Gibco), then centrifuged again and finally resuspended at $2 \times 10^6$ cells/ml Chemotaxis buffer. Antibody (diluted in chemotaxis buffer, final concentration 0.005-5 µg/ml) mixed with cells ($1 \times 10^5$ cells/well) in a total volume of 200 µl was added to a 96-well plate and incubated at 37° C. in 5% $CO_2$ for ~20 min. This was split into $2 \times 100$ µl samples and added to 2 wells in the upper chamber of a 96-well transwell plate (HTS Transwell-96 System, 5.0 micron pore size; Corning). Chemotaxis buffer (150 µl total) containing recombinant human C5a (Sigma), final concentration 0.1-100 nM, was placed into the lower chamber. Plates were incubated at 37° C. in 5% $CO_2$ for ~1 hr to allow cell migration. Control wells contained cells without antibody, or buffer without C5a. A serial dilution of hC5aR/L1.2 cells in chemotaxis buffer was prepared to create a standard curve for the CyQUANT® detection assay. Buffer (150 µl), containing a fixed number of cells (0, 150, 450, 1350, 4050, 12150 per well) was added directly to each of two wells in the lower chamber prior to the 1 hr incubation step.

Quantitation Using CyQUANT® Dye

After incubation, buffer plus migrated cells in the transwell lower chamber were transferred to a 96-well flat bottom plate (Nunc) and centrifuged for 5 min at 200×g (~1,500 rpm). The cell pellet was washed with 150 µl PBS to remove traces of phenol red, which interferes with CyQUANT fluorescence. After the second centrifugation step the supernatant was removed carefully and the plate frozen overnight at –80° C. to lyse cells. The plate was thawed at room temperature and 200 µl CyQUANT GR dye diluted in lysis buffer (CyQUANT® Cell Proliferation Assay Kit, Invitrogen) added to each well.

For the assay using the L1.2/hC5aR cells a standard curve was first established in the transwell plate as described in above and the cells transferred to the 96-well plate for labelling with CyQUANT dye. For the assay using neutrophils the standard curve was setup directly in the 96-well plate with CyQUANT dye as follows: a pellet containing $1 \times 10^6$ neutrophils was frozen overnight at –80° C. then thawed and resuspended 1 ml CyQUANT dye, then $2 \times 10^5$ cells in 200 µl was added to each of 2 wells in the 96-well plate containing 200 µl CyQUANT dye and serially diluted 1 in 2 to establish a standard curve (in duplicate) ranging from 100,000 to ~48.8 cells/well.

The plate was incubated at room temperature for 2-5 min wrapped in aluminium foil (to protect from light) then placed in the Fluorimeter (FLUOstar Galaxy, BMG Labtechnologies) and read with excitation maximum (A1) set at 485 nm and the emission maximum (B1) set to 520 nm. Fluorescence intensity was recorded and data processed using FLUOstar Control software. Fluorescence intensity was converted to cell number using the standard curve, with data analysed using either linear regression or non-linear 4-parameter log equation (GraphPad Prism v4.0).

Results

The ability of humanised 7F3 antibodies to block C5a-induced migration of human neutrophils and hC5aR/L1.2 cell transfectants over a range of concentrations was investigated.

Neutrophils from 4 different healthy volunteer donors were pre-incubated with various concentrations of anti-C5aR antibody hAb-Q or 7F3 or isotype control antibodies prior to exposure to 10 nM C5a in the transwell assay. Samples were run in duplicate. The number of migrating cells was calculated after background fluorescence was subtracted from the standard curve using regression analysis. For each experiment the standard curve fitted equation $r^2$ value was >0.99.

There was a dose-response relationship exhibited by the anti-C5aR antibodies. At a concentration of 10 µg/ml both hAb-Q and 7F3 completely blocked migration of human neutrophils induced by 10 nM C5a. As the concentration of antibody decreased the number of migrating cells increased. Preincubation of neutrophils with hAb-Q or 7F3 at a concentration below 0.1 µg/ml was not effective in preventing migration. The isotype control antibodies did not block C5a-induced chemotaxis of human neutrophils. FIG. 17 shows the average data from the 4 experiments plotted with the non-linear regression line of best fit shown for hAb-Q and 7F3. The humanised anti-C5aR antibody was more effective at blocking C5a-induced human neutrophil migration than 7F3 with a ~6-8 fold lower $IC_{50}$.

Transfected cells expressing human C5aR were also subjected to a migration assay after pre-incubation with various concentrations of anti-C5aR antbodies hAb-Q, hAb-J or 7F3 or an isotype control antibody. FIG. 18 shows hC5aR/L1.2 transfectant migration was completely inhibited by humanized anti-C5R antibodies J and Q, aas well as 7F3, at 5 µg/ml. Analysis of the data using non-linear regression with a sigmoidal dose-response equation (GraphPad Prsim software) gave $IC_{50}$ values of 0.5, 0.6 and 0.7 µg/ml for 7F3, J and Q respectively, suggesting that the antibodies were each very effective at neutralising C5a-induced migration of hC5aR/L1.2 cells.

C. Humanized Anti-C5aR Antibody Efficiently Blocks Human Neutrophil Migration In Vitro at Low Levels of Receptor Occupancy It was shown above that humanized anti-C5aR antibodies inhibited C5a-induced migration (chemotaxis) of cells expressing human C5aR. To further characterise this inhibition, the level of C5a receptor occupancy by humanized anti-C5aR antibody required to inhibit human neutrophil migration in vitro was determined as follows.

Methods

FITC-Labelling of hAb-Q

Fluorescein isothiocyanate (FITC) was covalently conjugated to hAb-Q. Briefly, ~2.2 mg of hAb-Q was exchanged into "Reaction Buffer" (160 mM $Na_2CO_3$, 340 mM NaHCO3, pH 9.5) and the 1.8 mg recovered was added to 144 µg FITC (Molecular Probes, Cat. No. F1906) dissolved in DMSO. The reaction was performed in the dark for 1 hr at room temperature (~21° C.). Unconjugated FITC was removed using a PD-10 column, pre-equilibrated and eluted with "Storage Buffer" (10 mM Tris, 150 mM NaCl, pH 8.2). Conjugated hAb-Q-FITC was concentrated to achieve a final concentration of 5.7 mg/ml using a Centricon YM-30 spin filter (Amicon, Cat. No. 4208) and stored at 4° C. in the dark.

Binding hAb-Q to C5aR on Human Neutrophils

Human neutrophils, prepared as described above but without a red blood cell lysis step, were centrifuged at 1,200 rpm for 5 min and resuspended at $2 \times 10^7$ cells/ml in Chemotaxis buffer (49% RPMI 1640, 49% Medium199, 2% dialysed FBS; Gibco). Antibody hAb-Q was diluted in Chemotaxis buffer to 2× the required final concentration. Concentrations of 0.002, 0.006, 0.02, 0.06, 0.2, 0.6, 2, 6, 20, 60, 200 and 600 µg/ml were prepared. An equal volume of cells (125 µl) and antibody (125 µl) were mixed and incubated at 37° C. for 10 min to allow hAb-Q to bind to C5aR.

Human Neutrophil Chemotaxis Assay

Briefly, after incubation of neutrophils and hAb-Q, 100 µl aliquots of each mix containing $2 \times 10^6$ cells and 0 to 100 µg/ml hAb-Q were placed (in duplicate) into the upper chamber of a 24-well transwell plate (6.5 mm insert, 3.0 micron polycarbonate membrane; Corning Costar, Cat. No. 3415). Chemotaxis buffer (600 µl total) containing recombinant human C5a (final concentration 0, 0.1, 1, 10 or 100 nM) was placed into the lower chamber. Plates were incubated at 37° C. in 5% $CO_2$ for 30 min to allow cell migration. Control wells contained cells without antibody, or buffer without C5a. After incubation the number of cells in the lower chamber was counted by flow cytometry on a FACSCalibur (BD Biosciences).

Measurement of Bound hAb-Q

The amount of bound hAb-Q on human neutrophils was calculated in 2 samples: a sample of the cells plus antibody mix before chemotaxis (sample A) and a sample of cells from the lower chamber of the transwell plate after chemotaxis (sample BL). This was to determine whether there was any difference in receptor occupancy of cells that had migrated or whether the receptor occupancy changed between the start and end of chemotaxis. Bound hAb-Q was detected by incubating cells with anti-hIgG-FITC. In some assays the amount of bound antibody was measured in a third sample—a sample of cells plus antibody mix from the upper chamber of the transwell plate after chemotaxis (Sample BU).

Sample A (10 µl cells plus antibody before migration) was added to a well of a 96-well U-bottom plate (in duplicate) and centrifuged at 1,200 rpm for 2 min at room temperature in a bench-top centrifuge (Beckmann Coulter Allegra X-15R). The cell pellet was washed twice with 200 µl PBS before being resuspended in 50 µl of anti-hIgG-FITC (1/300, diluted in dPBS) and incubated at room temperature for 30 min. Samples were centrifuged at 2,000 rpm for 2 min, supernatant was removed and cell pellet resuspended in 150 µl FACS Buffer (PBS, 1% BCS) for analysis by flow cytometry (FACSCalibur, BD Biosciences).

Samples BL (200 µl cells from the lower chamber of the transwell plate after migration) and BU (50 µl cells+antibody mix from the upper chamber of the transwell plate after migration) were placed in wells of a 96-well U-bottom plate (in duplicate) and processed as described for Sample A.

Measurement of 'Free' C5a Receptor

The amount of free receptor on human neutrophils was calculated in 2 samples: a sample of the cells plus antibody mix before chemotaxis (sample C) and a sample of cells from the lower chamber of the transwell plate after chemotaxis (sample D). Free receptor was detected by incubating cells with FITC-labelled hAb-Q (hAb-Q-FITC).

Sample C (10 µl cells plus antibody before migration) was added to a well of a 96-well U-bottom plate (in duplicate) and centrifuged at 2,000 rpm for 2 min at room temperature. The cell pellet was washed twice with 200 µl PBS before being resuspended in 50 µl of hAb-Q-FITC (100 µg/ml, diluted in dPBS) and incubated at room temperature for 30 min. Samples were centrifuged at 2,000 rpm for 2 min, supernatant was removed and the cell pellet resuspended in FACS Buffer (PBS, 1% BCS) for analysis by flow cytometry (FACSCalibur, BD Biosciences).

Sample D (200 µl cells from the lower chamber of the transwell plate after migration) was placed in a well of a 96-well U-bottom plate (in duplicate) and processed as described for Sample C.

Flow Cytometry Analysis of Neutrophil C5a Receptor Occupancy

The FACSCalibur flow cytometer was set up with compensation parameters established for channel FL-1. Samples were acquired to exclude dead cells and debris. Neutrophils were identified based on FSC and SSC. The level of bound hAb-Q (anti-hIgG-FITC) or free C5aR (hAb-Q-FITC) was determined by determining the FITC (FL-1) mean fluorescence intensity (MFI) of the neutrophils in a sample.

Percent bound hAb-Q was quantified by determining the MFI of each sample A and B, as a percentage of the MFI of the sample incubated with 300 µg/ml hAb-Q (after subtraction of non-specific background (NSB) which was the MFI of the samples without hAb-Q) according to the following equation:

% Occupied Receptor=[$MFI$(sample)–$MFI$($NSB$)]/
[max $MFI$(300 µg/ml hAb-$Q$ sample)–$MFI$
($NSB$)]×100

Percent free C5a receptor was quantified by determining the MFI of each sample C and D, as a percentage of the maximum MFI of the samples incubated without hAb-Q (after subtraction of non-specific background (NSB) which was the MFI of the sample incubated with 300 µg/ml unlabelled hAb-Q) according to the following equation:

% Free Receptor=[$MFI$(sample)–$MFI$($NSB$)]/[max
$MFI$(no unlabelled hAb-$Q$ sample)–$MFI$($NSB$)]×
100

Results

Four experiments were carried out. Briefly, purified neutrophils isolated from the venous blood of a healthy volunteer were preincubated for 10 min with hAb-Q at concentrations ranging from 0.001 to 100 µg/ml. A small aliquot of this mix was taken to determine the amount of antibody bound receptor (% receptor occupancy) and the remainder was placed in the upper chamber of a transwell plate. C5a (10 nM) was placed in the lower chamber. After 30 min incubation, the number of cells that had migrated into the lower chamber was determined using FACS. The amount of bound antibody on the neutrophils in both the lower and upper chambers at the end of migration was also determined, using FITC-labelled anti-hIgG and flow cytometry. The level of free receptor (no bound antibody) was determined in one experiment by incubating the neutrophils with FITC-labelled hAb-Q before and after migration.

Migration of Neutrophils was Blocked by hAb-Q

FIG. 19 shows the plot of hAb-Q concentration vs. total number of migrating cells, generated from the combined data of the four experiments. There was a dose-response relationship between hAb-Q concentration and migration. At a concentrations $\geq 0.1$ µg/ml hAb-Q completely blocked migration of human neutrophils induced by 10 nM C5a. As the concentration of antibody decreased the number of migrating cells increased. This result was similar to that described above (FIG. 17).

Receptor Occupancy Increased with Increasing Concentration of Antibody

The receptor occupancy data from the 4 experiments was combined. The average amount of bound antibody (occupied receptor) on neutrophils at each concentration of hAb-Q in the pre-chemotaxis and post-chemotaxis lower transwell chamber samples is shown graphically in FIG. 20. The difference in the level of occupied receptor between the pre-chemotaxis samples and the post-migration samples from the lower transwell chamber ($EC_{50}$ values 0.3 and 1.1 µg/ml respectively). At any given concentration of hAb-Q there was less antibody bound to cells in the post-chemotaxis than pre-chemotaxis. This difference might be because the cells that preferentially migrated could have, on average, less hAb-Q blocking the receptor than cells that did not migrate. An alternative explanation for the difference might be that the premixed cells plus antibody solution (100 µl) was essentially diluted ~7 fold when placed in the transwell plate containing 600 µl buffer in the lower chamber. As antibody could freely cross the transwell 3 µm membrane, becoming diluted, the equilibrium of the binding reaction would change.

The amount of free receptor after unlabelled hAb-Q binding was measured in one experiment. This data is also shown graphically in FIG. 20. An inverse relationship between bound and free receptor in both the pre-chemotaxis and post-chemotaxis samples was observed.

Relationship between Receptor Occupancy and Inhibition of Chemotaxis

The neutrophil migration data shown in FIG. 19 was transformed by expressing the number of migrating cells as a percentage of the average number of cells migrating to 10 nM C5a in the samples without antibody. This percentage was then subtracted from 100% to obtain percentage inhibition of migration. Thus the number of migrating cells in the no antibody sample became 0% inhibition, and 0 migrating cells became 100% inhibition. This data was then analysed using GraphPad Prism using non-linear regression (sigmoidal dose-response (variable slope) equation). The curve obtained after this analysis was then plotted with the receptor occupancy data from FIG. 20 to generate FIG. 21.

FIG. 21 shows that increased receptor occupancy correlated with increased inhibition of neutrophil migration. The $EC_{50}$ value for inhibition of migration was 0.03 µg/ml, and for receptor occupancy it was 0.3 µg/ml for the pre-chemotaxis samples and 1.1 µg/ml for the post-chemotaxis samples from the lower transwell chamber. The data suggests that very low receptor occupancy was associated with significant blocking of migration. Only 10% of receptor had bound antibody at 0.03 µg/ml hAb-Q, but this dose caused a 50% drop in migration. Migration was completely blocked at a concentration of 0.3 µg/ml when receptor occupancy was ~15-45%. In conclusion, hAb-Q was very effective at blocking C5a-mediated human neutrophil migration in vitro, at low levels of receptor occupancy.

Example 6

Humanized Antibodies Block C5a-Induced Calcium Ion Release from Human Neutrophils Calcium mobilization is one of the first events to occur after C5a binds to its receptor, C5aR on the surface of the neutrophil. C5a binding causes an immediate rise (within seconds) in cytosolic free $Ca^{2+}$ that is released from internal stores, followed by a more sustained effect (over minutes) due to influx from the extracellular medium. This transient increase in free $Ca^{2+}$ acts as a secondary messenger for the various biological responses observed in neutrophils after C5a binding to C5aR.

To determine whether the humanized 7F3 antibodies were effective in blocking C5a-induced $Ca^{2+}$-release a "Calcium flux" assay was carried out as follows. Briefly, human neutrophils were isolated from a healthy volunteer and purified as described above. For each sample, $1 \times 10^6$ neutrophils were required. The neutrophils were centrifuged and washed in PBS then resuspended at $1 \times 10^7$ cells/ml in Cell Dye (Complete MGB [5 mM KCl, 140 mM NaCl, 300 µM $MgSO_4$, 1 mM $MgCl_2$, 220 µM $KH_2PO_4$, 1.1 mM $NaHPO_4$, 10 mM HEPES, 5.5 mM glucose] with 250 µM sulfinpyrazone and 1.7 µM Fluo3-AM (Calbiochem, Cat. No. 343242) or Fluo4-AM (Invitrogen)) and incubated at room temperature for 40 min in darkness. Cells were centrifuged and washed with Complete MGB plus 250 µM sulfinpyrazone to remove excess dye, centrifuged again and resuspended at $2 \times 10^6$ cell/ml with Complete MGB plus 250 µM sulfinpyrazone. Cells (0.5 ml) were aliquoted into non-sterile glass FACS tubes—one tube for each sample—and used within an hour. Various reagents (C5a, ionomycin, antibody) were prepared at 10× final concentration in Incomplete MGB (Complete MGB minus HEPES and glucose). The FACSCalibur flow cytometer (Becton Dickinson) was set up and neutrophils gated using x-axis forward scatter, y-axis side scatter. The y-axis FL-1 (FITC) channel was used to check neutrophil response. Sample fluorescence was measured continuously and data saved in a CellQuest file. Various control tests were run before other samples—cells without treatment were used to establish baseline fluorescence. C5a was added to cells (50 µl of 10 nM recombinant human C5a (Sigma): final concentration 1 nM) to test the response. Without antibody pre-treatment the cells responded immediately to hC5a if functional; if no response was obtained cells were not suitable. Ionomycin (0.1-1 µg/ml final concentration in tube) was used to determine whether the cells had been loaded with dye.

To determine whether the humanized 7F3 antibodies were effective in blocking C5a-induced $Ca^{2+}$-release neutrophils loaded with dye were preincubated with anti-C5aR antibody (0.1-50 µg/ml final concentration in tube) for 10-25 min. Then cells plus antibody were run through the flow cytometer to obtain a baseline reading followed by addition of 1 nM hC5a (final concentration). If hC5a did not produce a spike in fluorescence then ionomycin (Sigma, 0.1-1 µg/ml final concentration) was added to check the cells were capable of responding (viable).

The ability of the original mouse anti-human C5aR mAb 7F3 to block C5a-induced $Ca^{2+}$ release was investigated. A concentration of 10 µg/ml 7F3 completely blocked C5a-induced $Ca^{2+}$ flux, 1 µg/ml was partly effective, whereas lower concentrations (0.01 and 0.1 µg/ml) did not block $Ca^{2+}$ release. The cells incubated with 10 µg/ml 7F3 were still capable of releasing $Ca^{2+}$ as evidenced by the increase in mean fluorescent intensity (MFI) when 1 µg/ml ionomycin was added ~30 sec after C5a (data not shown).

The humanized 7F3 antibodies (F, G, J, M, N and O) were tested for their ability to neutralise C5a-induced calcium release in human neutrophils at a concentration of 10 µg/ml when incubated with neutrophils about 10 min before adding 1 nM C5a. Antibodies N and O completely blocked $Ca^{2+}$ flux, whereas antibodies F, G, J and M partially blocked $Ca^{2+}$ release as suggested by the lower mean fluorescence values observed compared to control cells not preincubated with antibody. When ionomycin was added to cells preincubated with antibody N or O there was an immediate increase in MFI demonstrating that the neutrophils remained capable of $Ca^{2+}$ release in the presence of the blocking antibody (data not shown).

The dose-response relationship for antibodies G, J, M, N and Q was examined by pre-incubating human neutrophils with various concentrations of antibody before adding C5a and measuring $Ca^{2+}$ release. A concentration of 30 µg/ml antibody G completely blocked C5a-induced $Ca^{2+}$ release, whereas lower concentrations (0.1, 1, 10 μg/ml) were not effective. The results were the same for antibody M. In both cases, the cells treated with 30 μg/ml antibody were still capable of releasing $Ca^{2+}$ as shown when 1 μg/ml ionomycin was added about 90 sec after C5a. Antibody J showed complete blocking at concentrations of 30 and 10 μg/ml, although in the previous experiment 10 μg/ml antibody J was only partly effective at blocking $Ca^{2+}$ flux. Antibody N was the most effective antibody, completely blocking C5a-induced $Ca^{2+}$ release at 10 and 1 μg/ml in 2 separate experiments. In all cases when C5a failed to cause $Ca^{2+}$ flux 1 ug/ml ionomycin was added and produced a large increase in MFI indicating the cells were still capable of responding. With antibody Q, C5a-induced $Ca^{2+}$ release from human neutrophils was prevented when the cells were preincubated with 5 or 50 μg/ml of antibody Q, as evidenced by the lack of a peak in fluorescence upon addition of 1 nM C5a. Addition of ionomycin to these samples a short time later generated the usual increase in fluorescence suggesting that the neutrophils were still capable of responding. Preincubation with 0.5 μg/ml of antibody Q was not effective and a large increase in fluorescence was observed after 1 nM C5a was added to the sample, similar to the effect seen when cells were treated with 1 nM C5a only (no antibody added). These results are summarised in Table 7.

TABLE 7

Calcium Flux Assay Results Showing Concentrations of Each Antibody Effective at Blocking C5a-Induced $Ca^{2+}$-Release.

| Antibody | Ab conc. effective at blocking C5a-induced $Ca^{2+}$-flux | Ab conc. tested but not effective at blocking $Ca^{2+}$-flux |
|---|---|---|
| F^ | — | 10 μg/ml |
| G | 30 μg/ml | 0.1, 1 & 10 μg/ml |
| J | 10# & 30 μg/ml | 0.1 & 1 μg/ml |
| M | 30 μg/ml | 1 & 10 μg/ml |
| N | 1 & 10 μg/ml | 0.01 & .01 μg/ml |
| O^ | 10 μg/ml | — |
| Q | 5 & 50 μg/ml | 0.5 μg/ml |
| 7F3 | 1# & 10 μg/ml | 0.01 & 0.1 μg/ml | this concentration was partly neutralising in one experiment, but completely neutralising in another.
^only a single Ab concentration tested.

Table 7 shows that the most effective blocking humanized 7F3 antibodies were antibodies N and Q. Interestingly, antibody N is isotype IgG1 and may be more effective than antibodies with isotype IgG4 because of binding to Fcγ receptors (Fc gamma R) on the neutrophils. Human IgG1 has higher affinity for Fc gamma R than hIgG4. To determine whether Fc gamma R binding by antibody N or O contributed to neutralisation of C5a-mediated $Ca^{2+}$ release human neutrophils preloaded with Fluo3-AM were preincubated for 10 min with antibody O or N alone, or antibody N plus 50 μl Fc block [human serum prepared from the same blood sample the neutrophils were isolated from], or antibody O plus Fc block, or Fc block alone. Changes to intracellular $Ca^{2+}$ levels in response to C5a (and ionomycin if necessary) were measured on the flow cytometer. There was no difference in the ability of antibodies N or O to neutralise C5a-induced $Ca^{2+}$ flux in the presence or absence of Fc block. These cells were still capable of $Ca^{2+}$ release as shown by the effect of adding ionomycin. Preincubating the neutrophils with Fc block alone did not prevent C5a-induced $Ca^{2+}$ release. These data suggest antibodies N and O exert their protective effect through binding to C5aR and blocking C5a signalling, not through interaction with the Fc gamma R.

Example 7

Influence of Humanized Anti-C5aR Antibodies on Neutrophil Activation

A. Humanized Anti-C5aR Antibodies Prevent C5a-Induced Activation of Human Neutrophils In Vitro C5a is a potent activator of human neutrophils, inducing up-regulation of surface antigen CD11b (alpha chain of MAC-1 integrin, mediates chemotaxis and interactions with endothelium), and loss of the adhesion molecule CD62L (L-selectin). The ability of the humanized anti-C5aR antibodies to prevent C5a-mediated neutrophil activation was investigated in a whole blood activation assay.

Methods

Blood from healthy human volunteers (2 donors) was collected in tubes containing the anti-coagulant Acid Citrate Dextrose (ACD) and added to wells containing $H_2DCFDA$ (final 50 μM) for 10 min at room temperature (23° C.), followed by 0.3-300 μg/ml hAb-Q, 0.3-300 μg/ml IgG4 isotype control, or dPBS only. Samples were incubated at room temp. (23° C.) for 20 min. C5a (100 nM final), PMA (0.2-400 ng/ml), or dPBS was added to each sample and again incubated at room temp. (23° C.) for 20 min. Anti-CD11b and anti-CD62L antibodies (1/400final) were added to all samples for 15 min. Erythrocytes were removed using RBC lysis buffer and leukocytes resuspended in dPBS+1% FCS.

CD11b and CD62L expression levels on neutrophils were measured as follows. The FACSCalibur flow cytometer (BD biosciences) was set up with compensation parameters established for channels FL-2 and FL-4. Samples were acquired to exclude dead cells and debris. Neutrophils were identified as having high FSC and SSC and the PE (FL-2) and APC (FL-4) median fluorescence intensity (MFI) of these cells was measured.

CD11b and CD62L expression levels (MFI) were reported as % of maximal expression using the formula:

% max expression=[(sample−minimum expression)/(maximum expression−minimum expression)]×100

Note. Maximal expression was the No Antibody (dPBS only)+100 nM C5a sample for CD11b, and No Antibody (dPBS)+0 nM C5a (dPBS) sample for CD62L (as CD62L is reduced on activated neutrophils).

The $IC_{50}$ values for hAb-Q neutralisation of C5a-mediated changes in CD11b and CD62L expression were calculated using GraphPad Prism (v4.0) software. Data was fitted using non-linear regression to a sigmoidal dose-response (variable slope) equation for each experiment as well as the average of the two experiments.

Results

The blocking effect of hAb-Q on C5a-induced neutrophil activation was assessed in a whole blood assay using 2 donors. In samples activated with C5a, CD11b expression increased in the absence of hAb-Q. But this increase in CD11b expression was prevented if hAb-Q was present, in a dose-response manner with an IC50 value ~10.7 μg/ml (FIG. 22). The isotype control antibody did not prevent C5a-induced up-regulation of CD11b expression even at >100 μg/ml (data not shown).

The humanised anti-C5aR antibody hAb-Q also prevented C5a-induced loss of CD62L in a dose dependent manner with an IC50 value of ~5.4 μg/ml (FIG. 23). The isotype control antibody did not prevent C5a-induced loss of CD62L even at >100 μg/ml (data not shown).

B. Humanized Anti-C5aR Antibodies Did Not Activate Human Neutrophils In Vitro in Solution The ability of the humanized anti-C5aR antibody to neutralize C5a-induced activation of neutrophils was described above. In the following experiment the humanized anti-C5aR antibody was incubated with purified human neutrophils in the absence of C5a which did not change the expression of cell surface markers, CD11b and CD62L. These experiments demonstrated that the anti-C5aR antibody does not activate cells in solution per se.

Methods

Human Neutrophil Activation Assays and Measurement of CD11b and CD62L Expression Human peripheral venous whole blood was incubated ex vivo with humanised anti-hC5aR antibodies hAb-Q, hAb-J or hAb-G in a series of experiments. Neutrophil activation was measured by determining CD11b and CD62L expression levels as described below. Falls in CD62L levels or increases in CD11b levels are markers of neutrophil activation.

Experiment 1

Briefly, heparinised whole human blood from a healthy donor was added to either: 1, 10, or 100 µg/ml of hAb-J or hAb-Q, 10 µM fMLP (formyl Met-Leu-Phe peptide), or dPBS only. Samples were incubated at 37° C. in 5% $CO_2$ for 1 hour before addition of anti-CD11b-PE and anti-CD62L-APC antibodies at a final dilution of 1/100. Erythrocytes were removed using RBC lysis buffer and leukocytes were resuspended in dPBS+1% FCS.

The FACSCalibur (BD) flow cytometer was set up with compensation parameters established for channels FL-2 and FL-4. Samples were gated to exclude dead cells and debris. Neutrophils were identified as having high FSC and SSC. The median fluorescence intensity (MFI) of these cells in the FL-2 (CD11b-PE) and FL-4 (CD62L-APC) channels was calculated. The level of CD11b (PE) and CD62L (APC) was determined for each sample and reported as fold-expression relative to the dPBS control.

Experiment 2

Heparinised blood from 4 healthy volunteers was added to tubes containing either: 0.1, 1, 10 or 100 µg/ml of hAb-G, hAb-J, 10 nM or 100 nM human C5a or dPBS only. After 20 min at 37° C., 6% dextran (final conc. 1%) was added to each tube and allowed to sit for 30 min to sediment erythrocytes. The upper leukocyte-rich plasma layer was transferred to a 96-well plate where cells were washed in cold dPBS. After centrifugation the supernatant was removed and cells resuspended in dPBS containing anti-CD11b-PE (1/50) and anti-CD62L-APC (1/50) then incubated on ice for 30 min. Cells were once again washed and resuspended in dPBS+1% FCS. CD11b and CD62L expression levels on neutrophils were measured as described above.

Experiment 3

Blood from healthy human volunteers (2 donors) was collected in tubes containing the anti-coagulant Acid Citrate Dextrose (ACD) and processed as described above in Example 7A except no C5a was added to samples. CD11b and CD62L levels on neutrophils were measured by FACS as described in Example 7A.

Results

CD11b and CD62L Expression on Human Neutrophils was not Altered in a Whole Blood Assay with Humanized Anti-C5aR Antibodies.

In the first experiment, human whole blood was incubated with 1, 10, or 100 µg/ml of hAb-Q or hAb-J, 10 µM fMLP, or dPBS for 1 hr at 37° C. and expression of CD11b and CD62L measured by flow cytometry. There was no increase in CD11b or decrease in CD62L expression in samples containing hAb-Q or hAb-J at any concentration from 1-100 µl/ml (FIGS. 24A and 24B). In contrast, the peptide fMLP, which is known to activate granulocytes, produced a large increase in CD11b expression and loss of CD62L.

In a second experiment, human whole blood from 4 donors was incubated with 0.1-100 µg/ml of humanized anti-C5aR antibodies hAb-G or hAb-J; 10-100 nM human C5a; or dPBS for 20 min at 37° C. Expression of CD11b and CD62L on neutrophils relative to expression in the dPBS control after treatment is shown in FIGS. 25A and 25B respectively. Neither hAb-G nor hAb-J induced up-regulation of neutrophil CD11b or loss of expression of CD62L in any of the samples tested. In contrast 10 nM and 100 nM C5a produced 2.5 and 3.0 fold increases in CD11b expression relative to dPBS respectively, whilst CD62L expression fell to 0.33 and 0.14 of the level in the dPBS control respectively. Like fMLP, C5a is known to activate granulocytes.

In a third experiment, whole blood from 2 healthy volunteers was added to 0.3-300 µg/ml of hAb-Q or an isotype control antibody, then 100 nM C5a or dPBS was added to each sample. Neutrophil CD11b and CD62L expression was measured by flow cytometry and results are shown in FIGS. 26a and 26b. The level of CD11b expression did not change (increase) in samples containing hAb-Q or the isotype control antibody in PBS indicating no activation at any antibody concentration up to 300 µg/ml (FIG. 26a). However, when 100 nM C5a was added to samples containing the isotype control antibody, CD11b expression increased to the maximum level as measured in a sample containing 100 nM C5a and no antibody. CD62L expression was at its maximum (no activation) in samples without C5a. Addition of hAb-Q or the isotype control antibody at concentrations up to 300 µg/ml did not reduce the level of CD62L expression i.e. did not activate the neutrophils (FIG. 26b). By contrast, samples containing the isotype control antibody and 100 nM C5a lost CD62L expression and were maximally activated.

In summary, the results demonstrate that humanized anti-C5aR antibodies do not activate human neutrophils, as indicated by CD62L and CD11b expression levels after incubation in whole human blood ex vivo.

C. hAb-Q Does Not Activate Human Neutrophils In Vitro When Bound to a Solid Support Superoxide is one of the reactive oxygen species that activated neutrophils produce to combat pathogens. However, superoxide may also have adverse effects on normal tissue. The possibility that the anti-C5aR antibody in itself could stimulate the production of superoxide by neutrophils was investigated. The experiments described below show that the humanized anti-C5aR antibody hAb-Q does not stimulate human neutrophils to produce superoxide, but is able to counteract its production when human neutrophils are stimulated by C5a.

Methods

Measurement of Superoxide Production In Vitro by Isolated Human Neutrophils

Superoxide ($O_2^-$) is the first oxygen-containing substance made by NADPH oxidase when neutrophils are activated by inflammatory mediators e.g. C5a. Some of the $O_2^-$ is excreted extracellularly. Cytochrome C ($Fe^{3+}$), which is membrane impermeable, is reduced by superoxide to cytochrome C ($Fe^{2+}$) which can be detected spectophotometrically at 550 nm. In the present study, a 96-well plate was used to determine the reduction of cytochrome C spectophotometrically using a Wallac Victor[2] (Mayo and Curnutte, 1990).

Preparation of Human Neutrophils

Human neutrophils were purified as described in Example 5B above. 96-well microtiter plates were coated overnight with human fibrinogen (1 mg/ml). To each well was added 100 µl Cytochrome C (150 µM) and 200,000 neutrophils in 50 µl RM (reaction mixture consisting of HBSS (Cat # 14175 Gibco) plus 0.4 mM $MgSO_4$, 0.5 mM $MgCL_2$, 0.5 mM $CaCl_2$ and 20 mM HEPES and pH set at 7.4). The plate was inserted in the Wallac Victor[2] (Perkin-Elmer) at 37° C. and unstimulated $O_2^-$ production measured every min during a 4 min period. Next antibodies were added in 15 µl RM and the wells measured every 2 min for 10 min. Finally C5a was added and the plate measured every 2 min for 30 min followed by measurements every 10 min for 60 min. The values measured after 1.5 h were used as results. Four wells were used for each group.

Results

Neutrophils from 2-6 healthy donors were used in this study. FIG. 27 shows the production of superoxide after 1.5 h incubation at 37° C. Reaction mixture (RM) was used as a control (6 donors). The inflammatory mediator C5a induced a robust $O_2^-$ production (6 donors) which was counteracted by the anti-C5aR-antibody hAb-Q (5 donors). In this study a high concentration of antibody was used to ensure that any stimulatory effects were not overlooked. It is evident that hAb-Q at 1000 µg/ml (4 donors), 250 µg/ml (3 donors) and 100 µg/ml (2 donors) as well as a control, irrelevant $IgG_4$ antibody HzATNP (2 donors), which is a humanized version of the murine antibody A-TNP, was without stimulatory effects.

In summary, the results described above demonstrate that the humanized anti-C5aR antibody hAb-Q did not stimulate human neutrophils to produce the free radical $O_2^-$. On the contrary it was able to counteract the production elicited by C5a.

Example 8

Humanized Anti-C5aR Antibodies Do Not Deplete White Blood Cells in an Ex Vivo Whole Human Blood Assay To determine whether the hAb-Q was capable of killing or depleting other human cells expressing C5aR, particularly neutrophils and monocytes in blood, several ex vivo whole blood depletion assays were carried out. The whole blood depletion studies used an anti-coagulant, lepirudin (Refludan®), which does not inactivate complement- or antibody-mediated killing mechanisms (CDC, ADCC). Lepirudin is a highly specific direct thrombin inhibitor. It is a recombinant analogue of the anti-coagulant hirudin extracted from the leech.

Methods

Blood Collection

Peripheral venous blood was collected from healthy volunteers into a sterile 15 ml polypropylene tube containing a final concentration of 50 or 500 µg/ml lepirudin (Refludan®, Pharmion Pty Ltd, Melbourne, Australia).

Incubation with Antibodies

Aliquots (50 µl) of the anti-coagulated blood were distributed into a 96-well plate and incubated with 25 µl antibody diluted in dPBS at a final concentration of 100 µg/ml, in duplicate, for 3.5 hours at 37° C. in 5% $CO_2$. Control samples comprised 50 µl blood plus 25 µl dPBS. A staining cocktail (25 µl) comprising anti-hCD66b-FITC (1/100final), anti-hCD19-APC (1/300 final) and anti-hCD14-PE (1/300 final) was added to each sample and incubation continued for 30 min at 37° C. in 5% $CO_2$. Then calibration beads (50µl, 980 beads/µl; Flow-Count Fluorospheres; Beckman Coulter, USA; Cat. No. 7547053) were added to each sample. Erythrocytes were lysed by adding 100 µl 1×FACS Lysing Solution (10×FACS Lysing Solution; BD Biosciences; Cat. No. 349202). The entire sample was transferred to a 1.5 ml tube, and a further 500 µl 1×FACS Lysing Solution was added. Tubes were centrifuged at 4,000 rpm for 3 min and the supernatant removed. Cells and beads were resuspended in 150 µl FACS buffer (dPBS+1% BCS).

FACS Analysis

Cells were analysed on a FACSCalibur (Becton Dickinson) flow cytometer. Forward and side scatter was used to include all cells but exclude debris. Gates were set to count CD66b-FITC (FL-1) positive cells (neutrophils), CD19-APC (FL-4) positive cells (B lymphocytes) or CD14-PE (FL-2) positive cells (monocytes). The number of cells per 5000 beads was determined.

The total number of each cell type per millilitre blood was calculated as follows:

cells/ml=#cells in 5000 beads×(50×980)/5000×1000/50

The percent depletion was calculated as follows:

% depletion=100×(1−(#cells/ml Ab treated sample/#cells/ml *PBS* treated sample))

Results

Three separate experiments were carried out using whole peripheral venous blood from 3 different healthy volunteers collected in sterile tubes containing lepirudin. The blood was incubated with humanized anti-C5aR antibody hAb-Q, rituximab (positive control anti-CD20 antibody), hIgG4 (negative isotype control antibody) or PBS (buffer control, baseline to measure the extent of cell depletion). At the end of the incubation, cells were stained using a cocktail of labelled antibodies to CD66b, CD14 and CD19 to identify granulocytes (neutrophils: CD66b+ve), monocytes (CD66b−ve, CD14+ve) and B cells (CD19+ve). To determine the absolute number of each cell type a fixed volume of calibration beads with known concentration was added to each sample. Therefore it was possible to determine the absolute number of neutrophils (granulocytes), monocytes and B cells in each sample (as cells/ml) as well as the relative depletion of each cell type after treatment with antibody expressed as a percentage of the total number of cells in the sample incubated with PBS.

The data from the 3 experiments was averaged and the results are presented in FIGS. 28 and 29. FIG. 28 shows the average number of cells (±standard deviation) calculated from the 3 sets of data. FIG. 29 shows the average percentage depletion of each cell type (±sd) relative to the number of cells in the PBS-treated sample. The data shows that there was no depletion of neutrophils or monocytes after 4 hours incubation with hAb-Q. By contrast, rituximab caused ~70% depletion of B cells (which express CD20, the target for rituximab), but did not reduce the number of monocytes or neutrophils, cell types that do not express CD20.

Example 9

Humanized Anti-C5aR Antibody hAb-Q Does Not Kill C5aR-Expressing Cells via Complement Mediated Lysis It was desirable to develop a humanized anti-C5aR antibody that did not kill C5aR-expressing cells (neutrophils, monocytes, etc). Antibodies can initiate killing of cells expressing the target antigen by a number of mechanisms. hAb-Q was produced as an IgG4 isotype to avoid/reduce complement-dependent cytotoxicity (CDC) and antibody-dependent cell-mediated cytotoxicity (ADCC). Complement-mediated killing is induced when antigen-antibody complexes bind a complement protein, C1q, through the Fc domain of the antibody, to initiate activation of a cascade of proteolytic events that results in the release of C5a and formation of a membrane attack complex that lyses targeted cells.

To demonstrate that hAb-Q did not induce CDC activity the following experiments were carried out.
Methods
Generation of Ramos E2 Clone Expressing High Levels of C5aR A CD20-expressing human B lymphocyte cell line (Burkitt's lymphoma-derived), Ramos, was stably transfected with a human C5aR expression plasmid (pcDNA3.1-C5aR; 4 µg DNA/$3 \times 10^6$ cells) using Lipofectamine™ LTX Reagent (Invitrogen) according to manufacturer's protocol. At 40 hours after transfection, Geneticin (G418 sulphate, Gibco) was added to the growth medium at 2 mg/ml. Cells (non-clonal) were grown in selective media for approximately 3 weeks at which time the C5aR expression and percent transfected was confirmed by flow cytometry using an anti-C5aR antibody. The cells were transferred into 384-well plates at a density to produce ~30-40 positive clones/plate. Single clonal colonies were selected and transferred to a 96-well plate for expansion. After sufficient growth, the expression of C5aR in each clone was determined by flow cytometry using an anti-C5aR antibody. The highest expressing clone, E2, was selected and expanded. Ramos E2 cells were maintained in RPMI, 10% FCS, 2 mg/ml G418.
CDC Assay with Rabbit Complement Target cells (Ramos E2 cells) were incubated with antibody or media alone (RPMI+10% heat-inactivated BCS) for 30 min at 37° C. in 5% $CO_2$. Following incubation, Rabbit complement (Cedarlane) diluted in RPMI, was added to samples for a final concentration of 1% v/v. Samples were incubated for a further 2 hrs at 37° C. in 5% $CO_2$.

The fluorescent viability dye, To-Pro-3 (Molecular Probes), was added to each sample before non-viable Target cells, defined as To-Pro-3 positive, were measured by flow cytometry and expressed as a percentage of total Target cells.

Specific CDC for each sample was calculated by subtracting the average % non-viable 'Targets Only' (A) from 'Targets & Complement' (B) of corresponding samples. The 'Media Only' sample of 'Targets & Complement' (C) was then subtracted from each sample to give a final value for specific CDC:

Specific $CDC(\% \text{ lysis})=(B-A)-C$

The above formula can also be expressed as follows:

Specific $CDC(\% \text{ lysis})=(T+CS-T+CMO)-(TOS-TOMO)$.

where: T+CS is average % non-viable cells in Target+Complement sample with antibody T+CMO is average % non-viable cells in Target+Complment media only (no Ab)

TOS is average % non-viable cells in Target Only sample with antibody

TOMO is average % non-viable cells in Target Only media only (no Ab)
CDC Assay with Human Serum ADCC assays using human serum were carried out as described below in Example 10. The CDC activity of an antibody was determined by subtracting the average % non-viable 'Targets Only/Media Only' sample (A) from 'Targets Only+Antibody' sample (B) containing human serum. Then the % non-viable 'Targets Only+Antibody' sample (C) minus 'Targets Only/Media Only' sample (D) in heat inactivated bovine serum reactions was subtracted to give a final value for specific CDC:

Specific $CDC(\% \text{ lysis})=(B-A)-(C-D)$

Results
CDC Assays of hAb-Q Using Ramos E2 Target Cells

The potential of hAb-Q to induce complement-dependent cytotoxicity (CDC) was initially investigated by incubating human neutrophils with antibody in the presence of rabbit complement. There was essentially no specific killing (<0.5% cell death) of neutrophils in this assay (data not shown).

Following development of the Ramos E2 cell line that expresses high levels of human C5aR as well as CD20, the question of whether hAb-Q could induce CDC was revisited. Two series of experiments using Ramos E2 cells as the target were performed. The first series used 1% rabbit complement, with rituximab serving as the positive control. The second series compared cell death in samples incubated with 10% human serum with cell death in samples incubated with heat-inactivated bovine serum.
Antibody hAb-Q Did Not Induce CDC of Ramos E2 Cells in the Presence of 1% Rabbit Serum Three assays wee carried out. The first involved incubating antibodies hAb-Q, rituximab (Roche) and hIgG4 isotype control (Sigma) at 10 µg/ml final concentration with Ramos E2 cells and 1% rabbit complement. The second and third assays were done with antibodies at 100 µg/ml and included an extra positive control, rabbit polyclonal anti-C5aR (US Biological).

In the first experiment the level of specific CDC in the samples incubated with 10 µg/ml hAb-Q, rituximab and hIgG4 was 0%, 96% and 0% respectively. In the second and third experiments the average specific CDC after incubation with 100 µg/ml hAb-Q, rituximab and hIgG4 was 1.5%, 98% and 1% respectively. Incubation of Ramos E2 with 20 µg/ml polyclonal and 1% rabbit complement produced 82% specific CDC (FIG. 30). Rituximab is reported to kill cells expressing CD20 by CDC. Polyclonal antibodies are also effective inducers of complement activation and CDC. These positive controls showed that the CDC assay was working and demonstrate that the humanized anti-C5aR antibody hAb-Q did not kill cells by CDC.
Antibody hAb-Q Did Not Induce CDC of Ramos E2 Cells in the Presence of 10% Human Serum A series of ADCC assays was conducted (see Example 10 below) using effector cells (PBMCs) isolated from human blood to target Ramos E2 cells incubated with humanized anti-C5aR or control antibodies. A set of control reactions carried out in parallel, involved incubating Ramos E2 cells ('target only') plus antibody in the presence of heat-inactivated bovine serum or 10% human serum from the same donor that provided the PBMCs.

The control reactions containing human serum were considered to represent CDC assays since they mimic the CDC assay described above, except with human serum rather than rabbit complement. One difference however, was that there was no Target+Antibody sample incubated without human serum. Therefore, in the assays using human serum, specific CDC was calculated by subtracting the "% non-viable target cells" in Target+Antibody sample incubated with heat-inactivated bovine serum from the "% non-viable target cells" in Target+Antibody sample incubated with human serum.

Seven assays using human serum were conducted. Ramos E2 cells were incubated with hAb-Q, rituximab or hIgG4 isotype control antibody at 1, 10 or 100 µg/ml in the presence of 10% heat-inactivated bovine serum or 10% human serum for 3 hours. The Ramos E2 cells were loaded with the dye PKH-26 prior to incubation and with viability dye ToPro3 after incubation to allow non-viable and viable cells to be distinguished. Specific CDC was calculated as described above with media only background subtracted from each sample in an assay. The average % non-viable target (Ramos E2) cells for each treatment with human serum less non-specific death observed in heat-inactivated bovine serum samples equated to specific CDC and results are shown in FIG. 31.

FIG. 31 shows that in samples containing hAb-Q there was a very low level of specific CDC (~1-2%) with no difference between doses. The level of Ramos E2 lysis was similar for both heat-inactivated bovine serum and human serum samples containing hAb-Q. A similar level of specific CDC (~0-4%) was observed in the samples incubated with the isotype control antibody. Importantly, there was no statistically significant difference ($p>0.05$) between the average amounts of lysis observed in samples incubated with hAb-Q versus the hIgG4 isotype antibody. This data suggests hAb-Q does not specifically mediate CDC. By contrast, specific CDC in samples containing rituximab was dose dependent and ranged from 72% with 1 µg/ml rituximab to 91% with 100 µg/ml rituximab. The high level killing observed with rituximab in the presence of human serum indicates that the assay was working and therefore it is concluded that hAb-Q does not mediate CDC. Were hAb-Q to mediate CDC, a similar level of killing to rituximab could be expected given that Ramos E2 clones express similar high levels of CD20 and hC5aR.

Example 10

Antibody-Dependent Cell Cytotoxicity Induced by Humanized Anti-C5aR Antibodies is Dependent on Heavy Chain Isotype It was desirable to develop a humanized anti-C5aR antibody that did not kill C5aR-expressing cells (neutrophils, monocytes, etc). Antibodies can initiate killing of cells expressing the target antigen by a number of mechanisms. Some humanized anti-C5aR antibodies (e.g. hAb-Q, hAb-J, hAb-G) were produced with $IgG_4$ isotype to avoid/reduce complement-dependent cytotoxicity (CDC) and antibody-dependent cell-mediated cytotoxicity (ADCC). Other humanized anti-C5aR antibodies (e.g. hAb-N, hAb-O) were produced with IgG1 isotype which is known to bind C1q and FcγR and therefore more likely to induce CDC and ADCC. ADCC is mediated when the Fc domain of an antibody bound to antigen—e.g. a receptor on a "target cell"—cross-links with Fc receptors on cells with cytotoxic potential ("effector cells") including natural killer (NK) cells, macrophages, monocytes, neutrophils and eosinophils.

To determine the level of ADCC activity induced by humanized anti-C5aR antibodies in vitro the following experiments were carried out.

Methods

ADCC Assay Protocol

Briefly, the effector cell component was prepared by isolating Peripheral Blood Mononuclear Cells (PBMCs) from a healthy donor using either Ficoll or Percoll (GE Healthcare) density gradient separation. Monocytes were then depleted from the PBMC population by adhering to a flask (1 hr, 37° C., 5% $CO_2$) with remaining, non-adherent cells (containing NK cells) incubated overnight in media containing 100 ng/ml of recombinant human IL-2 (Peprotech) at 37° in 5% $CO_2$.

The following day, Target cells (Ramos E2 cells expressing hC5aR—see above) were stained with the fluorescent cell membrane dye, PKH26 (Sigma), and $5\times10^4$ cells/sample were incubated with antibody or media alone for 30 min at 37° C. in 5% $CO_2$. Following incubation, either Effector cells at a ratio of 50:1, or media only was added to the Target cells and the samples were incubated for a further 3 hrs at 37° C. in 5% $CO_2$. The fluorescent viability dye, To-Pro-3 (Molecular Probes), was added to each sample before non-viable Target cells, defined as To-Pro-3 positive, were measured by flow cytometry and expressed as a percentage of total Target cells (PHK-26 positive cells). The medium contained either 10% human serum from the same donor that the PBMC "Effector" cells were isolated, or 10% heat-inactivated bovine serum.

Specific ADCC for each sample was calculated by subtracting the average % non-viable 'Targets Only' (A) from 'Targets & Effectors' (B) of corresponding samples. The 'Media Only' sample of 'Targets & Effectors' (C) was then subtracted from each sample to give a final value for specific ADCC:

Specific $ADCC(\% \text{ lysis}) = (B-A)-C$

The above formula can also be expressed as follows:

Specific $ADCC(\% \text{ lysis}) = (T+ES-T+EMO)-(TOS-TOMO)$.

where: T+ES is average % non-viable cells in Target+Effector sample with antibody T+EMO is average % non-viable cells in Target+Effector media only (no Ab)

TOS is average % non-viable cells in Target Only sample with antibody

TOMO is average % non-viable cells in Target Only media only (no Ab)

Results

The potential of the humanized anti-C5aR antibody hAb-Q to induce cell killing through ADCC mechanisms was examined in a series of assays using Ramos E2 cells as the target. Ramos E2 cells express both CD20 and C5aR allowing rituximab, which targets CD20 and kills by ADCC, to be used as a positive control. C5aR expression on Ramos E2 was ~7 times higher than on human neutrophils. It has been reported that the level of target receptor expressed on the cell surface may influence the degree of ADCC and CDC induced by an antibody (Preithener et al., 2006; van Meerten et al., 2006; Lowenstein et al., 2006).

The effector cells were human PBMCs purified from venous blood of healthy volunteers then depleted of monocytes and incubated overnight with IL-2 to stimulate ("prime") the NK cells. This step was found necessary to maximise the cytotoxicity of the effectors.

Target cells were labelled with the dye PKH-26 so they could be distinguished from effector cells during flow cytometry. For each target+antibody sample, 2 tubes were set up (each in duplicate). One contained target cells plus medium, the other contained effectors plus targets at a ratio of 50:1. The optimal Effector:Target ratio of 50:1 had been shown during assay development to produce maximum killing. Viability was measured by adding the dye To-Pro-3 (TP3) to samples after all incubation steps and analysing by flow cytometry. Target cell depletion was the number of non-viable target cells (TP3+ve/PKH+ve) as a percentage of total target cells (PKH+ve) after subtraction of background (no antibody sample).

Comparing ADCC Activity Induced by hAb-Q and hAb-N Using Ramos E2 as Target Cells In the first series of experiments, the potential of humanized anti-C5aR antibodies hAb-Q (heavy chain isotype hIgG4) and hAb-N (hIgG1) to induce ADCC of Ramos E2 cells was compared to ADCC induced by rituximab (hIgG1) and an isotype control antibody (hIgG4). Human IgG1 have higher affinity for FcγR than hIgG4 and would be expected to induce ADCC more efficiently.

Target cells were incubated with 100 μg/ml of hAb-Q, hAb-N, rituximab (Roche), hIgG4 antibody (Sigma) or media (RPMI) only in the presence of 10% heat-inactivated fetal calf serum (FCS). After 30 min, either IL-2 stimulated PBMCs (at a ratio of 50:1 (E:T)) or media only was added to Target cells and incubation continued for 3 hrs. The number of non-viable cells, measured by flow cytometry, was indicative of ADCC activity. Media only background and Target only background were subtracted from each sample to determine specific ADCC activity. Three identical experiments were performed. Results (combined data from three experiments±sd) are shown in FIG. 32.

Both IgG1 antibodies, rituximab and and anti-C5aR hAb-N, were effective in mediating high level killing (>65%) of Ramos E2 cells. By contrast the level of specific ADCC mediated by hAb-Q (IgG4) and the isotype control hIgG4 was significantly less, with only 23% Ramos E2 cells non-viable after incubation with PBMCs and hAb-Q. There was no death of Ramos E2 cells incubated with the isotype control antibody. These results suggest antibody isotype is an important determinant of ADCC activity and that the humanized anti-C5aR antibodies of hIgG4 isotype would be preferred for in vivo treatment if antibody-dependent cell killing is not desired.

Comparing Effect of Serum on ADCC Activity Mediated by hAb-Q with Ramos E2Cells as Target Another series of ADCC assays was conducted as above, with one set of samples incubated in medium containing 10% human serum isolated from the donor of the PBMC effector cells, and the duplicate set of samples containing 10% heat-inactivated bovine serum. Heat inactivation of serum is designed to destroy complement activity. Therefore it was expected that CDC activity might be observed in samples incubated with human serum. The level of CDC was determined from the 'target only' samples. Indeed, in 'target only' samples containing rituximab the number of non-viable (TP3+ve) cells was usually >90%. Therefore specific ADCC activity induced by rituximab in samples containing human serum could not be determined. However, in the parallel samples containing 10% heat-inactivated bovine serum plus 100 μg/ml rituximab, an average of 60% of target (Ramos E2) cells were specifically killed by the effector cells. This was similar to the results presented in FIG. 32 and indicated that the effector cells and ADCC assay was working.

Furthermore, as shown above in FIG. 31 the humanized anti-C5aR (hAb-Q) and hIgG4 isotype control antibodies did not induce CDC activity in this assay. Therefore specific ADCC due to hAb-Q and isotype control antibody could be calculated, as described above, for samples containing human serum. The results are shown in FIG. 33. Neither hAb-Q, nor the isotype control, at any concentration from 1-100 μg/ml, caused significant cell death by ADCC. For hAb-Q, this result contrasts with the ADCC activity observed in samples containing heat-inactivated bovine serum (FIG. 32).

Example 11

Mouse Studies

The KRN transgenic mouse line contains a T cell receptor that recognizes the autoantigen glucose-6-phosphate isomerase (GPI) on a C57BL/6 background. When these mice are crossed with NOD mice, transgene positive F1 offspring (K/B×N) spontaneously develop an autoimmune-like disease mediated by circulating antibody against GPI (Kouskoff et al., 1996). The serum from arthritic K/B×N mice can be transferred to other strains where autoantigenic immune complexes activate the alternative complement pathway, followed by C5aR- and Fc gamma RIII-mediated cell activation and production of inflammatory cytokines (Ji et al., 2002). Neutrophils, mast cells and macrophages play an important role in the development of pathology in this model (Wipke and Allen, 2001; Lee et al., 2002; Solomon et al., 2005). The inflammatory phenotype observed features many of the hallmarks of human rheumatoid arthritis including being a chronic progressive disease with joint destruction (Kyburz and Corr, 2003).

A. Humanized Antibodies to C5aR Reverse Inflammation in a Mouse Model of Inflammatory Arthritis
Methods
Animals Human C5aR knock-in transgenic mice on a C57BL/6 background (Lee et al., 2006) aged ~6-12 weeks were sourced from the breeding colony at the Garvan Institute, Sydney. Male mice were preferred for experiments although female mice were also used.

Preparation of K/B×N Serum

To produce serum for experiments, KRN males were crossed with NOD females. F1 offspring carrying the KRN transgene that developed inflamed joints were sacrificed and blood was collected by cardiac puncture. Serum was isolated after 2 hours incubation at 37° C. and centrifugation for 10 min at 4000 rpm. Serum from multiple mice was pooled, realiquoted and stored at −80° C.

Induction and Measurement of Experimental Arthritis

Experimental arthritis was induced in recipient mice by injecting 100-150 μl serum i.p. on days 0 and 2. Disease progress was monitored daily by measuring change in ankle thickness using callipers and determining clinical scores. Daily ankle thickness was determined by averaging two readings from each of the rear paws. The clinical score was calculated for each mouse by summing the scores for the four paws: 0, normal joint; 1, mild/moderate swelling of the ankle and/or one swollen digit; 2, swollen ankle or swelling in two or more digits; 3, severe swelling along all aspects of paw or all five digits swollen. The researcher monitoring the mice was blinded to the treatment each mouse had received.

Treatments

Purified anti-C5aR or isotype control antibodies (1-10 mg/kg in PBS) were injected i.p. on day 5 (therapeutic treatment regime). In some experiments, the control group received PBS rather than an isotype control antibody.

Statistical Analysis

The statistical significance of differences between independent control and treatment groups in the K/B×N model was determined using the Mann-Whitney test or using the Kruskal-Wallis test and post hoc analysis done with Dunn's Multiple Comparison Test.

Results

The ability of the humanized 7F3 antibodies to reverse established inflammation in K/B×N model was investigated and the results are reported below. Table 8 lists the antibodies tested in this model, and the doses administered. All antibodies were administered by i.p. injection "therapeutically" on day 5 after arthritis had been induced by K/B×N serum injection.

TABLE 8

Antibodies tested and the doses administered.

| Antibody | Dose Tested | Group Size | Results FIG. |
|---|---|---|---|
| G | 10 mg/kg | 6 | 34 |
| M | 10 mg/kg | 6 | 34 |
| N | 10 mg/kg | 6 | 34 |
| J | 1 mg/kg | 4 | 35 |
| J | 3 mg/kg | 5 | 35 |
| J | 10 mg/kg | 5 | 35 |
| C | 3 mg/kg | 5 | 35 |
| C | 10 mg/kg | 4 | 35 |

Results presented in FIGS. 34 and 35 show that the humanized antibodies were effective at reversing clinical signs of inflammation when administered i.p. at 10 mg/kg on day 5, after induction of inflammatory arthritis. Lower doses of antibodies J and C were less effective than the 10 mg/kg dose, but were able in most cases to prevent any further increase in inflammation, as was seen in the control groups (mice given PBS or a human IgG4—an isotype control antibody to an irrelevant human antigen).

B. Humanized Anti-C5aR Antibodies Reduce the Signs and Symptoms of Joint Inflammation in a Mouse Model of Rheumatoid Arthritis: Relationship between Antibody Dose, Antibody Serum Concentration, Receptor Occupancy and Efficacy Experimental arthritis was induced in mice prior to therapeutic administration of humanized anti-C5aR antibody. The relationship between antibody dose, antibody concentration in the serum, the level of C5aR occupancy by antibody and effect on joint inflammation in the mice was investigated.

Methods

Animals

Male and female human C5aR knock-in transgenic mice on a C57BL/6 background (Lee et al., 2006) aged between 8-16 (average ~12) weeks were sourced from breeding colonies at the Garvan Institute, Sydney or the Animal Resources Centre, Perth.

Preparation of K/BxN Serum

All mice in this study were injected with the same batch of K/BxN serum, prepared as described above.

FITC-Labelling of hAb-Q

Fluorescein isothiocyanate (FITC) was covalently conjugated to hAb-Q antibody as follows. Briefly, ~1.5 mg of hAb-Q was exchanged into "Reaction Buffer" (160 mM $Na_2CO_3$, 340 mM $NaHCO_3$, pH 9.5) and added to 120 μg FITC (Molecular Probes) dissolved in DMSO, per mg of antibody. The reaction was performed in the dark for 1 hr at room temperature (23° C.). Unconjugated FITC was removed using a PD-10 column, pre-equilibrated and eluted with "Storage Buffer" (10 mM Tris, 150 mM NaCl, pH 8.2). Conjugated hAb-Q-FITC was concentrated to achieve a final concentration of 1.036 mg/ml using a Centricon (YM-30) spin filter and stored at 4° C. in the dark.

Induction and Measurement of Experimental Arthritis

Experimental arthritis was induced in recipient mice by injecting 150 μl K/BxN serum i.p. on day 0 and day 2 as described above. On day 5, an "RA Score" was calculated for each mouse by multiplying the clinical score by the change in paw size from day 0 (in mm). Only mice that had an RA Score >0.5 were entered into the treatment stage of the study. Inflammatory arthritis developed in ~90% of male and 50% of female mice.

Study Design—Overview and Group Size

This study was designed to measure inflammation, in vivo receptor occupancy and serum antibody concentration in the K/BxN disease model at various times before and after treatment with anti-C5aR antibody commenced. The course of disease in this model is generally resolved within ~3 weeks. Signs and symptoms of inflammation are obvious within a day or two of immunization with serum from K/BxN mice. Inflammation peaks around day 10-14 and declines slowly thereafter.

Given these circumstances, the following schedule was adopted for analysis:

Inflammation: paw size and clinical score were measured on day 0 (prior to first serum injection), d2 (prior to second serum injection), 5 (prior to treatment commencing), then d6, d7, d8, d9, d10, d11, d12, d14 and d16. Inflammation was determined in at least 10 mice per group.

Serum antibody concentration: blood was sampled on day 5 (30 min and 12 hours after treatment), d6 (24 hours after treatment), d7 (48 hr), d8 (72 hr), d9 (96 hr), d10 (120 hr), d11 (144 hr), d12 (168 hr), d14 (192 hr) and d16 (264 hr). Serum was prepared from blood collected by cardiac puncture on days 5.5 (12 hours after treatment), 6, 8, 10, 12 and 16 and from tail vein bleeds on day 5 (30 min after treatment) and days 7, 9, 11 and 14. Groups of 2-4 mice provided blood at each time for each treatment, but each mouse was bled no more than 3 times. Approximately 100 μl blood was collected into 1.5 ml tubes (no anti-coagulant) and incubated at 37° C. for 30 min to promote clotting, followed by centrifugation at 13,000 rpm for 10 min. The serum was dispensed into fresh tubes (2 per mouse sample) and stored at −80° C. prior to determination of antibody concentration using an ELISA.

Receptor saturation: mice (n=4 per group) were sacrificed on days 5.5 (12 hours after treatment), 6, 8, 10 12 and 16 and blood collected by cardiac puncture. Leukocytes were stained with FITC-labelled hAb-Q to determine the amount of free C5a receptor or with FITC-labelled anti-human IgG to determine the amount of bound hAb-Q compared to PBS controls. Cells were co-stained with CD11b and Ly6G to distinguish neutrophils and monocytes. See below for further detail.

Treatments

Mice selected to enter the study were randomly divided into 5 groups to receive one of 5 treatments on day 5:
1. PBS i.p.
2. huIgG control antibody i.p.@8 mg/kg
3. hAb-Q i.p.@1 mg/kg
4. hAb-Q i.p.@3 mg/kg
5. hAb-Q i.p.@10 mg/kg Antibody was dissolved in PBS so that the total volume injected was ~100 μl per mouse. The researcher monitoring the mice was blinded to the treatment each mouse received. Treatment groups were not revealed until after data collection and analysis, except that animals given PBS were identified for receptor occupancy studies.

Group 1 (PBS control) was not treated with antibody was used to establish a baseline for the receptor saturation, activation and PK analysis. Group 2 was the negative control group treated with an irrelevant human IgG antibody. Groups 3-5 received the anti-C5aR treatment.

Statistical Analysis

The statistical significance of differences between independent control and treatment groups was determined as described above.

Measurement of Bound hAb-Q

Plates were set up to contain either hAb-Q (200 μg/ml, [final]) or dPBS for each test sample. 25 μl of heparinised blood from each mouse was added to both hAb-Q and dPBS-containing wells were incubated for 1.5 hr at 37° C. Cells were washed 3 times with dPBS to remove unbound hAb-Q and resuspended in dPBS containing anti-hIgG-FITC (1/50), anti-Ly-6G-PE and anti-CD11b-PerCP/Cy5.5 antibody (1/400) for 45 min at room temperature. Erythrocytes were removed with the addition of BD FACS Lysing Solution (BD, 349202). Sample plate was centrifuged at 2,000 rpm for 3 min, supernatant was removed and cells were again resuspended in BD FACS Lysing Solution for analysis by flow cytometry (BD FACSCanto).

Measurement of 'Free' C5a Receptor

Plates were set up to contain either hAb-Q (200 μg/ml, [final]), for minimum free C5aR) or dPBS (for maximum free C5aR and all test samples). 25 μl of heparinised blood from each mouse was added to corresponding well (i.e. mice injected with dPBS only were added to both +hAb-Q and dPBS-containing wells (for min and max free C5aR)). All other test blood samples were added to wells containing dPBS only and incubated for 1.5 hr at 37° C. Cells were washed 3 times with dPBS to remove excess hAb-Q and resuspended in dPBS containing hAb-Q-FITC at 25 μg/ml, anti-Ly-6G-PE and anti-CD11b-PerCP/Cy5.5 antibodies (1/400) for 45 min at 37° C. Erythrocytes were removed with the addition of BD FACS Lysing Solution (BD, 349202). Sample plate was centrifuged at 2000 rpm for 3 min, supernatant was removed and cells were again resuspended in BD FACS Lysing Solution for analysis by flow cytometry (BD FACSCanto).

Flow Cytometry Analysis of Neutrophil C5a Receptor Saturation

BD FACSCanto flow cytometer was set up with compensation parameters established for channels FL-1, FL-2 and FL-3. Samples were acquired to exclude dead cells and debris. Neutrophils were identified as Ly-6G-PE high, CD11b-PerCP/C5.5 low-high. Monocytes were identified as Ly-6G-PE negative, CD11b-PerCP/C5.5 high. The level of bound hAb-Q (α-IgG-FITC) and free C5aR (hAb-Q-FITC) was determined by measuring the FITC (FL-1) median fluorescence intensity (MFI) for each sample.

Percent bound hAb-Q was quantified by determining the MFI of each sample, incubated in dPBS, as a percentage of the MFI for the same sample incubated with 200 μg/ml hAb-Q (after subtraction of background which was calculated from the PBS treated mice samples incubated with PBS then FITC-anti-hIgG), according to the following equation:

$$[[MFI(\text{sample}+dPBS)-MFI(\text{background i.e. } PBS \text{ control mice}+dPBS)]/[\text{Max\_}MFI(\text{sample}+\text{cold hAb-}Q)-MFI(\text{background})]]\times100$$

Percent free C5a Receptor was quantified by determining the MFI of each sample, incubated in dPBS, as a percentage of maximum free receptor samples, i.e. mice administered dPBS only. Minimum free C5aR, i.e. samples incubated ex vivo with excess hAb-Q, were not used in this calculation but were used for comparison purposes.

Measurment of Antibody Serum Concentration

Serum concentrations of hAb-Q were assayed in compliance to GLP using an ELISA method validated to detect hAb-Q in mouse serum. Lowest limit of quantification (LLOQ) was 4 ng/ml. For the in vitro disappearance study, the mouse assay was qualified for detection of hAb-Q in human EDTA plasma. LLOQ was 10 ng/ml, when the assay was applied to plasma.

Results

Some 200 hC5aR KO/KI mice were immunised twice, 2 days apart (days 0 and 2) with serum from K/BxN mice in order to induce an inflammatory arthritis that manifests itself as swollen joints and digits in the paws of the recipient mice. By day 5 about 70% of the mice (~85% males and ~60% females) had developed some swelling and reddening of paws and joints. Mice with an "RA score" >0.5 were randomly sorted into 5 treatment groups of 11-12 mice per group. Each group was administered one of 5 treatments—hAb-Q in PBS at doses of 1, 3 and 10 mg/kg, a control antibody (human IgG to irrelevant antigen) in PBS at a dose of 8 mg/kg and PBS only. For the next 11 days mice were monitored regularly with a clinical score assigned and paw size (ankle thickness) measured. Blood samples were collected from the tail vein or by cardiac puncture on days 5.5, 6, 7, 8, 9, 10, 12, 14 and 16 for determination of receptor occupancy and antibody serum concentration.

Humanized Anti-C5aR Antibody Reverses Inflammation in the K/BxN Model of Inflammatory Arthritis in a Dose Dependent Manner The average clinical score and change in paw size from day 0 for each treatment group is shown in FIG. 36. The data shows that hAb-Q was effective in vivo in reducing the signs and symptoms of inflammation. A dose response relationship was observed, with the 10 mg/kg dose clearly more effective than the 3 and 1 mg/kg doses. Compared to the 2 control groups, 10 mg/kg hAb-Q reduced and controlled inflammation and clinical score for a week after administration, 3 mg/kg hAb-Q prevented any further increase in inflammation for about 5 days but was not able to reduce existing inflammation, and 1 mg/kg hAb-Q was not effective. Over the course of the final 3-5 days, there was a trend upward in the inflammation scores in both the 10 mg/kg and 3 mg/kg groups. Only a single dose of hAb-Q was given on day 5. As shown below, the reduction or levelling off (no further increase) of inflammation correlated with high receptor saturation and serum antibody concentration. As these fell, inflammation returned.

The Level and Extent of C5a Receptor Occupancy by Humanized Anti-C5aR Antibody is Dose Dependent Receptor occupancy was measured in two different ways. Leukocytes were stained with hAb-Q-FITC to determine the amount of "free" receptor, or with anti-hIgG-FITC to determine the amount of in vivo bound hAb-Q ("occupied" receptor) and co-stained with CD11b and Ly6G to distinguish neutrophils and monocytes. There should be an inverse relationship between the amount of antibody bound to the C5aR on neutrophils and the amount of free (empty) receptor. When calculating bound antibody, mouse-to-mouse variation in the receptor number was corrected for. This was not done when determining free receptor. Results are shown in FIGS. 37 and 38.

FIG. 37 shows the relationship between administered antibody dose and bound anti-C5aR antibody in neutrophils. At the highest dose, 10 mg/kg, bound antibody remained at saturating levels until ~120 hours after administration (day 10) then fell to ~20% occupancy by 264 hr (day 16). At 3 mg/kg, bound antibody was at saturating levels for ~24 hours, then fell to 50% by 72 hours and 15% by 120 hours. The 1 mg/kg dose was not sufficient to produce saturation binding of antibody, with receptor occupancy only 75% at 24 hours after dosing. By 72 hr there was virtually no hAb-Q bound to the neutrophils. Similar results were observed in monocytes (not shown).

FIG. 38 shows that the level of "free" receptor was inversely related to the percent of "occupied" receptors (bound antibody shown in FIG. 37). There was very little free receptor on neutrophils in the mice treated with 10 mg/kg hAb-Q until a week after dosing. In the 3 mg/kg group there was little free receptor until after 72 hours, and in the 1 mg/kg group free receptor increased dramatically after 24 hours post dosing. Similar results were observed for monocytes (not shown).

The Level and Extent of Humanized Anti-C5aR Antibody Concentration in Serum is Dose Dependent The concentration of humanized anti-C5aR antibody in the serum of animals was determined at intervals between 30 min and 11 days after administration. Results are shown in FIG. 39. After administration, the concentration of hAb-Q in the serum increased rapidly. The maximum concentration measured was reached between 30 min and 12 hr after administration and was dose dependent. After administration of 1 mg/kg antibody concentration in the serum peaked at 1.9 μg/ml after 30 min, remained above 1.5 μg/ml for 12 hours then fell to <0.1 μg/ml on day 7 (48 hours after administration). The peak serum antibody concentration in the 3 mg/kg group was 13.3 μg/ml 12 hours after administration. Antibody levels remained high (>5 μg/ml) for 2 days then fell rapidly to <0.1 μg/ml by day 9 (96 hours after administration). Serum antibody concentration in the 10 mg/kg group peaked at 69.5 μg/ml 12 hours after administration and declined gradually over the next 7 days to 5.5 μg/ml, then to <0.1 μg/ml by day 14.

Reduction in, or Stabilization of Inflammation Correlates with High Receptor Occupancy and High Serum Antibody Concentration Data from FIGS. 36a (clinical score), 37 (% hC5aR occupied by hAb-Q) and 39 (hAb-Q concentration in serum) above have been combined in FIGS. 40, 41 and 42 to demonstrate the relationship between antibody dose, receptor occupancy and serum antibody concentration.

When experimental arthritis is induced in the mice by injection of K/BxN serum there is an increase in joint and paw swelling and redness, which is quantified (expressed as a clinical score) using an "arthritis index" as described above. When humanised anti-C5aR antibody hAb-Q was administered "therapeutically" i.e. on day 5 after inflammation had developed in mice given K/BxN serum on days 0 and 2, there was a sustained reduction in the severity of inflammation in the group of mice that received the highest dose (10 mg/kg). FIG. 40 shows that the level of inflammation (clinical score) in this group fell between days 5 and 12 at the same time as receptor occupancy was high (>40%) and that high levels of hAb-Q (>5 μg/ml) were measured in the serum. Mice administered 3 mg/kg hAb-Q recorded a slight fall in inflammation over the following 3 days before starting to trend upwards again over the next 4 days. FIG. 41 shows that at the same time serum antibody concentration was >5 μg/ml and receptor occupancy was ≧50% in the mice given 3 mg/kg hAb-Q. After day 8 both serum antibody concentration and receptor occupancy fell rapidly, which corresponded to the period inflammation began to trend upwards again. When mice were administered 1 mg/kg hAb-Q, the lowest dose, there was a pause of about 1 day in the steadily increasing level of inflammation as evidenced by the clinical score (FIG. 42). At the same time antibody levels in the serum were falling rapidly, from a peak of 1.8 μg/ml immediately after injection, and 1.5 μg/ml at 12 hours. C5aR occupancy remained >50% for just 1 day before declining rapidly.

Taken together these data support the proposal that high receptor occupancy is dependent on high Ab concentration in the serum and that the reduction in leukocytes in the joints as observed in histological sections and as measured by reduction in paw size and clinical score is dependent on high levels of receptor occupancy (low "free" receptor). Without free receptor C5a cannot bind C5aR to cause activation and migration of leukocytes from the blood to sites of inflammation and complement activation in the tissues.

C. PK/PD Relationship of hAb-Q in the K/BxN Mouse Model

In this example, we provide a plausible pharmacokinetic/pharmacodynamic (PK/PD) model that describes the quantitative relationship between the pharmacokinetics of an anti-C5aR mAb, target receptor occupancy, and effect in the K/BxN mouse model of inflammatory arthritis. Data for the modelling was generated from two studies, a pharmacology study (described in Example 11B above) and a toxicology study. This model constitutes a method for interpretation of data, to explore the concentration response relationship, and may be used to support selection of a safe starting dose in humans.

Methods

Pharmacology Study

Full details of the pharmacology study methods are given above in Example 11B. In brief, the aims of this study were to determine, firstly whether therapeutic treatment with the humanised anti-C5aR antibody, hAb-Q, was effective in reversing the signs and symptoms of inflammatory arthritis in the K/BxN model; and secondly, to correlate dose with anti-inflammatory effect, the level of receptor occupancy (measured as free hC5aR and bound hAb-Q), neutrophil activation status and circulating serum antibody concentration. Inflammation was determined in at least 10 mice per group. The receptor saturation study was done with 4 mice per group, except that the control groups given PBS included 2 mice. Dosing groups (1, 3, 10 mg/kg, i.p., and control animals).

Toxicology Study

Toxicity study by subcutaneous and intravenous (bolus) administration of hAb-Q to hC5aR transgenic mice, with doses administered on alternate days. Toxicokinetic data was obtained from 18-21 males and 18-21 females in each of four hAb-Q dosing groups (5, 50, 500 mg/kg, i.v., and 100 mg/kg subcutaneous (s.c.)).

Pharmacokinetics

Serum concentrations of hAb-Q were assayed as described above.

Receptor Occupancy

Binding to hC5aR on neutrophils and monocytes by the administered hAb-Q mAb was determined as described above. For the pharmacology study, occupancy was calculated as, $$\text{Occupancy} = \% \text{ Bound} = 100\% \frac{MFI_{bound} - MFI_{bound.pre}}{MFI_{max.bound} - MFI_{bound.pre}}$$

The pre values were subtracted, since these were considered to provide the background MFI.

Model Development

NONMEM VI (non-linear mixed effects modelling software) with first order conditional estimation (FOCE) was used for modelling, and S-PLUS® 8.0 (Insigthful) was used for graphics and data handling. Evaluation of—and discrimination between—intermediate models was based on objective function values and standard graphical evaluation methods. In terms of objective function value, changes in this value were assumed to be chi-squared distributed (for nested models), and criteria for expanding the model were defined and used accordingly.

Results
PK/PD Relationship for Occupancy

Toxicokinetics from the toxicology study in transgenic mice and PK/PD data from the pharmacology study was integrated to assess the relationship between pharmacokinetics and occupancy. These data could be well described by a one-compartment PK model with target mediated disposition, as illustrated in FIG. 43. The PK and occupancy model fit for each dosing group is shown in FIG. 44, while parameter values are given in Table 9. Note also that a higher clearance was estimated for the 500 mg/kg group than for lower dose levels in the toxicology study. This is consistent with other studies, observing higher clearance for high doses, due to saturation of the FcRN receptor (Hansen and Balthasar, 2002).

TABLE 9

Pharmacokinetic Parameters for hAb-Q in Transgenic in a Toxicology Study and a Pharmacology Study

| | Unit | Pharmacology | Toxicology |
|---|---|---|---|
| $V_1$ | mL/kg | 74.3 | 74.3 |
| CL | mL/h/kg | 0.182 | 1.37-2.52* |
| ka.sc | 1/h | — | 0.0935 |
| ka.ip | 1/h | 4.26 | — |
| F.sc | 1 | — | 0.438 |
| F.ip | 1 | 0.411 | — |
| Kd | ng/mL | 175 | 175 |
| koff | 1/h | 0.1 | 0.1 |
| Bmax.Targ | µg/kg | 196 | 196 |
| Turnover | h | 14.2 | 14.2 |

*From the KO/KI hC5aR mice in the Tox study, a higher clearance was found in the 500 mg/kg group.
$V_1$ = central volume,
CL = clearance,
ka.sc/ka.ip are the absorption rate constants for s.c. or i.p. administration.
F.sc/F.ip are the bioavailabillity for s.c. or i.p. administration.
Kd = affinity for specific binding.
koff = off rate constant.
Bmax.Targ = Maximal target binding capacity for hAb-Q.
Turnover = Time it takes to renew the target and remove bound antibodies. (koff was fixed to 0.1 1/h).

PK/PD Relationship for Effect on Inflammation

A PK/PD model was developed to describe the relationship between the pharmacokinetics and the change in paw size after an inflammatory challenge in the pharmacology study (K/B×N model) using transgenic mice. The natural course of the K/B×N model is a gradual increase in paw size due to the induction of experimental arthritis with a subsequent gradual return after approximately 12 days towards normal paw size as the inflammation wanes off. The PK/PD model illustrated in FIG. 45 describes the effect of hAb-Q via inhibition of the induced inflammation. The percent of maximum inhibition was set to the level of occupancy obtained from the occupancy PK/PD model. As seen in FIG. 46, reasonable concordance between the measured and modelled paw size could be obtained by this approach, which illustrate a very close relationship between occupancy of the neutrophil C5a-receptors and the effect on inflammation.

KO/KI hC5aR mice (n≧10/time point/group) were subjected to induction of experimental arthritis at day 0, and injected with 1, 3, 10 or 0 mg/kg anti-C5aR (hAb-Q) at day 5. After approximately 12 days the paw size started to decrease, as the inflammation induced increase waned off. Likewise, with occupancy near 100%, the inflammation induced increase was inhibited, and for the 10 mg/kg group a small decrease in paw size was seen. In the model, these processes are related, both described by the natural return towards normal paw size.

The model predicted that the dominant part of the effect of hAb-Q is obtained at a concentration leading to full occupancy of the receptor on circulating neutrophils. At 1 mg/kg, the occupancy was high only for 1-2 days after dosing, and hereafter the paw size started to increase again, see FIG. 46. Similarly, 3 mg/kg leads to approximately 72 hours of high occupancy, where after the paw size started to increase again. At 10 mg/kg, approximately 10 days of occupancy is obtained leading to about the same time span for inhibition of paw inflammation.

Using the presented plausible model, we observe that when the occupancy was above 50%, the growth of the paw size was inhibited, and when occupancy decreased below 50%, e.g. after day 8 in the 3 mg/kg group, the paw size resumed the inflammation driven increase. Since the model associates 50% inhibition with 50% occupancy, the good fit gave a quantitative confirmation 1) that occupancy and effect on inflammation are tightly connected, and 2) that peak occupancy at 50% is expected to give a minimal effect on inflammation.

Conclusions

The model demonstrated a tight relationship between mAb concentration, occupancy, and effect on inflammation, and a good agreement was found between observed and predicted values. The most important features in the data were described by the model: 1) a clear beneficial effect on the mouse paw motivating further clinical development. 2) a high saturable elimination component described by target mediated disposition, which may lead to the requirement of high dose levels for long term therapeutic effect, and 3) a relative strong binding to the receptor in vivo, likely related to bivalent binding, which may lead to high peak occupancy at low doses.

This model was used as part of the package used to construct a human simulation model based on all relevant preclinical data to select a safe starting dose in the first human trial.

Example 12

PK/PD Model Update with Human Data

Data from on-going clinical trial with hAb-Q was used to validate and update the preclinical PK/PD model described in Example 11, using pharmacokinetic and C5aR-occupancy data. Simulations of this model are used to describe the current predictions for PK/PD at higher dose levels. This model constitutes a method for interpretation of data for early decision making regarding dose level and regimen selection in future studies.

Methods
Clinical Data

NN8209-1940 is a randomised, double-blind, placebo-controlled, dose escalation trial of single i.v. and s.c. doses in parallel at 8 and 7 dose levels, respectively. The subjects are randomised to a single i.v. or s.c. dose of anti-C5aR (hAb-Q). Subjects are randomised in a 3:1 ratio, where three subjects will be allocated to active treatment at each dose level and route of administration and one subject to placebo treatment. Anti-C5aR (hAb-Q) will be administered at planned dose levels with the actual increase of dose by 3 or 3.3 fold from previous dose level. Current dose levels included in the PK/PD model update: i.v. dose levels: 0.003, 0.01, 0.03, 0.1, 0.2, 0.6 mg/kg; s.c. dose levels: 0.01, 0.03, 0.1, 0.3 mg/kg.

Data not included in modelling, pending trial completion, include planned dose levels: 2 and 7 mg/kg i.v. and 1 and 3 mg/kg s.c.

Sampling Schedules

PK sampling for measurement of anti-C5aR (hAb-Q) is planned prior to dosing at 0 hours (max 60 minutes prior to dosing) and at 5 minutes (after i.v. administration only), 15 minutes (after i.v. administration only), and 30 minutes, and at 1, 2, 4, 6, 8, 12, 24 and 48 hours and 3, 7, 14, 21, 28, 42, 56, and 70 days after drug administration. The time points refer to start of injection or infusion at 0 minutes. For subjects randomised to i.v. administration, the infusion time is 15 minutes and the time point of 15 minutes will therefore refer to at end of infusion.

Sampling for C5aR-occupancy on neutrophils and monocytes is planned prior to dosing at 0 hours (max 60 minutes prior to dosing) and at 4, 24, and 48 hours and 3, 7, 14, 21, 42, and 70 days after drug administration.

Occupancy Calculation

Binding to hC5aR on neutrophils and monocytes by the administered hAbQ mAb was determined using three different methods. Following analysis by FACS, each of these measures gives rise to a corrected mean fluorescence intensity (MEF). The three methods are; 1) a direct method using a FITC-labeled anti-human IgG$_4$ secondary antibody to assess occupied receptors that have bound hAbQ in vivo (MEF$_{bound}$); 2) an indirect method, measuring free hC5a receptors as a result of in vivo hAb-Q administration, followed by addition of hAb-Q-FITC ex vivo (MEF$_{free}$); and 3) a measure for total receptor number, incubation with excess hAb-Q ex vivo to fill up all receptors and then addition of anti-human secondary antibody (MEF$_{max.bound}$). The occupancy was subsequently derived as:

$$\% \text{ Bound} = 100\% \frac{MEF_{bound} - MEF_{bound.backgr}}{MEF_{max.bound} - MEF_{bound.backgr}}$$

$$\% \text{ Free} = 100\% \frac{MEF_{free} - MEF_{free.backgr}}{MEF_{free.pre} - MEF_{free.backgr}}$$

$$\text{Occupancy} = 100\% \frac{\% \text{ Bound}}{\% \text{ Free} + \% \text{ Bound}}$$

Model Development

NONMEM VI with first order conditional estimation (FOCE) was used for modelling, and S-PLUS® 8.0 was used for graphics and data handling. Evaluation of—and discrimination between—intermediate models was based on objective function values and standard graphical evaluation methods. In terms of objective function value, changes in this value were assumed to be chi-squared distributed (for nested models), and criteria for expanding the model were defined and used accordingly.

The updated model was estimated from data. However, current data may be insufficient for robust estimation of all parameters. In this case some parameters were fixed to the parameter values of typical IgG parameters.

Results

The current updated model for human PK and occupancy is described in FIG. 47. The model predictions were in general found to be in very good agreement with the pharmacokinetics and occupancy observed so far in the experiment. These model predictions of PK/PD following anti-C5aR (hAb-Q) administration are given in FIG. 48 for i.v. dosing, and FIG. 49 for s.c. dosing. Note that these predictions are likely to change upon accumulation of data.

The model is highly non-linear, making predictions more difficult than for linear pharmacokinetics. Based on current data, only little information contributes to the elimination half-life at high dose levels, implying that some uncertainty should be taken into account, especially for the prediction of high dose levels. For s.c. dosing, available pharmacokinetic data is still close to lower limit of quantification, which means that mainly occupancy data contributes to the estimation of bioavailability.

Conclusions

Overall, a good agreement was found between observed and predicted PK and occupancy. The main features predicted from preclinical data were also observed in the clinical data. These features include a high saturable component of the elimination, which is likely due to the target, and a relatively high occupancy at low concentrations.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/066,539 filed 20 Feb. 2008, the entire contents of which are incorporated herein by reference.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References

Barry et al. (1994) J. Biol. Chem. 269: 3623-32.
Berman et al. (1998) Immunol. Invest. 17: 625-677.
Caldas et al. (2000) Protein Eng. 13: 353-360.
Caldas et al. (2003) Mol. Immunol. 39: 941-952.
Caron et al. (1992) J. Exp Med. 176: 1191-1195.
Chothia and Lesk (1987) J. Mol. Biol. 196: 901-17.
Chothia et al. (1989) Nature 342: 877-883.
Co et al. (1992) J. Immunol. 148: 1149-54.
Curiel et al. (1992) Hum. Gene Ther. 3: 147-154.
Dahinden et al. (1994) J. Exp. Med. 179: 751-756.
Dai et al. (1992) Proc. Natl. Acad. Sci. USA 89: 10892-10895.
Eigenbrot et al. (1993) J. Mol. Biol. 229: 969-95.
Gerard and Gerard (1991) Nature 349: 614-617.
Gerard and Gerard (1994) Ann. Rev. Immunol. 12: 775-808.
Hansen and Balthasar (2002) Thromb. Haemost. 88: 898-899.
Hendrickson et al. (1995) Nucl. Acids Res. 23: 522-529.
Ji et al. (2002) Immunity 16: 157-168.
Jones et al. (1986) Nature 321: 522-525.
Jose et al. (1994) J. Exp. Med. 179: 881-887.
Kaneko et al. (1995) Immunology 86: 149-154.
Kavanaugh et al. (1991) J. Immunol. 146: 4149-4156.
Konteatis et al. (1994) Journal of Immunology 153: 4200-4205.
Kouskoff et al. (1996) Cell 87: 811-822.
Kozlov et al. (2004) Biopolymers 73: 621-630.
Kyburg and Corr (2003) Springer Semin Imunopathol. 25: 79-90.
Lebkowski et al. (1988) Mol. Cell. Biol. 8: 3988-3996.
Lee et al. (2002) Science 297: 1689-1692.
Lee et al. (2006) Nat. Biotech. 24: 1279-1284.
Lowenstein et al. (2006) Transplant International 19: 927-936
Martin et al. (1989) Proc. Natl. Acad. Sci. USA 86: 9268-72.
Mayo and Curnutte (1990) Methods Enzymol. 186: 567-75.

Morgan et al. (1993) Journal of Immunology 151: 377-388.
Murdoch and Finn (2000) Blood 95: 3032-3043.
Needleman and Wunch (1970) J. Mol Biol. 48: 444-453.
Neote et al. (1993) Cell 72: 415-425.
Niemeyer et al. (2003) Nucl. Acids Res. 31: e90.
Nisihara et al. (2001) J. Immunol. 167: 3266-3275.
Pellas et al. (1998) J. Immunology 160: 5616-5621.
Preithener et al. (2006) Mol Immunol 43: 1183-1189.
Pulito et al. (1996) J. Immunol. 156: 2840-50.
Queen et al. (1986) Immunol. Rev. 89: 49-68.
Shopes (1992) J. Immunol. 148: 2918-2922.
Solomon et al. (2005) Eur J Immunol. 35: 3064-3073.
Stevenson et al. (1989) Anti-Cancer Drug Design 3: 219-230.
Ulmer et al. (1993) Science 259: 1745-1748.
Van Damme et al. (1992) J. Exp. Med. 176: 59-65.
Van Meerten et al. (2006) Clin Cancer Res 12: 4027-4035.
Van Riper et al. (1993) J. Exp. Med. 177: 851-856.
Verhoeyen et al. (1988) Science 239: 1534-1536.
Vitetta (1993) Immunol. Today 14: 252.
Vitetta et al. (1987) Science 238: 1098-1104.
Watanabe et al. (1995) J. Immunol. Meth. 185: 19-29.
Williams et al. (1991) Proc. Natl. Acad. Sci. USA 88: 2726-2730.
Wipke and Allen (2001) J Immunol. 167: 1601-1608.
Wolff et al. (1993) Cancer Research, 53: 2560-2565.
Wu and Wu (1987) J. Biol. Chem. 262: 4429-4432.
Zachariae et al. (1990) J. Exp. Med. 171: 2177-2182.

The invention claimed is:

1. A substantially purified humanized antibody comprising:
   i) an immunoglobulin light chain comprising a variable region comprising an amino acid sequence provided as SEQ ID NO: 31; and
   ii) an immunoglobulin heavy chain comprising a variable region comprising an amino acid sequence provided as SEQ ID NO: 36, wherein the antibody binds human C5aR.

2. The humanized antibody of claim 1, comprising:
   i) an immunoglobulin light chain comprising a constant region comprising an amino acid sequence provided as SEQ ID NO: 41; and
   ii) an immunoglobulin heavy chain comprising a constant region comprising an amino acid sequence provided as SEQ ID NO: 45.

3. The humanized antibody of claim 1 which is a four-polypeptide chain structure consisting of two heavy and two light chains.

4. The humanized antibody of claim 1 which is a single chain antibody.

5. The humanized antibody of claim 1 which is a diabody.

6. The humanized antibody of claim 1 which is a triabody.

7. The humanized antibody of claim 1 which is a tetrabody.

* * * * *